United States Patent [19]
Ozaki et al.

[11] Patent Number: 5,854,040
[45] Date of Patent: Dec. 29, 1998

[54] PROCESS FOR PRODUCING TRANS-4-HYDROXY-L-PROLINE

[75] Inventors: Akio Ozaki; Hideo Mori; Takeshi Shibasaki; Katsuhiko Ando, all of Machida; Shigeru Chiba, Kawasaki, all of Japan

[73] Assignee: Kyowa Hakko Kogyo Co., Ltd., Tokyo, Japan

[21] Appl. No.: 709,874

[22] Filed: Sep. 9, 1996

Related U.S. Application Data

[63] Continuation-in-part of Ser. No. 482,554, Jun. 7, 1995, abandoned, which is a continuation-in-part of Ser. No. 301,653, Sep. 7, 1994, abandoned.

[30] Foreign Application Priority Data

Sep. 7, 1993 [JP] Japan ................................. 5-221940
Dec. 27, 1993 [JP] Japan ................................. 5-332561

[51] Int. Cl.$^6$ .................................................. C12N 9/02
[52] U.S. Cl. ...................... 435/189; 435/107; 435/252.3; 435/252.33; 435/320.1; 536/23.1; 536/23.2
[58] Field of Search .................................... 435/189, 107, 435/252.3, 252.33, 320.1; 536/23.1, 23.2

[56] References Cited

PUBLICATIONS

Lawrence et al. "Purification and initial characterization of proline 4–hydroxylase from *Streptomyces griseoviridus* P8648: a 2–oxoacid, ferrous–dependent dioxygenase involved in etamycin biosynthesis" Biochem. J. 313, 185–191, 1996.

Onishi et al. "Proline hydrixylation by cell free extract of a streptomycete" Biochem. Biophys. Res. Comm. 120, 45–51, Apr. 1984.

Baldwin et al. "Proline 4–hydroxylase: stereochemical course of the reaction" Tetrahedron Lett. 34, 7489–7492, Nov. 1993.

*Primary Examiner*—Rebecca E. Prouty
*Assistant Examiner*—Nashaat T. Nashed
*Attorney, Agent, or Firm*—Antonelli, Terry, Stout & Kraus, LLP

[57] ABSTRACT

Isolated and purified L-proline-4-hydroxylase which catalyzes hydroxylation of L-proline at the 4-position of L-proline in the presence of 2-ketoglutaric acid and a divalent iron ion to produce trans-4-hydroxy-L-proline. The L-proline-4-hydroxylase may be isolated from a microorganism selected from the group consisting of Dactylosporanlium sp. RHI deposited with the National Institute of Bioscience and Human-Technology Agency of Industrial Science and Technology, Japan, under the designation PERM BP-4400 and Amycolatopsis sp. RH2 deposited as FERM BP-4581.

4 Claims, 14 Drawing Sheets

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Dactylosporangium sp.
        ( B ) STRAIN: RH1

( x i ) SEQUENCE DESCRIPTION: SEQ ID NO:1:

```
Met  Leu  Thr  Pro  Thr  Glu  Leu  Lys  Gln  Tyr  Arg  Glu  Ala  Gly  Tyr  Leu
 1                    5                        10                       15
Leu  Ile  Glu  Asp  Gly  Leu  Gly  Pro  Arg  Glu  Val
                    20                        25
```

( 2 ) INFORMATION FOR SEQ ID NO:2:

( i ) SEQUENCE CHARACTERISTICS:
        ( A ) LENGTH: 272 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Dactylosporangium sp.
        ( B ) STRAIN: RH1

( x i ) SEQUENCE DESCRIPTION: SEQ ID NO:2:

```
Met  Leu  Thr  Pro  Thr  Glu  Leu  Lys  Gln  Tyr  Arg  Glu  Ala  Gly  Tyr  Leu
 1                    5                        10                       15
```

-continued

| | | | | | | | | | | | | | | |
|---|---|---|---|---|---|---|---|---|---|---|---|---|---|---|
| Leu | Ile | Glu | Asp<br>20 | Gly | Leu | Gly | Pro | Arg<br>25 | Glu | Val | Asp | Cys | Leu<br>30 | Arg | Arg |
| Ala | Ala | Ala<br>35 | Ala | Leu | Tyr | Ala | Gln<br>40 | Asp | Ser | Pro | Asp | Arg<br>45 | Thr | Leu | Glu |
| Lys | Asp<br>50 | Gly | Arg | Thr | Val | Arg<br>55 | Ala | Val | His | Gly | Cys<br>60 | His | Arg | Arg | Asp |
| Pro<br>65 | Val | Cys | Arg | Asp | Leu<br>70 | Val | Arg | His | Pro | Arg<br>75 | Leu | Leu | Gly | Pro | Ala<br>80 |
| Met | Gln | Ile | Leu | Ser<br>85 | Gly | Asp | Val | Tyr | Val<br>90 | His | Gln | Phe | Lys | Ile<br>95 | Asn |
| Ala | Lys | Ala | Pro<br>100 | Met | Thr | Gly | Asp | Val<br>105 | Trp | Pro | Trp | His | Gln<br>110 | Asp | Tyr |
| Ile | Phe | Trp<br>115 | Ala | Arg | Glu | Asp | Gly<br>120 | Met | Asp | Arg | Pro | His<br>125 | Val | Val | Asn |
| Val | Ala<br>130 | Val | Leu | Leu | Asp | Glu<br>135 | Ala | Thr | His | Leu | Asn<br>140 | Gly | Pro | Leu | Leu |
| Phe<br>145 | Val | Pro | Gly | Thr | His<br>150 | Glu | Leu | Gly | Leu | Ile<br>155 | Asp | Val | Glu | Arg | Arg<br>160 |
| Ala | Pro | Ala | Gly | Asp<br>165 | Gly | Asp | Ala | Gln | Trp<br>170 | Leu | Pro | Gln | Leu | Ser<br>175 | Ala |
| Asp | Leu | Asp | Tyr<br>180 | Ala | Ile | Asp | Ala | Asp<br>185 | Leu | Leu | Ala | Arg | Leu<br>190 | Thr | Ala |
| Gly | Arg | Gly<br>195 | Ile | Glu | Ser | Ala | Thr<br>200 | Gly | Pro | Ala | Gly | Ser<br>205 | Ile | Leu | Leu |
| Phe | Asp<br>210 | Ser | Arg | Ile | Val | His<br>215 | Gly | Ser | Gly | Thr | Asn<br>220 | Met | Ser | Pro | His |
| Pro<br>225 | Arg | Gly | Val | Val | Leu<br>230 | Val | Thr | Tyr | Asn | Arg<br>235 | Thr | Asp | Asn | Ala | Leu<br>240 |
| Pro | Ala | Gln | Ala | Ala<br>245 | Pro | Arg | Pro | Glu | Phe<br>250 | Leu | Ala | Ala | Arg | Asp<br>255 | Ala |
| Thr | Pro | Leu | Val<br>260 | Pro | Leu | Pro | Ala | Gly<br>265 | Phe | Ala | Leu | Ala | Gln<br>270 | Pro | Val |

( 2 ) INFORMATION FOR SEQ ID NO:3:

( i ) SEQUENCE CHARACTERISTICS:
        ( A ) LENGTH: 816 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Dactylosporangium sp.
        ( B ) STRAIN: RH1

( i x ) FEATURE:
        ( C ) IDENTIFICATION METHOD: by experiment ( x i ) SEQUENCE DESCRIPTION: SEQ ID NO:3:

| | | | | | |
|---|---|---|---|---|---|
| ATGCTGACCC | CGACGGAGCT | CAAGCAGTAC | CGCGAGGCGG | GCTATCTGCT | CATCGAGGAC | 60 |
| GGCCTCGGCC | CGCGGGAGGT | CGACTGCCTG | CGCCGGGCGG | CGGCGGCCCT | CTACGCGCAG | 120 |
| GACTCGCCGG | ACCGCACGCT | GGAGAAGGAC | GGCCGCACCG | TGCGCGCGGT | CCACGGCTGC | 180 |
| CACCGGCGCG | ACCCGGTCTG | CCGCGACCTG | GTCCGCCACC | CGCGCCTGCT | GGGCCCGGCG | 240 |
| ATGCAGATCC | TGTCCGGCGA | CGTGTACGTC | CACCAGTTCA | AGATCAACGC | GAAGGCCCCG | 300 |
| ATGACCGGCG | ATGTCTGGCC | GTGGCACCAG | GACTACATCT | TCTGGGCCCG | AGAGGACGGC | 360 |

| | | | | | |
|---|---|---|---|---|---|
| ATGGACCGTC | CGCACGTGGT | CAACGTCGCG | GTCCTGCTCG | ACGAGGCCAC | CCACCTCAAC | 420 |
| GGGCCGCTGT | TGTTCGTGCC | GGGCACCCAC | GAGCTGGGCC | TCATCGACGT | GGAGCGCCGC | 480 |
| GCGCCGGCCG | GCGACGGCGA | CGCGCAGTGG | CTGCCGCAGC | TCAGCGCCGA | CCTCGACTAC | 540 |
| GCCATCGACG | CCGACCTGCT | GGCCCGGCTG | ACGGCCGGGC | GGGGCATCGA | GTCGGCCACC | 600 |
| GGCCCGGCGG | GCTCGATCCT | GCTGTTCGAC | TCCCGGATCG | TGCACGGCTC | GGGCACGAAC | 660 |
| ATGTCGCCGC | ACCCGCGCGG | CGTCGTCCTG | GTCACCTACA | ACCGCACCGA | CAACGCCCTG | 720 |
| CCGGCGCAGG | CCGCTCCGCG | CCCGGAGTTC | CTGGCCGCCC | GCGACGCCAC | CCCGCTGGTG | 780 |
| CCGCTGCCCG | CGGGCTTCGC | GCTGGCCCAG | CCCGTC | | | 816 |

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:4:

ATGCTSACSC CNACNGA         17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:5:

GGSCCSAGNC CRTCYTC         17

( 2 ) INFORMATION FOR SEQ ID NO:6:

( i ) SEQUENCE CHARACTERISTICS:
        ( A ) LENGTH: 71 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:6:

```
ATG CTG ACG CCG ACG GAG CTC AAG CAG TAC CGC GAG GCG GGC TAT CTG      48
Met Leu Thr Pro Thr Glu Leu Lys Gln Tyr Arg Glu Ala Gly Tyr Leu
 1               5                  10                  15

CTC ATC GAG GAC GGT CTG GGC CC                                       71
Leu Ile Glu Asp Gly Leu Gly
                20
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:7:

| ACGGAGCTCA AGCAGTACCG | | | | | 20 |

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:8:

| GGGCCGAGAC CGTCCTCGA | | | | | 19 |

( 2 ) INFORMATION FOR SEQ ID NO:9:

( i ) SEQUENCE CHARACTERISTICS:
        ( A ) LENGTH: 2707 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Dactylosporangium sp.
        ( B ) STRAIN: RH1

( x i ) SEQUENCE DESCRIPTION: SEQ ID NO:9:

| GAGCTCTACC | GGCGAACGCG | CNCNCGGTGG | CCGAATACGA | NCCGGCGCCC | CACGATGTNC | 60 |
| GGGCCACCCT | CGTGCAGNCG | GCCGAGCAGG | ACGCGGGCT | ACGGCGGCG | NCGGTCGAGN | 120 |
| CGTGGACCCG | CGCCTGCGGG | GCGCCCCGN | CGGTGCATGT | GCTGCCGGGC | GGGCACTTCT | 180 |
| CGCTCTGCGC | CGGCCGCACG | TCGAGCGGCT | GGCCCGGCTC | CTGCCCGGCC | TGTAGGCGAC | 240 |
| CTAACCCACC | GTGAGGAGCG | CTCATGCTGA | CCCCGACGGA | GCTCAAGCAG | TACCGCGAGG | 300 |
| CGGGCTATCT | GCTCATCGAG | GACGGCCTCG | GCCCGCGGGA | GGTCGACTGC | CTGCGCCGGG | 360 |
| CGGCGGCGGC | CCTCTACGCG | CAGGACTCGC | CGGACCGCAC | GCTGGAGAAG | GACGGCCGCA | 420 |
| CCGTGCGCGC | GGTCCACGGC | TGCCACCGGC | GCGACCCGGT | CTGCCGCGAC | CTGGTCCGCC | 480 |
| ACCCGCGCCT | GCTGGGCCCG | GCGATGCAGA | TCCTGTCCGG | CGACGTGTAC | GTCCACCAGT | 540 |
| TCAAGATCAA | CGCGAAGGCC | CCGATGACCG | GCGATGTCTG | GCCGTGGCAC | CAGGACTACA | 600 |
| TCTTCTGGGC | CCGAGAGGAC | GGCATGGACC | GTCCGCACGT | GGTCAACGTC | GCGGTCCTGC | 660 |
| TCGACGAGGC | CACCCACCTC | AACGGGCCGC | TGTTGTTCGT | GCCGGGCACC | CACGAGCTGG | 720 |
| GCCTCATCGA | CGTGGAGCGC | CGCGCGCCGG | CCGGCGACGG | CGACGCGCAG | TGGCTGCCGC | 780 |
| AGCTCAGCGC | CGACCTCGAC | TACGCCATCG | ACGCCGACCT | GCTGGCCCGG | CTGACGGCCG | 840 |
| GGCGGGGCAT | CGAGTCGGCC | ACCGGCCCGG | CGGGCTCGAT | CCTGCTGTTC | GACTCCCGGA | 900 |
| TCGTGCACGG | CTCGGGCACG | AACATGTCGC | CGCACCCGCG | CGGCGTCGTC | CTGGTCACCT | 960 |
| ACAACCGCAC | CGACAACGCC | CTGCCGGCGC | AGGCCGCTCC | GCGCCCGGAG | TTCCTGGCCG | 1020 |
| CCCGCGACGC | CACCCCGCTG | GTGCCGCTGC | CCGCGGGCTT | CGCGCTGGCC | CAGCCCGTCT | 1080 |
| AGGCTGCCGC | AGGCGGCGCA | CGGCCCACCT | CAGCGCAGGC | CGAGCAGCCG | CCCCACGCCG | 1140 |
| GCGGCGAAGC | GGATCAGGCC | GCGCAGGCCG | AGCGGCGGGC | GAGGCGAGCA | TTGTCGGGCT | 1200 |
| GCCCAGTCGT | CGTGTCGTGG | GTGACAGCCC | GTGGCGGCTC | TTCTGACGGC | CCGCGACGGA | 1260 |
| TCACGGTCAT | GTTTGCCGAT | GGGACGTCAC | GGTCGTGTGC | CCGGACGGTC | GAAAATCACC | 1320 |
| AGAATGGTGC | TGATGGCCTG | TCGCGGGGTG | TCGGTGGTGC | GGTCGCCAGC | ATCCCTCGGC | 1380 |

| | | | | | |
|---|---|---|---|---|---|
|CGCGCCGGGG|CCGGTGCGTC|TCACCAGGCC|GTGCGGGCGT|TGACGGCCGA|GACGGCGGAC 1440|
|CGGAAGGCGG|CCACCGGTTC|GCCGAGATAG|CACCACGGGA|ACTCGGTGAC|CAACTCGCCG 1500|
|ATGGCCAGAA|ACTGCATCGC|CGCCGCCTCG|TCGTCGCCGG|CCGCCAGAAA|CGCGACCGCG 1560|
|AACGCGTTGG|CGTCCAGGGC|CCAGTCCGG|CGCCGCACAT|AGCGGCGGTG|CCGGACCGAC 1620|
|TCGCGGGCCG|CGTCGTTGAG|CGACTCCGC|ACCGCCGCCG|AGCGGATGTA|GTCACGGCTA 1680|
|GGCGCGCCAC|CGAGGTCCAG|CCAGTGTTCA|AGGTGCGCCA|GGGCGACGAG|CGTGCCAAGA 1740|
|CGGCTGCCCT|CGCCTGCGTC|CCGCGCGGCC|CCCTCGGCGA|ACGCGCGCAT|CCGCTCCGGC 1800|
|GAGCCGCCCC|ACTTCCGGCA|GAGGTTCTGC|AGCATCGCGG|TGTGGGCGCG|GTAGTTGTCC 1860|
|GGGTCATGCG|CGACCGCCGC|ATCGAACCGG|CGCCGCTGCT|CGTCCGCACT|CAGACCCAGG 1920|
|CCACGGGCGA|CGGTGATCAG|GCCAGTCCAG|GCCGTGACAT|TGGCCGGCTC|CCGGCGTACC 1980|
|ACCTCCTGCA|GGCAGTACTC|GGCGAGTTCC|AGCCGCTGCC|GGAACAGCAC|CCACGCTCAG 2040|
|GCGGGACGTA|CGCGGCAGGA|AGCCCGGTGC|GAGCCTCCCA|GGCCCACGCG|ATCGCCCGGT 2100|
|GACCGCGCAC|GAGCAGCGCC|AGGGGATCGT|CCGGCCCGTG|CTCGATTACA|TGCGCACAGC 2160|
|ACAGTGCTCG|GTGCCGGGA|CCTGGGCCGC|GACCGAGACC|AGGAAGTCGA|GATCCTCTCT 2220|
|TGTGCCGCTC|GGCGGCCAGN|ATGGGCCGCG|CGGNAAGCCA|GTCTCCGGCG|CCAACGCTG 2280|
|CCCACAGCCA|CCGGGCGTCG|GCATCACCGA|GCGTCGGGTC|GAAGGCGCGC|GCCACGCGCC 2340|
|CTGCGGACCG|CCGGAACAGG|GGCATGCGCG|CATCCTCCAG|CCGATGCGCC|GATCAGCCGG 2400|
|CGCGGCAAGA|TCGTACGCCC|GGACCGCGAG|GTCGGGAGGT|CCACGGGCGG|TCCCCACTGG 2460|
|GCGACGACTG|TCAGNTGCTA|CGCTGGCCCG|GTGGCCGAGA|TCACCGGGGC|GTTCGAGATC 2520|
|CATGTAACCG|TCGAGGCGCA|CCACGGCACG|GACCTCGCCC|GGTTCGCCGA|GAAGCACGAC 2580|
|GTCAAGTTCC|TGCACATCGT|CCTGGACCGC|GGCCGGTTTC|CGTCCCAGCC|GATCTCACGC 2640|
|TGCCGATGCA|CGGCACCCTC|GCTCAGGCAC|GGAAGACGGC|GCCACGTGGC|GGGAGCGGCT 2700|
|ACTCGAG| | | | |2707|

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:10:

GTGAGGAAAG CTTATGCTGA CCCCGACGGA GCTCAAG                                37

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:11:

GCCTGCGGGA TCCTAGACGG GCTGGGCCAG CGCGAA                                  36

( 2 ) INFORMATION FOR SEQ ID NO:12:

( i ) SEQUENCE CHARACTERISTICS:

( A ) LENGTH: 37 base pairs
( B ) TYPE: nucleic acid
( C ) STRANDEDNESS: single
( D ) TOPOLOGY: linear ( i i ) MOLECULE TYPE: other nucleic acid, synthetic DNA ( x i ) SEQUENCE DESCRIPTION: SEQ ID NO:12:

GTGAGGAGAA TTCATGCTGA CCCCGACGGA GCTCAAG     37

( 2 ) INFORMATION FOR SEQ ID NO:13:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: other nucleic acid, synthetic DNA ( x i ) SEQUENCE DESCRIPTION: SEQ ID NO:13:

CCGCCTGAAG CTTCCTAGAC GGGCTGGGCC AGCGCGAA     38

( 2 ) INFORMATION FOR SEQ ID NO:14:

( i ) SEQUENCE CHARACTERISTICS:
( A ) LENGTH: 64 base pairs
( B ) TYPE: nucleic acid
( C ) STRANDEDNESS: single
( D ) TOPOLOGY: linear ( i i ) MOLECULE TYPE: other nucleic acid, synthetic DNA ( x i ) SEQUENCE DESCRIPTION: SEQ ID NO:14:

TGAGGAAAGC TTATGCTGAC CCCGACCGAA CTGAAACAGT ATCGTGAAGC     50

GGGCTATCTG CTGA     64

( 2 ) INFORMATION FOR SEQ ID NO:15:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: other nucleic acid, synthetic DNA ( x i ) SEQUENCE DESCRIPTION: SEQ ID NO:15:

CCGGAATTCG TCGACTTCAC GCGGGCCCAG GCCATCTTCA ATCAGCAGAT     50

AGCCCGCTTC ACGATA     66

( 2 ) INFORMATION FOR SEQ ID NO:16:

( i ) SEQUENCE CHARACTERISTICS:
( A ) LENGTH: 816 base pairs
( B ) TYPE: nucleic acid
( C ) STRANDEDNESS: double
( D ) TOPOLOGY: linear ( i i ) MOLECULE TYPE: other nucleic acid ( x i ) SEQUENCE DESCRIPTION: SEQ ID NO:16:

```
ATG  CTG  ACC  CCG  ACC  GAA  CTG  AAA  CAG  TAT  CGT  GAA  GCG  GGC  TAT  CTG        48
Met  Leu  Thr  Pro  Thr  Glu  Leu  Lys  Gln  Tyr  Arg  Glu  Ala  Gly  Tyr  Leu
 1             5                        10                       15

CTG  ATT  GAA  GAT  GGC  CTG  GGC  CCG  CGT  GAA  GTC  GAC  TGC  CTG  CGC  CGG        96
Leu  Ile  Glu  Asp  Gly  Leu  Gly  Pro  Arg  Glu  Val  Asp  Cys  Leu  Arg  Arg
         20                       25                       30
```

```
GCG  GCG  GCG  GCC  CTC  TAC  GCG  CAG  GAC  TCG  CCG  GAC  CGC  ACG  CTG  GAG    144
Ala  Ala  Ala  Ala  Leu  Tyr  Ala  Gln  Asp  Ser  Pro  Asp  Arg  Thr  Leu  Glu
               35                    40                    45

AAG  GAC  GGC  CGC  ACC  GTG  CGC  GCG  GTC  CAC  GGC  TGC  CAC  CGG  CGC  GAC    192
Lys  Asp  Gly  Arg  Thr  Val  Arg  Ala  Val  His  Gly  Cys  His  Arg  Arg  Asp
          50                         55                    60

CCG  GTC  TGC  CGC  GAC  CTG  GTC  CGC  CAC  CCG  CGC  CTG  CTG  GGC  CCG  GCG    240
Pro  Val  Cys  Arg  Asp  Leu  Val  Arg  His  Pro  Arg  Leu  Leu  Gly  Pro  Ala
65                        70                        75                         80

ATG  CAG  ATC  CTG  TCC  GGC  GAC  GTG  TAC  GTC  CAC  CAG  TTC  AAG  ATC  AAC    288
Met  Gln  Ile  Leu  Ser  Gly  Asp  Val  Tyr  Val  His  Gln  Phe  Lys  Ile  Asn
                    85                        90                         95

GCG  AAG  GCC  CCG  ATG  ACC  GGC  GAT  GTC  TGG  CCG  TGG  CAC  CAG  GAC  TAC    336
Ala  Lys  Ala  Pro  Met  Thr  Gly  Asp  Val  Trp  Pro  Trp  His  Gln  Asp  Tyr
               100                       105                       110

ATC  TTC  TGG  GCC  CGA  GAG  GAC  GGC  ATG  GAC  CGT  CCG  CAC  GTG  GTC  AAC    384
Ile  Phe  Trp  Ala  Arg  Glu  Asp  Gly  Met  Asp  Arg  Pro  His  Val  Val  Asn
          115                       120                       125

GTC  GCG  GTC  CTG  CTC  GAC  GAG  GCC  ACC  CAC  CTC  AAC  GGG  CCG  CTG  TTG    432
Val  Ala  Val  Leu  Leu  Asp  Glu  Ala  Thr  His  Leu  Asn  Gly  Pro  Leu  Leu
     130                       135                       140

TTC  GTG  CCG  GGC  ACC  CAC  GAG  CTG  GGC  CTC  ATC  GAC  GTG  GAG  CGC  CGC    480
Phe  Val  Pro  Gly  Thr  His  Glu  Leu  Gly  Leu  Ile  Asp  Val  Glu  Arg  Arg
145                       150                       155                       160

GCG  CCG  GCC  GGC  GAC  GGC  GAC  GCG  CAG  TGG  CTG  CCG  CAG  CTC  AGC  GCC    528
Ala  Pro  Ala  Gly  Asp  Gly  Asp  Ala  Gln  Trp  Leu  Pro  Gln  Leu  Ser  Ala
                    165                       170                       175

GAC  CTC  GAC  TAC  GCC  ATC  GAC  GCC  GAC  CTG  CTG  GCC  CGG  CTG  ACG  GCC    576
Asp  Leu  Asp  Tyr  Ala  Ile  Asp  Ala  Asp  Leu  Leu  Ala  Arg  Leu  Thr  Ala
               180                       185                       190

GGG  CGG  GGC  ATC  GAG  TCG  GCC  ACC  GGC  CCG  GCG  GGC  TCG  ATC  CTG  CTG    624
Gly  Arg  Gly  Ile  Glu  Ser  Ala  Thr  Gly  Pro  Ala  Gly  Ser  Ile  Leu  Leu
          195                       200                       205

TTC  GAC  TCC  CGG  ATC  GTG  CAC  GGC  TCG  GGC  ACG  AAC  ATG  TCG  CCG  CAC    672
Phe  Asp  Ser  Arg  Ile  Val  His  Gly  Ser  Gly  Thr  Asn  Met  Ser  Pro  His
     210                       215                       220

CCG  CGC  GGC  GTC  GTC  CTG  GTC  ACC  TAC  AAC  CGC  ACC  GAC  AAC  GCC  CTG    720
Pro  Arg  Gly  Val  Val  Leu  Val  Thr  Tyr  Asn  Arg  Thr  Asp  Asn  Ala  Leu
225                       230                       235                       240

CCG  GCG  CAG  GCC  GCT  CCG  CGC  CCG  GAG  TTC  CTG  GCC  GCC  CGC  GAC  GCC    768
Pro  Ala  Gln  Ala  Ala  Pro  Arg  Pro  Glu  Phe  Leu  Ala  Ala  Arg  Asp  Ala
                    245                       250                       255

ACC  CCG  CTG  GTG  CCG  CTG  CCC  GCG  GGC  TTC  GCG  CTG  GCC  CAG  CCC  GTC    816
Thr  Pro  Leu  Val  Pro  Leu  Pro  Ala  Gly  Phe  Ala  Leu  Ala  Gln  Pro  Val
               260                       265                       270
```

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:17:

AAGCAGTACC GCGAGGCGGG        20

( 2 ) INFORMATION FOR SEQ ID NO:18:

( i ) SEQUENCE CHARACTERISTICS:

( A ) LENGTH: 21 base pairs
( B ) TYPE: nucleic acid
( C ) STRANDEDNESS: single
( D ) TOPOLOGY: linear ( i i ) MOLECULE TYPE: other nucleic acid, synthetic DNA ( x i ) SEQUENCE DESCRIPTION: SEQ ID NO:18:

ATGCTGACCC CGACGGAGCT C    21

( 2 ) INFORMATION FOR SEQ ID NO:19:

( i ) SEQUENCE CHARACTERISTICS:
( A ) LENGTH: 299 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Dactylosporangium sp.
( B ) STRAIN: RH1

( i x ) FEATURE:
( A ) NAME/KEY: peptide
( B ) LOCATION: 35 to 299
( C ) IDENTIFICATION METHOD: by similarity with known sequence
or to an established consensus ( v i ) ORIGINAL SOURCE:
( A ) ORGANISM: Escherichia coli ( v i i ) IMMEDIATE SOURCE: pBluescriptIIKS+

( i x ) FEATURE:
( A ) NAME/KEY: peptide
( B ) LOCATION: 1 to 34
( C ) IDENTIFICATION METHOD: by similarity with known sequence
or to an established consensus ( x i ) SEQUENCE DESCRIPTION: SEQ ID NO:19:

```
Met Thr Met Ile Thr Pro Ser Ala Gln Leu Thr Leu Thr Lys Gly Asn
 1           5                  10                  15

Lys Ser Trp Val Pro Gly Pro Pro Ser Arg Ser Thr Val Ser Ile Ser
             20                  25                  30

Leu Ile Lys Gln Tyr Arg Glu Ala Gly Tyr Leu Leu Ile Glu Asp Gly
         35                  40                  45

Leu Gly Pro Arg Glu Val Asp Cys Leu Arg Arg Ala Ala Ala Ala Leu
     50                  55                  60

Tyr Ala Gln Asp Ser Pro Asp Arg Thr Leu Glu Lys Asp Gly Arg Thr
 65                  70                  75                  80

Val Arg Ala Val His Gly Cys His Arg Arg Asp Pro Val Cys Arg Asp
                 85                  90                  95

Leu Val Arg His Pro Arg Leu Leu Gly Pro Ala Met Gln Ile Leu Ser
                100                 105                 110

Gly Asp Val Tyr Val His Gln Phe Lys Ile Asn Ala Lys Ala Pro Met
             115                 120                 125

Thr Gly Asp Val Trp Pro Trp His Gln Asp Tyr Ile Phe Trp Ala Arg
     130                 135                 140

Glu Asp Gly Met Asp Arg Pro His Val Val Asn Val Ala Val Leu Leu
145                 150                 155                 160

Asp Glu Ala Thr His Leu Asn Gly Pro Leu Leu Phe Val Pro Gly Thr
                 165                 170                 175

His Glu Leu Gly Leu Ile Asp Val Glu Arg Arg Ala Pro Ala Gly Asp
                 180                 185                 190
```

Gly Asp Ala Gln Trp Leu Pro Gln Leu Ser Ala Asp Leu Asp Tyr Ala
              195                 200                 205

Ile Asp Ala Asp Leu Leu Ala Arg Leu Thr Ala Gly Arg Gly Ile Glu
        210             215                 220

Ser Ala Thr Gly Pro Ala Gly Ser Ile Leu Leu Phe Asp Ser Arg Ile
225             230                 235                         240

Val His Gly Ser Gly Thr Asn Met Ser Pro His Pro Arg Gly Val Val
                245                 250                 255

Leu Val Thr Tyr Asn Arg Thr Asp Asn Ala Leu Pro Ala Gln Ala Ala
                260             265                 270

Pro Arg Pro Glu Phe Leu Ala Ala Arg Asp Ala Thr Pro Leu Val Pro
        275                 280                 285

Leu Pro Ala Gly Phe Ala Leu Ala Gln Pro Val
    290                 295

( 2 ) INFORMATION FOR SEQ ID NO:20:

( i ) SEQUENCE CHARACTERISTICS:
        ( A ) LENGTH: 659 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Dactylosporangium sp.
        ( B ) STRAIN: RH1

( i x ) FEATURE:
        ( A ) NAME/KEY: peptide
        ( B ) LOCATION: 389 to 659
        ( C ) IDENTIFICATION METHOD: by experiment ( v i ) ORIGINAL SOURCE:
        ( A ) ORGANISM: Escherichia coli ( v i i ) IMMEDIATE SOURCE: pMAL-c2

( i x ) FEATURE:
        ( A ) NAME/KEY: peptide
        ( B ) LOCATION: 1 to 387
        ( C ) IDENTIFICATION METHOD: by similarity with known sequence
            or to an established consensus ( x i ) SEQUENCE DESCRIPTION: SEQ ID NO:20:

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly

```
                                130                              135                              140
Lys   Ser   Ala   Leu   Met   Phe   Asn   Leu   Gln   Glu   Pro   Tyr   Phe   Thr   Trp   Pro
145                           150                             155                             160

Leu   Ile   Ala   Ala   Asp   Gly   Gly   Tyr   Ala   Phe   Lys   Tyr   Glu   Asn   Gly   Lys
                        165                           170                           175

Tyr   Asp   Ile   Lys   Asp   Val   Gly   Val   Asp   Asn   Ala   Gly   Ala   Lys   Ala   Gly
                  180                           185                           190

Leu   Thr   Phe   Leu   Val   Asp   Leu   Ile   Lys   Asn   Lys   His   Met   Asn   Ala   Asp
            195                           200                           205

Thr   Asp   Tyr   Ser   Ile   Ala   Glu   Ala   Ala   Phe   Asn   Lys   Gly   Glu   Thr   Ala
      210                           215                           220

Met   Thr   Ile   Asn   Gly   Pro   Trp   Ala   Trp   Ser   Asn   Ile   Asp   Thr   Ser   Lys
225                           230                           235                             240

Val   Asn   Tyr   Gly   Val   Thr   Val   Leu   Pro   Thr   Phe   Lys   Gly   Gln   Pro   Ser
                        245                           250                           255

Lys   Pro   Phe   Val   Gly   Val   Leu   Ser   Ala   Gly   Ile   Asn   Ala   Ala   Ser   Pro
                        260                           265                           270

Asn   Lys   Glu   Leu   Ala   Lys   Glu   Phe   Leu   Glu   Asn   Tyr   Leu   Leu   Thr   Asp
            275                           280                           285

Glu   Gly   Leu   Glu   Ala   Val   Asn   Lys   Asp   Lys   Pro   Leu   Gly   Ala   Val   Ala
      290                           295                           300

Leu   Lys   Ser   Tyr   Glu   Glu   Leu   Ala   Lys   Asp   Pro   Arg   Ile   Ala   Ala
305                           310                           315                             320

Thr   Met   Glu   Asn   Ala   Gln   Lys   Gly   Glu   Ile   Met   Pro   Asn   Ile   Pro   Gln
                        325                           330                           335

Met   Ser   Ala   Phe   Trp   Tyr   Ala   Val   Arg   Thr   Ala   Val   Ile   Asn   Ala   Ala
                  340                           345                           350

Ser   Gly   Arg   Gln   Thr   Val   Asp   Glu   Ala   Leu   Lys   Asp   Ala   Gln   Thr   Asn
            355                           360                           365

Ser   Ser   Ser   Asn   Asn   Asn   Asn   Asn   Asn   Asn   Asn   Asn   Asn   Leu   Gly   Ile
      370                           375                           380

Glu   Gly   Arg   Met   Leu   Thr   Pro   Thr   Glu   Leu   Lys   Gln   Tyr   Arg   Glu   Ala
385                           390                           395                             400

Gly   Tyr   Leu   Leu   Ile   Glu   Asp   Gly   Leu   Gly   Pro   Arg   Glu   Val   Asp   Cys
                        405                           410                           415

Leu   Arg   Arg   Ala   Ala   Ala   Ala   Leu   Tyr   Ala   Gln   Asp   Ser   Pro   Asp   Arg
                  420                           425                           430

Thr   Leu   Glu   Lys   Asp   Gly   Arg   Thr   Val   Arg   Ala   Val   His   Gly   Cys   His
            435                           440                           445

Arg   Arg   Asp   Pro   Val   Cys   Arg   Asp   Leu   Val   Arg   His   Pro   Arg   Leu   Leu
450                           455                           460

Gly   Pro   Ala   Met   Gln   Ile   Leu   Ser   Gly   Asp   Val   Tyr   Val   His   Gln   Phe
465                           470                           475                             480

Lys   Ile   Asn   Ala   Lys   Ala   Pro   Met   Thr   Gly   Asp   Val   Trp   Pro   Trp   His
                        485                           490                           495

Gln   Asp   Tyr   Ile   Phe   Trp   Ala   Arg   Glu   Asp   Gly   Met   Asp   Arg   Pro   His
                  500                           505                           510

Val   Val   Asn   Val   Ala   Val   Leu   Leu   Asp   Glu   Ala   Thr   His   Leu   Asn   Gly
            515                           520                           525

Pro   Leu   Leu   Phe   Val   Pro   Gly   Thr   His   Glu   Leu   Gly   Leu   Ile   Asp   Val
      530                           535                           540

Glu   Arg   Arg   Ala   Pro   Ala   Gly   Asp   Gly   Asp   Ala   Gln   Trp   Leu   Pro   Gln
545                           550                           555                             560
```

| Leu | Ser | Ala | Asp | Leu<br>565 | Asp | Tyr | Ala | Ile | Asp<br>570 | Ala | Asp | Leu | Leu | Ala<br>575 | Arg |
|---|---|---|---|---|---|---|---|---|---|---|---|---|---|---|---|
| Leu | Thr | Ala | Gly<br>580 | Arg | Gly | Ile | Glu | Ser<br>585 | Ala | Thr | Gly | Pro | Ala<br>590 | Gly | Ser |
| Ile | Leu | Leu<br>595 | Phe | Asp | Ser | Arg | Ile<br>600 | Val | His | Gly | Ser | Gly<br>605 | Thr | Asn | Met |
| Ser | Pro<br>610 | His | Pro | Arg | Gly | Val<br>615 | Val | Leu | Val | Thr | Tyr<br>620 | Asn | Arg | Thr | Asp |
| Asn<br>625 | Ala | Leu | Pro | Ala | Gln<br>630 | Ala | Ala | Pro | Arg | Pro<br>635 | Glu | Phe | Leu | Ala | Ala<br>640 |
| Arg | Asp | Ala | Thr | Pro<br>645 | Leu | Val | Pro | Leu | Pro<br>650 | Ala | Gly | Phe | Ala | Leu<br>655 | Ala |
| Gln | Pro | Val | | | | | | | | | | | | | |

( 2 ) INFORMATION FOR SEQ ID NO:21:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid, synthetic DNA ( x i ) SEQUENCE DESCRIPTION: SEQ ID NO:21:

GACCCGTGCT AATATGGAAG AC                       22

( 2 ) INFORMATION FOR SEQ ID NO:22:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid, synthetic DNA ( x i ) SEQUENCE DESCRIPTION: SEQ ID NO:22:

GTCTTCCATA TTAGCACGGG TC                       22

( 2 ) INFORMATION FOR SEQ ID NO:23:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid, synthetic DNA ( x i ) SEQUENCE DESCRIPTION: SEQ ID NO:23:

GGCAAAGCTT CATGAGTGAC AGCCAGACGC TGG                33

( 2 ) INFORMATION FOR SEQ ID NO:24:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid, synthetic DNA ( x i ) SEQUENCE DESCRIPTION: SEQ ID NO:24:

TTTGCAGGAT CCGGTTTTAT TTACGCACGA ATG                33

( 2 ) INFORMATION FOR SEQ ID NO:25:

( i ) SEQUENCE CHARACTERISTICS:
        ( A ) LENGTH: 1125 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:25:

```
ATG ACC ATG ATT ACG CCA AGC TTC ATG AGT GAC AGC CAG ACG CTG GTG        48
Met Thr Met Ile Thr Pro Ser Phe Met Ser Asp Ser Gln Thr Leu Val
 1               5                  10                  15

GTA AAA CTC GGC ACC AGT GTG CTA ACA GGC GGA TCG CGC CGT CTG AAC        96
Val Lys Leu Gly Thr Ser Val Leu Thr Gly Gly Ser Arg Arg Leu Asn
                20                  25                  30

CGT GCC CAT ATC GTT GAA CTT GTT CGC CAG TGC GCG CAG TTA CAT GCC       144
Arg Ala His Ile Val Glu Leu Val Arg Gln Cys Ala Gln Leu His Ala
             35                  40                  45

GCC GGG CAT CGG ATT GTT ATT GTG ACG TCG GGC GCG ATC GCC GCC GGA       192
Ala Gly His Arg Ile Val Ile Val Thr Ser Gly Ala Ile Ala Ala Gly
         50                  55                  60

CGT GAG CAC CTG GGT TAC CCG GAA CTG CCA GCG ACC ATC GCC TCG AAA       240
Arg Glu His Leu Gly Tyr Pro Glu Leu Pro Ala Thr Ile Ala Ser Lys
 65                  70                  75                  80

CAA CTG CTG GCG GCG GTA GGG CAG AGT CGA CTG ATT CAA CTG TGG GAA       288
Gln Leu Leu Ala Ala Val Gly Gln Ser Arg Leu Ile Gln Leu Trp Glu
                 85                  90                  95

CAG CTG TTT TCG ATT TAT GGC ATT CAC GTC GGG CAA ATG CTG CTG ACC       336
Gln Leu Phe Ser Ile Tyr Gly Ile His Val Gly Gln Met Leu Leu Thr
                100                 105                 110

CGT GCT AAT ATG GAA GAC CGT GAA CGC TTC CTG AAC GCC CGC GAC ACC       384
Arg Ala Asn Met Glu Asp Arg Glu Arg Phe Leu Asn Ala Arg Asp Thr
            115                 120                 125

CTG CGA GCG TTG CTC GAT AAC AAT ATC GTT CCG GTA ATC AAT GAG AAC       432
Leu Arg Ala Leu Leu Asp Asn Asn Ile Val Pro Val Ile Asn Glu Asn
        130                 135                 140

GAT GCT GTC GCT ACG GCA GCG ATT AAG GTC GGC GAT AAC GAT AAC CTT       480
Asp Ala Val Ala Thr Ala Ala Ile Lys Val Gly Asp Asn Asp Asn Leu
145                 150                 155                 160

TCT GCG CTG GCG GCG ATT CTT GCG GGT GCC GAT AAA CTG TTG CTG CTG       528
Ser Ala Leu Ala Ala Ile Leu Ala Gly Ala Asp Lys Leu Leu Leu Leu
                165                 170                 175

ACC GAT CAA AAA GGT TTG TAT ACC GCT GAC CCG CGC AGC AAT CCG CAG       576
Thr Asp Gln Lys Gly Leu Tyr Thr Ala Asp Pro Arg Ser Asn Pro Gln
                180                 185                 190

GCA GAA CTG ATT AAA GAT GTT TAC GGC ATT GAT GAC GCA CTG CGC GCG       624
Ala Glu Leu Ile Lys Asp Val Tyr Gly Ile Asp Asp Ala Leu Arg Ala
            195                 200                 205

ATT GCC GGT GAC AGC GTT TCA GGC CTC GGA ACT GGC GGC ATG AGT ACC       672
Ile Ala Gly Asp Ser Val Ser Gly Leu Gly Thr Gly Gly Met Ser Thr
        210                 215                 220

AAA TTG CAG GCC GCT GAC GTG GCT TGC CGT GCG GGT ATC GAC ACC ATT       720
Lys Leu Gln Ala Ala Asp Val Ala Cys Arg Ala Gly Ile Asp Thr Ile
225                 230                 235                 240

ATT GCC GCG GGC AGC AAG CCG GGC GTT ATT GGT GAT GTG ATG GAA GGC       768
Ile Ala Ala Gly Ser Lys Pro Gly Val Ile Gly Asp Val Met Glu Gly
                245                 250                 255

ATT TCC GTC GGT ACG CTG TTC CAT GCC CAG GCG ACT CCG CTT GAA AAC       816
Ile Ser Val Gly Thr Leu Phe His Ala Gln Ala Thr Pro Leu Glu Asn
                260                 265                 270
```

-continued

| | | | | | | | | | | | | | | | | |
|---|---|---|---|---|---|---|---|---|---|---|---|---|---|---|---|---|
| CGT | AAA | CGC | TGG | ATT | TTC | GGT | GCG | CCG | CCG | GCG | GGT | GAA | ATC | ACG | GTA | 864 |
| Arg | Lys | Arg | Trp | Ile | Phe | Gly | Ala | Pro | Pro | Ala | Gly | Glu | Ile | Thr | Val | |
| | | 275 | | | | | 280 | | | | | 285 | | | | |
| GAT | GAA | GGG | GCA | ACT | GCC | GCC | ATT | CTG | GAA | CGC | GGC | AGC | TCC | CTG | TTG | 912 |
| Asp | Glu | Gly | Ala | Thr | Ala | Ala | Ile | Leu | Glu | Arg | Gly | Ser | Ser | Leu | Leu | |
| | 290 | | | | | 295 | | | | | 300 | | | | | |
| CCG | AAA | GGC | ATT | AAA | AGC | GTG | ACT | GGC | AAT | TTC | TCG | CGT | GGT | GAA | GTC | 960 |
| Pro | Lys | Gly | Ile | Lys | Ser | Val | Thr | Gly | Asn | Phe | Ser | Arg | Gly | Glu | Val | |
| 305 | | | | | 310 | | | | | 315 | | | | | 320 | |
| ATC | CGC | ATT | TGC | AAC | CTC | GAA | GGC | CGC | GAT | ATC | GCC | CAC | GGC | GTC | AGT | 1008 |
| Ile | Arg | Ile | Cys | Asn | Leu | Glu | Gly | Arg | Asp | Ile | Ala | His | Gly | Val | Ser | |
| | | | | 325 | | | | | 330 | | | | | 335 | | |
| CGT | TAC | AAC | AGC | GAT | GCA | TTA | CGC | CGT | ATT | GCC | GGA | CAC | CAC | TCG | CAA | 1056 |
| Arg | Tyr | Asn | Ser | Asp | Ala | Leu | Arg | Arg | Ile | Ala | Gly | His | His | Ser | Gln | |
| | | | 340 | | | | | 345 | | | | | 350 | | | |
| GAA | ATT | GAT | GCA | ATA | CTG | GGA | TAT | GAA | TAC | GGC | CCG | GTT | GCC | GTT | CAC | 1104 |
| Glu | Ile | Asp | Ala | Ile | Leu | Gly | Tyr | Glu | Tyr | Gly | Pro | Val | Ala | Val | His | |
| | | 355 | | | | | 360 | | | | | 365 | | | | |
| CGT | GAT | GAC | ATG | ATT | ACC | CGT | | | | | | | | | | 1125 |
| Arg | Asp | Asp | Met | Ile | Thr | Arg | | | | | | | | | | |
| | 370 | | | | | 375 | | | | | | | | | | |

( 2 ) INFORMATION FOR SEQ ID NO:26:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:26:

TATCGATAAG CTTATGCTGA CCCCGACCGA ACTGAAA        37

( 2 ) INFORMATION FOR SEQ ID NO:27:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:27:

GGCAGAATTC TAGACGGGCT GGGCCAGCGC GAA        33

( 2 ) INFORMATION FOR SEQ ID NO:28:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:28:

AAAATTGAAT TCCAGAGAAT CATGAGTGAC AGCCAGAC        38

( 2 ) INFORMATION FOR SEQ ID NO:29:

( i ) SEQUENCE CHARACTERISTICS:
        ( A ) LENGTH: 36 base pairs
        ( B ) TYPE: nucleic acid.

( C ) STRANDEDNESS: single
( D ) TOPOLOGY: linear ( i i ) MOLECULE TYPE: other nucleic acid, synthetic DNA ( x i ) SEQUENCE DESCRIPTION: SEQ ID NO:29:

ACCCGGATCC ATTTACGCAC GAATGGTGTA ATCACC 36

PROCESS FOR PRODUCING TRANS-4-HYDROXY-L-PROLINE

This application is a continuation-in-part of Ser. No. 08/482,554, filed Jun. 7, 1995 now abandoned which is a continuation-in-part of Ser. No. 08/301,653, filed Sep. 7, 1994 now abandoned.

FIELD OF THE INVENTION

The present invention relates to a process for producing trans-4-hydroxy-L-proline. Trans-4-hydroxy-L-proline is useful as a starting compound for medicines and an additive to foods. The present invention also relates to a novel enzyme capable of catalyzing the hydroxylation of L-proline at the 4-position of L-proline (hereinafter referred to as L-proline-4-hydroxylase). The novel enzyme is used in the above-mentioned process.

The present invention also relates to a process for industrially producing trans-4-hydroxy-L-proline, a gene encoding a protein having an activity of L-proline-4-hydroxylase (hereinafter referred to as "L-proline-4-hydroxylase gene") which is useful for the above-mentioned process, a transformant containing the gene, and a process for producing L-proline-4-hydroxylase using the transformant.

In addition, this invention relates to a process for industrially producing trans-4-hydroxy-L-proline using a transformant which contains L-proline-4-hydroxylase gene and has a reinforced proline biosynthesis activity.

BACKGROUND OF THE INVENTION

The following processes are known as a method for producing trans-4-hydroxy-L-proline using microorganisms.

1) A process in which trans-4-hydroxy-L-proline is produced from 4-hydroxy-2-oxoglutaric acid using microorganisms of the genus Escherichia (Japanese Published Unexamined Patent Application No. 266,995/91)

2) A process in which trans-4-hydroxy-L-proline is produced directly through fermentation using bacteria or fungi (EP 0 547 898 A2, and Japanese Published Unexamined Patent Application Nos. 236,980/93 and 245,782/94)

3) A process in which trans-4-hydroxy-L-proline is produced from L-proline using microorganisms of the genus Streptomvces [J. Biol. Chem., 254, 6684 (1979), Biochem. Biophys. Res. Comm., 120, 45, (1984), Tetrahedron Letters, 34, 7489 (1993), and Tetrahedron Letters, 35, 4649 (1994)].

The conventional processes can, however, hardly be performed on an industrial scale for the following reasons:

1) A substrate for producing trans-4-hydroxy-L-proline, such as 4-hydroxy-2-oxoglutaric acid is too expensive and is difficult to obtain.

2) The productivity of trans-4-hydroxy-L-proline is low.

3) The activity of the enzymes that relate to the production of trans-4-hydroxy-L-proline is quite weak.

Heretofore, L-proline-4-hydroxylase has not been isolated. A process for producing trans-4-hydroxy-L-proline, using an enzyme source which is isolated from a microorganism belonging to the genus Dactylosporangium or Amycolatopsis and which catalyzes the hydroxylation of L-proline into trans-4-hydroxy-L-proline, has not been known. Although there was a paper reporting that L-proline-4-hydroxylase was isolated from a microorganism belonging to the genus Streptomyces (Tetrahedron Letters, 34, 7489–7492, 1993), the report is silent about steps for isolating the enzyme, the enzyme purity, the physicochemical properties of the enzyme, etc.

With respect to the enzyme that catalyzes the production of trans-4-hydroxy-L-proline, it was reported in a paper that L-proline-4-hydroxylase is purified from a microorganism of the genus Streptomyces. However, a method for obtaining the enzyme and physicochemical properties of the enzyme are not described therein. Further, no paper reported that a gene encoding L-proline-4-hydroxylase having the activity of converting free L-proline into trans-4-hydroxy-L-proline in the presence of 2-ketoglutaric acid and a divalent iron ion had been cloned.

A process in which trans-4-hydroxy-L-proline is produced industrially advantageously using L-proline-4-hydroxylase having a high level of activity has been in demand.

The object of the present invention is to provide an efficient process for the production of trans-4-hydroxy-L-proline on the industrially applicable basis, and the additional object of the present invention is to provide a novel enzyme which catalyzes the hydroxylation of L-proline at the 4-position of L-proline and which is useful in the above process.

SUMMARY OF THE INVENTION

The present invention provides a process for the production of trans-4-hydroxy-L-proline which comprises allowing L-proline to coexist with 2-ketoglutaric acid, a divalent iron ion and an enzyme source which catalyzes hydroxylation of L-proline at the 4-position of L-proline in an aqueous medium to convert L-proline into trans-4-hydroxy-L-proline, and recovering the trans-4-hydroxy-L-proline from the aqueous medium.

The present invention further provides a novel hydroxylase (L-proline-4-hydroxylase) having the following physicochemical properties:

(1) Action and Substrate Specificity:

The enzyme catalyzes hydroxylation of L-proline at the 4-position of L-proline in the presence of 2-ketoglutaric acid and a divalent iron ion to produce trans-4-hydroxy-L-proline.

(2) optimum pH Range:

The enzyme has an optimum pH range of 6.0 to 7.0 for its reaction at 30° C. for 20 minutes.

(3) Stable pH Range:

The enzyme is stable at pH values of 6.5 to 10.0, when it is allowed to stand at 4° C. for 24 hours.

(4) Optimum Temperature Range:

The optimum temperature range is 30° to 40° C. when it is allowed to stand at pH 6.5 for 15 minutes.

(5) Stable Temperature Range:

The enzyme is inactivated, when it is allowed to stand at pH 9.0 and at 50° C. for 30 minutes.

(6) Inhibitors:

The activity of the enzyme is inhibited by metal ions of $Zn^{++}$ and $Cu^{++}$ and ethylenediaminetetraacetic acid.

(7) Activation:

The enzyme does not need any cofactors for its activation. L-Ascorbic acid accelerates the activity of the enzyme.

(8) Km Value:

Km value is 0.27 mM for L-proline and is 0.55 mM for 2-ketoglutaric acid, when determined in a 80 mM 2-(N- morpholino)ethanesulfonic acid (MES) buffer (pH 6.5) containing 4 mM L-ascorbic acid, 2 mM ferrous sulfate and the enzyme preparation.

(9) Molecular Weight:

The enzyme has a molecular weight of 32,000±5,000 daltons by sodium dodecylsulfate-polyacrylamide gel electrophoresis and of 43,800±5,000 daltons by gel filtration.

(10) N-terminal Amino Acid Sequence:

The enzyme has an N-terminal amino acid sequence illustrated by Sequence No. 1 mentioned below.

Sequence No. 1:

| (N-terminal) | 1 | MetLeuThrProThrGluLeuLysGlnTyr |
|---|---|---|
| | 11 | ArgGluAlaGlyTyrLeuLeuIleGluAsp |
| | 21 | GlyLeuGlyProArgGluVal |

The present invention also provides an L-proline-4-hydroxylase gene and a transformant containing the above-mentioned gene for producing trans-4-hydroxy-L-proline efficiently and industrially advantageously using L-proline-4-hydroxylase from L-proline that is available at low cost, a process for mass-producing the L-proline-4-hydroxylase using the gene and the transformant, and a process for producing trans-4-hydroxy-L-proline industrially at low cost using the transformant or the L-proline-4-hydroxylase.

In addition, the present invention provides a transformant, hich contains the above-mentioned gene for producing trans-4-hydroxy-L-proline and has reinforced proline biosynthesis activity, and a process for producing trans-4-hydroxy-L-proline using the transformant industrially at low cost.

In the figure, the thick, shadowed lines each indicate a cloned Dactylosporangium sp. RH1 chromosome site. Ap indicates a pBR322-derived ampicillin-resistant gene. In the figure, only the restriction enzyme sites having relation to the construction of the plasmids are shown.

Figure 2:
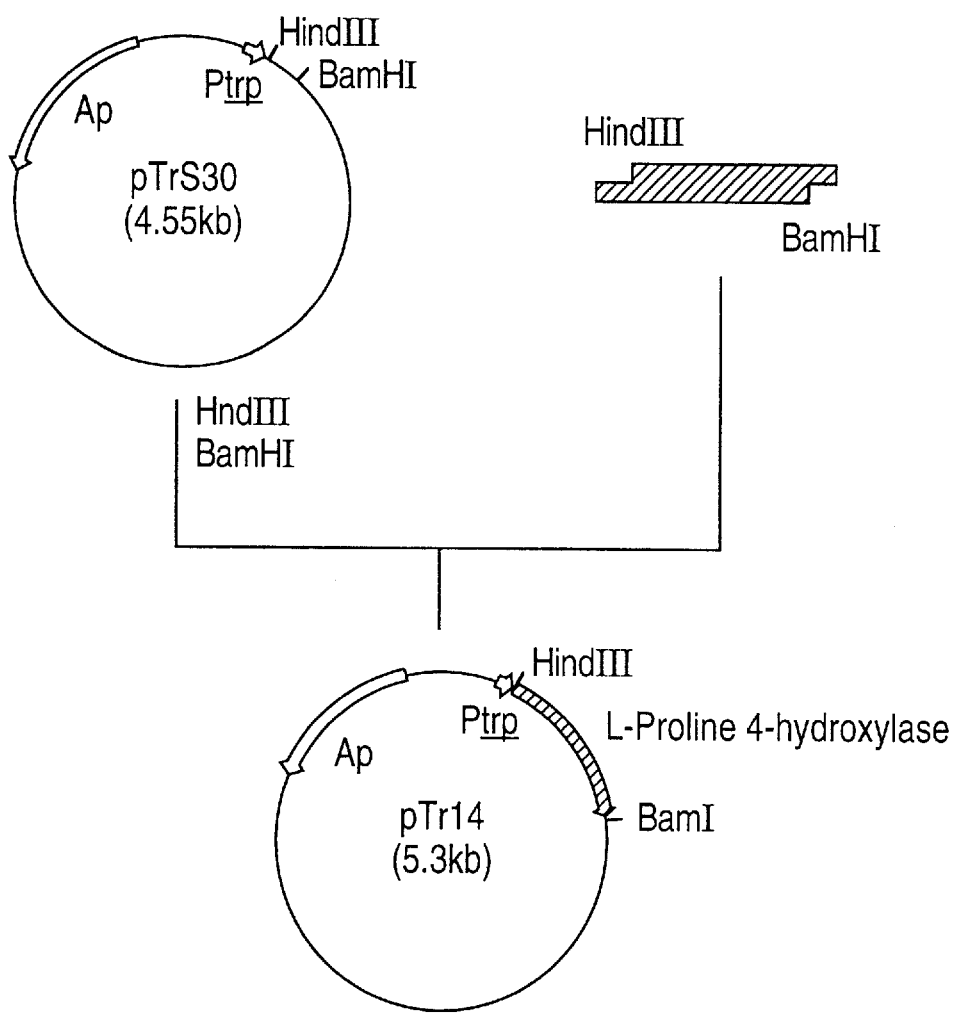

FIG. 2 shows the steps of constructing plasmid pTr14.

In the figure, the thick, solid black lines each indicate a part that contains an L-proline 4-hydroxylase gene. Ap indicates a pBR322-derived ampicillin-resistant gene; and Ptrp indicates a promoter of Escherichia coli tryptophan operon. The arrows each indicate the direction in which the gene is transcribed and translated. In the figure, only the restriction enzyme sites having relation to the construction of the plasmid are shown.

Figure 3:
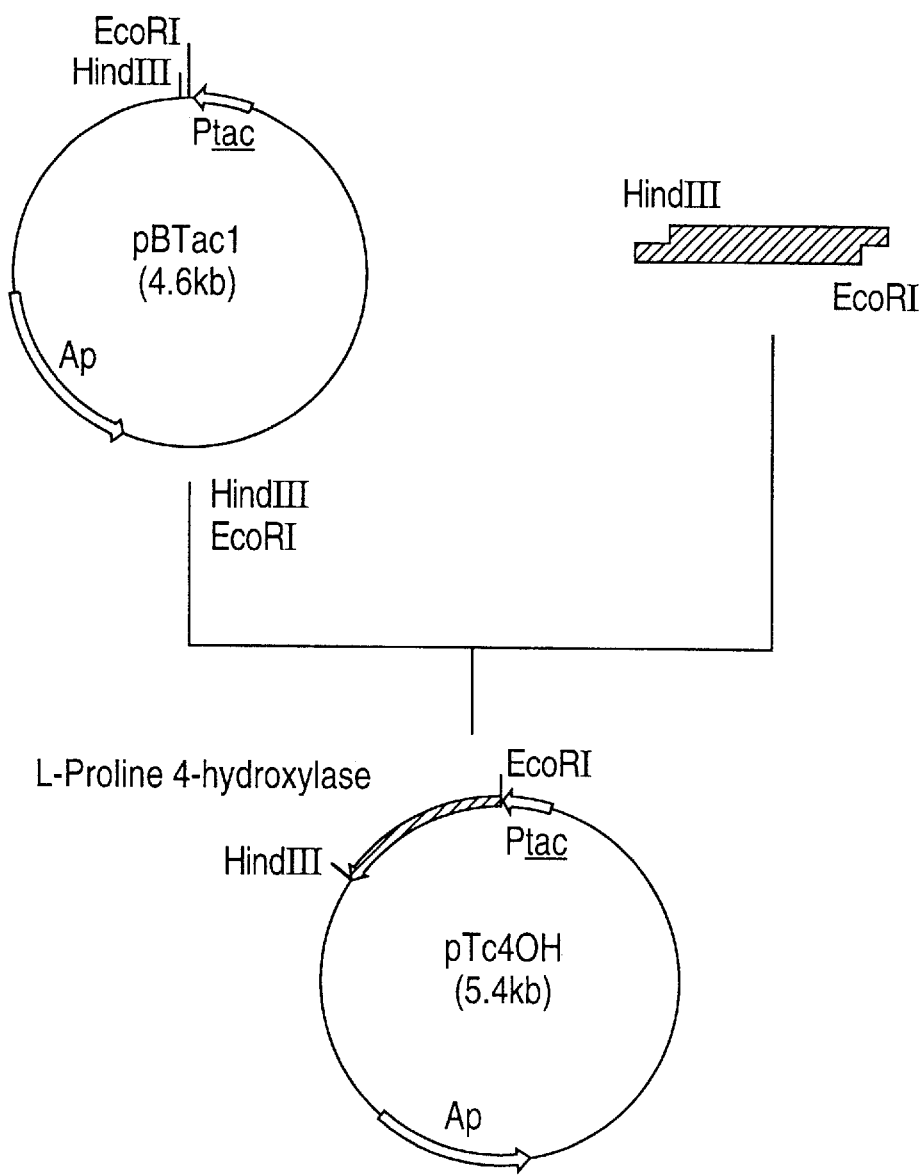

FIG. 3 shows the steps of constructing plasmid pTc4OH.

In the figure, the thick, solid black lines each indicate a part that contains an L-proline 4-hydroxylase gene. Ap indicates a pBR322-derived ampicillin-resistant gene; and Ptac indicates tac promoter. The arrows each indicate the direction in which the gene is transcribed and translated. In the figure, only the restriction enzyme sites having relation to the construction of the plasmid are shown.

Figure 4:
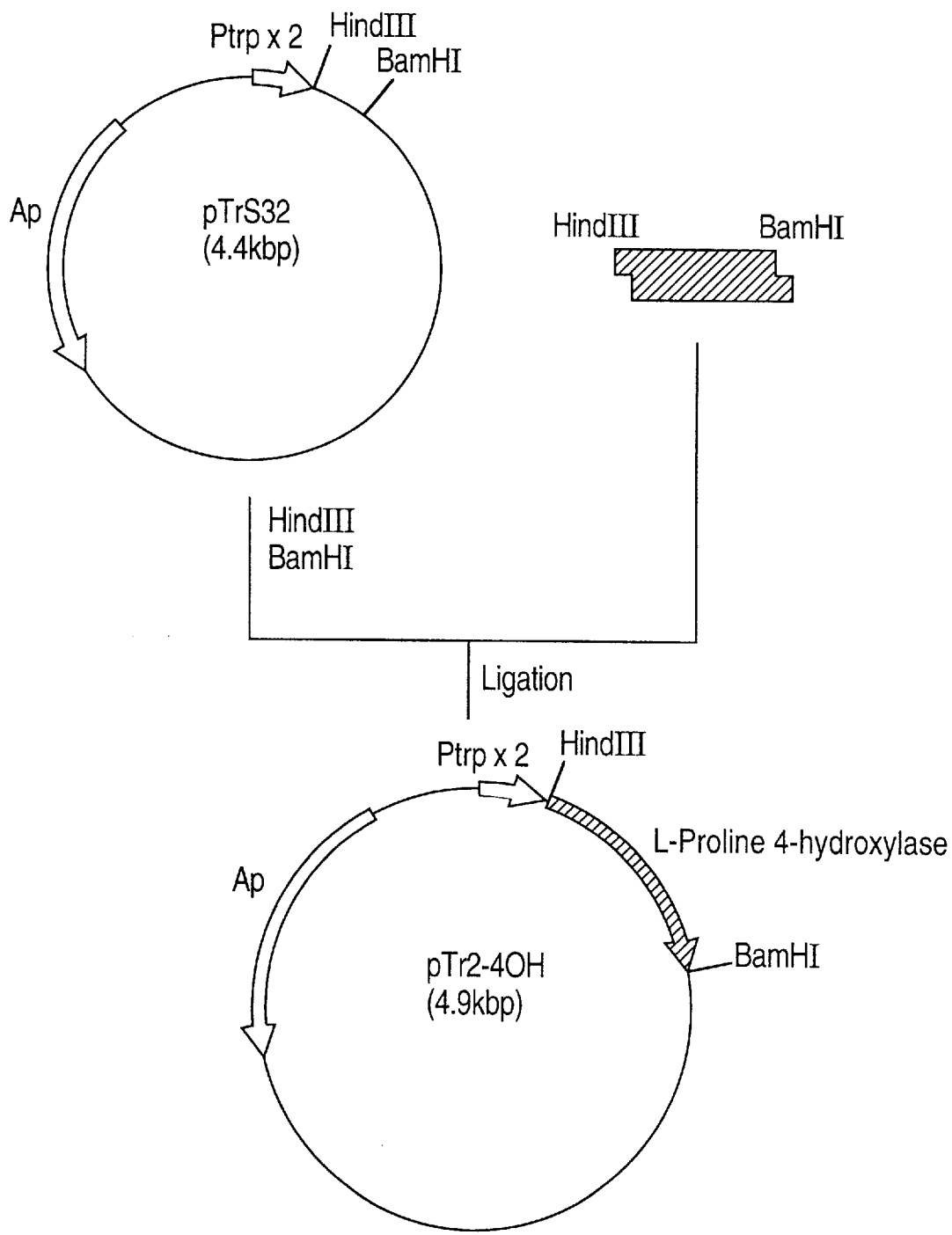

FIG. 4 shows the steps of constructing plasmid pTr2-4OH.

In the figure, the thick, solid black line each indicate a part that contains an L-proline 4-hydroxylase gene. Ap indicates a pBR322-derived ampicillin-resistant gene; and Ptrpx2 indicates a promoter composed of two promoters of Escherichia coli-derived tryptophan operon as connected in series (tandem tryptophan promoter). The arrows each indicate the direction in which the gene is transcribed and translated. In the figure, only the restriction enzyme sites having relation to the construction of the plasmid are shown.

Figure 5:
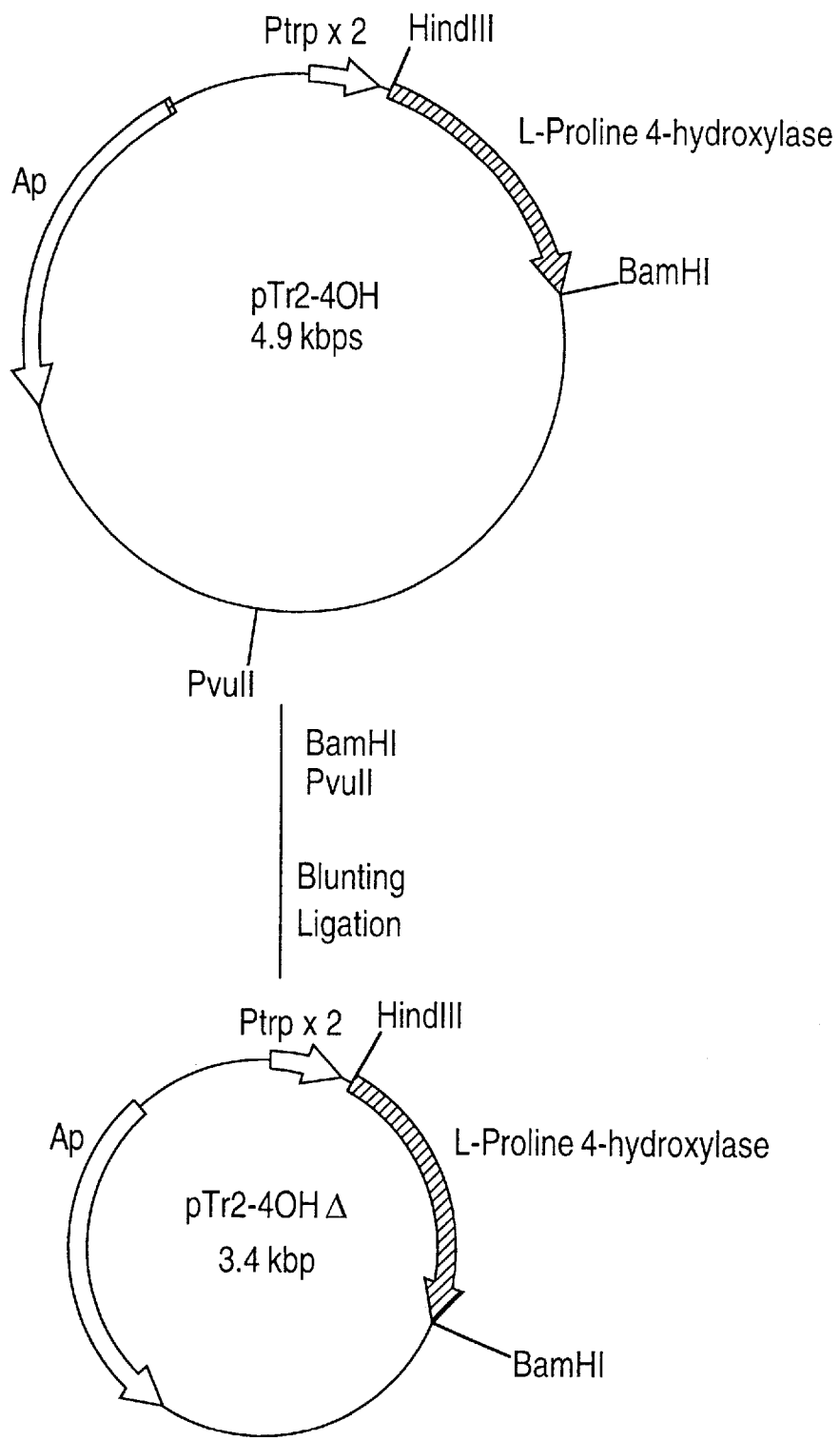

FIG. 5 shows the steps of constructing plasmid pTr2-4OHΔ.

In the figure, the thick, solid black lines each indicate a part that contains an L-proline 4-hydroxylase gene. Ap indicates a pBR322-derived ampicillin-resistant gene; and Ptrpx2 indicates a promoter composed of two promoters of Escherichia coli-derived tryptophan operon as connected in series (tandem tryptophan promoter). The arrows each indicate the direction in which the gene is transcribed and translated. In the figure, only the restriction enzyme sites having relation to the construction of the plasmid are shown.

Figure 6:
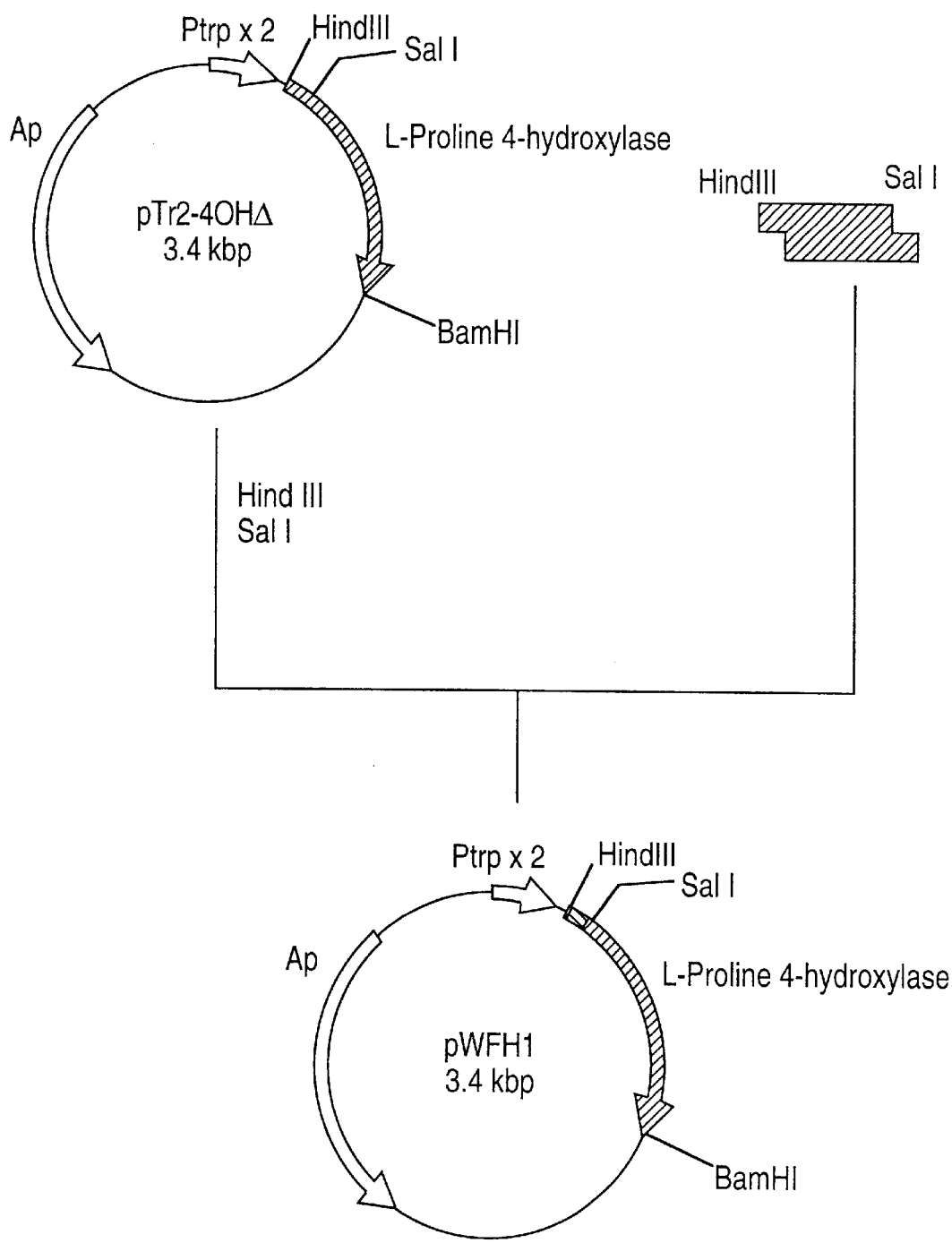

FIG. 6 shows the steps of constructing plasmid pWFH1.

In the figure, the thick, shadowed lines each indicate a site into which a PCR-amplified fragment as treated with HindIII and SalI is inserted. The thick, solid black lines each indicate a part that contains a Dactylosporangium sp. RH1-derived L-proline 4-hydroxylase gene. Ap indicates a pBR322-derived ampicillin-resistant gene; and Ptrpx2 indicates a promoter composed of two promoters of Escherichia coli-derived tryptophan operon as connected in series (tandem tryptophan promoter). The arrows each indicate the direction in which the gene is transcribed and translated. In the figure, only the restriction enzyme sites having relation to the construction of the plasmid are shown.

Figure 7:
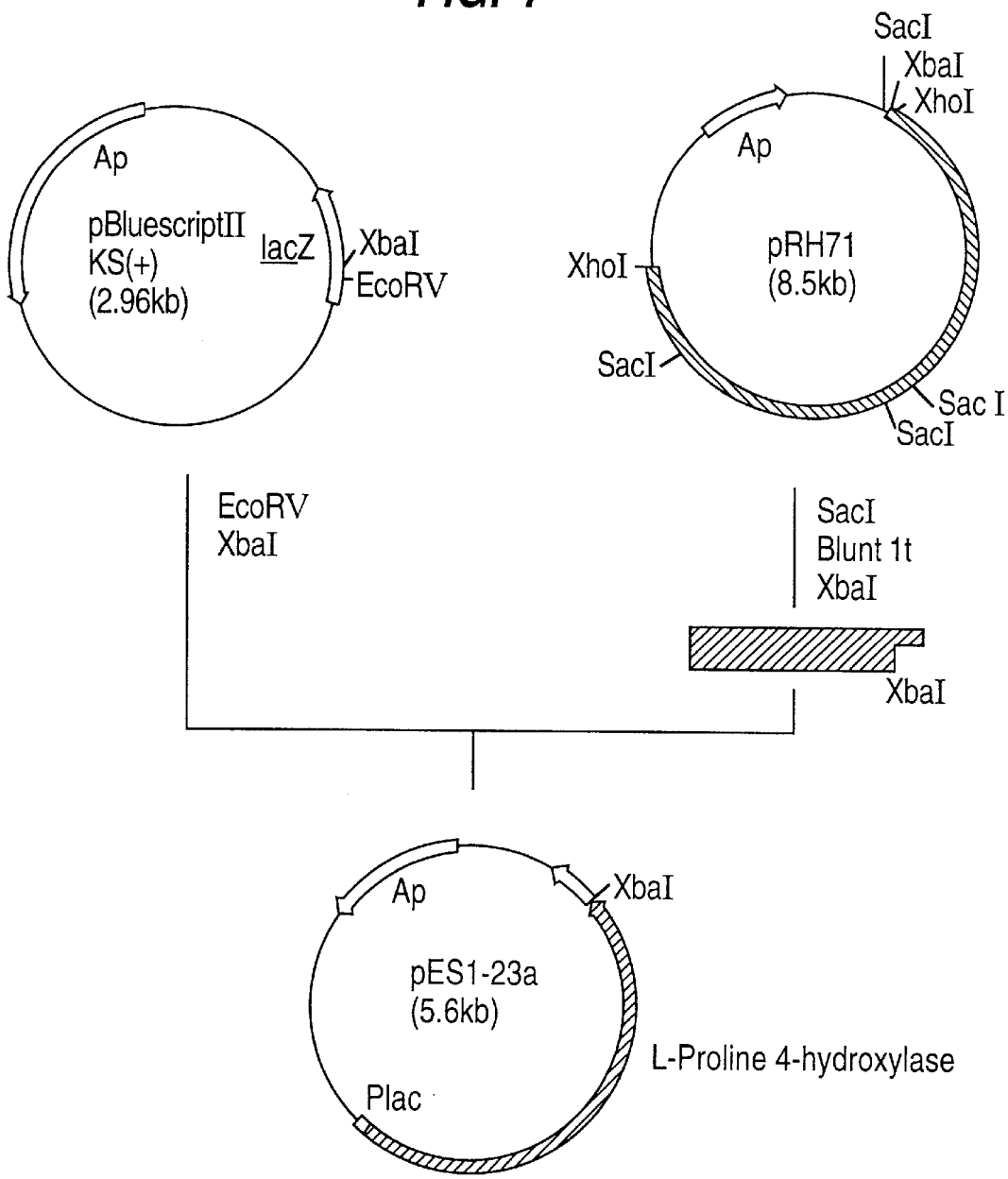

FIG. 7 shows the steps of constructing plasmid pESl-23a.

In the figure, the thick, solid black lines each indicate a part that contains an L-proline 4-hydroxylase gene. lacZ indicates Escherichia coli β-galactosidase gene; Ap indicates a pBR322-derived ampicillin-resistant gene; and Plac indicates lac promoter. The arrows each indicate the direction in which the gene is transcribed and translated. In the figure, only the restriction enzyme sites having relation to the construction of the plasmid are shown.

Figure 8:
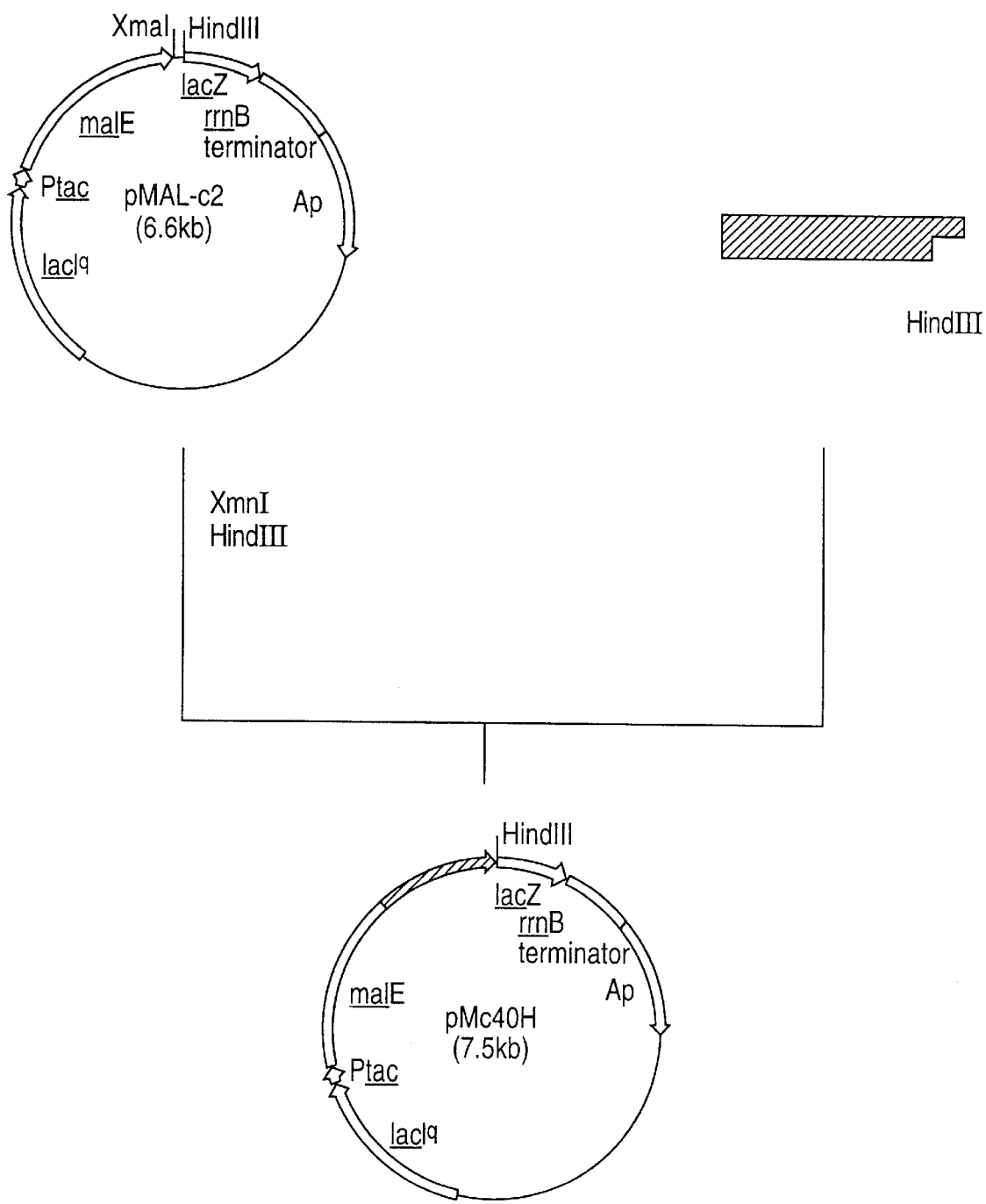

FIG. 8 shows the steps of constructing plasmid pMc4OH.

In the figure, the thick, solid black lines each indicate a part that contains an L-proline 4-hydroxylase gene. malE indicates Escherichia coli maltose-bonded protein gene; lacZ indicates Escherichia coli β-galactosidase gene; Ap indicates a pBR322-derived ampicillin-resistant gene; lacI$^q$ indicates a repressor gene of Escherichia coli lactose operon; rrnB terminator indicates a terminator of rrnB gene; and Ptac indicates tac promoter. The arrows each indicate the direction in which the gene is transcribed and translated. In the figure, only the restriction enzyme sites having relation to the construction of the plasmid are shown.

Figure 9:
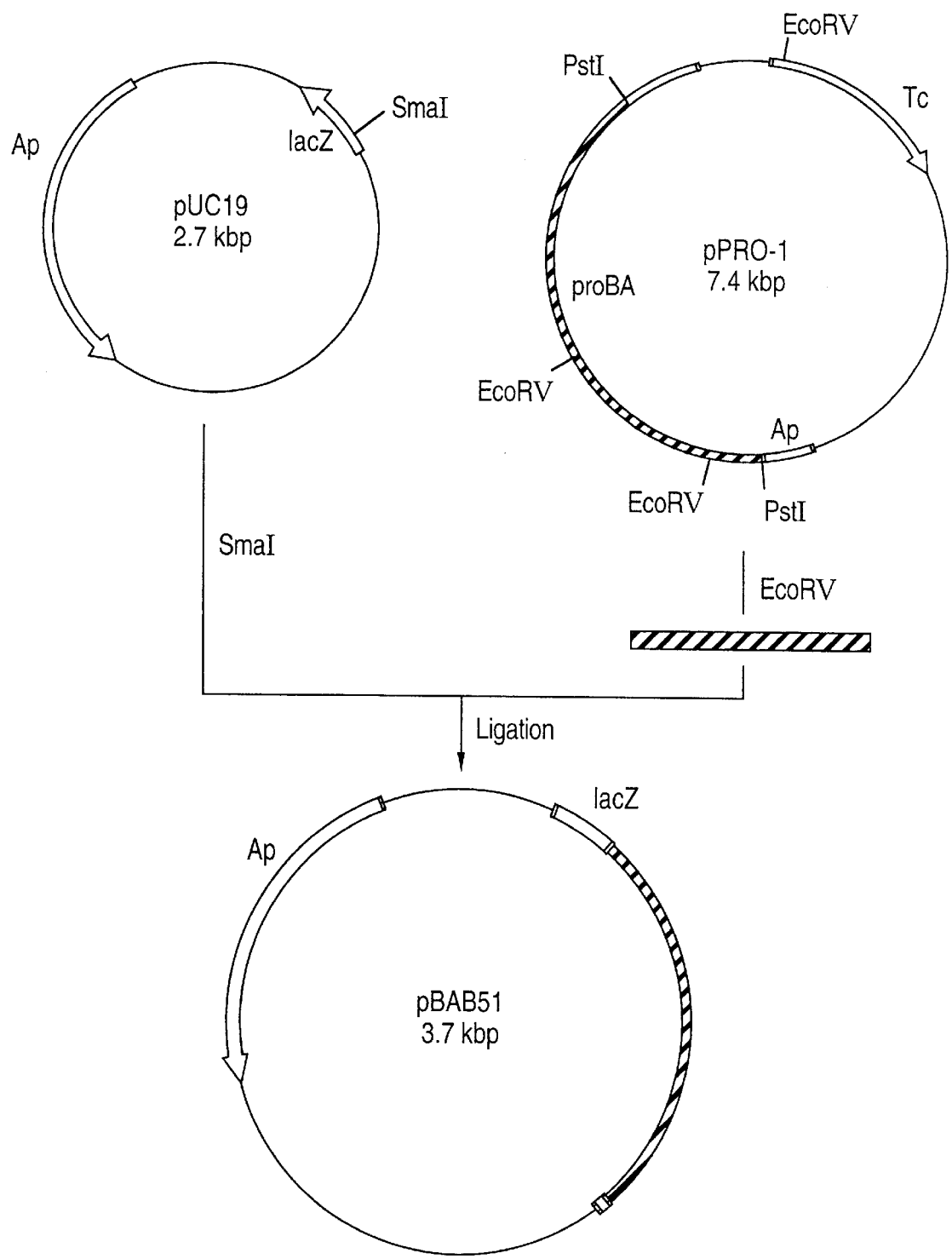

FIG. 9 shows the steps of constructing plasmid pBAB51.

In the figure, the thick, shadowed lines each indicate proline biosynthesis genes proB74 and proA. Ap indicates apBR322-derived ampicillin-resistant gene; lacZ indicates β-galactosidase α fragment construction gene; and Tc indicates a pBR322-derived tetracycline-resistant gene. The arrows each indicate the direction in which the gene is transcribed and translated. In the figure, only the restriction enzyme sites having relation to the construction of the plasmid are shown.

Figure 10:
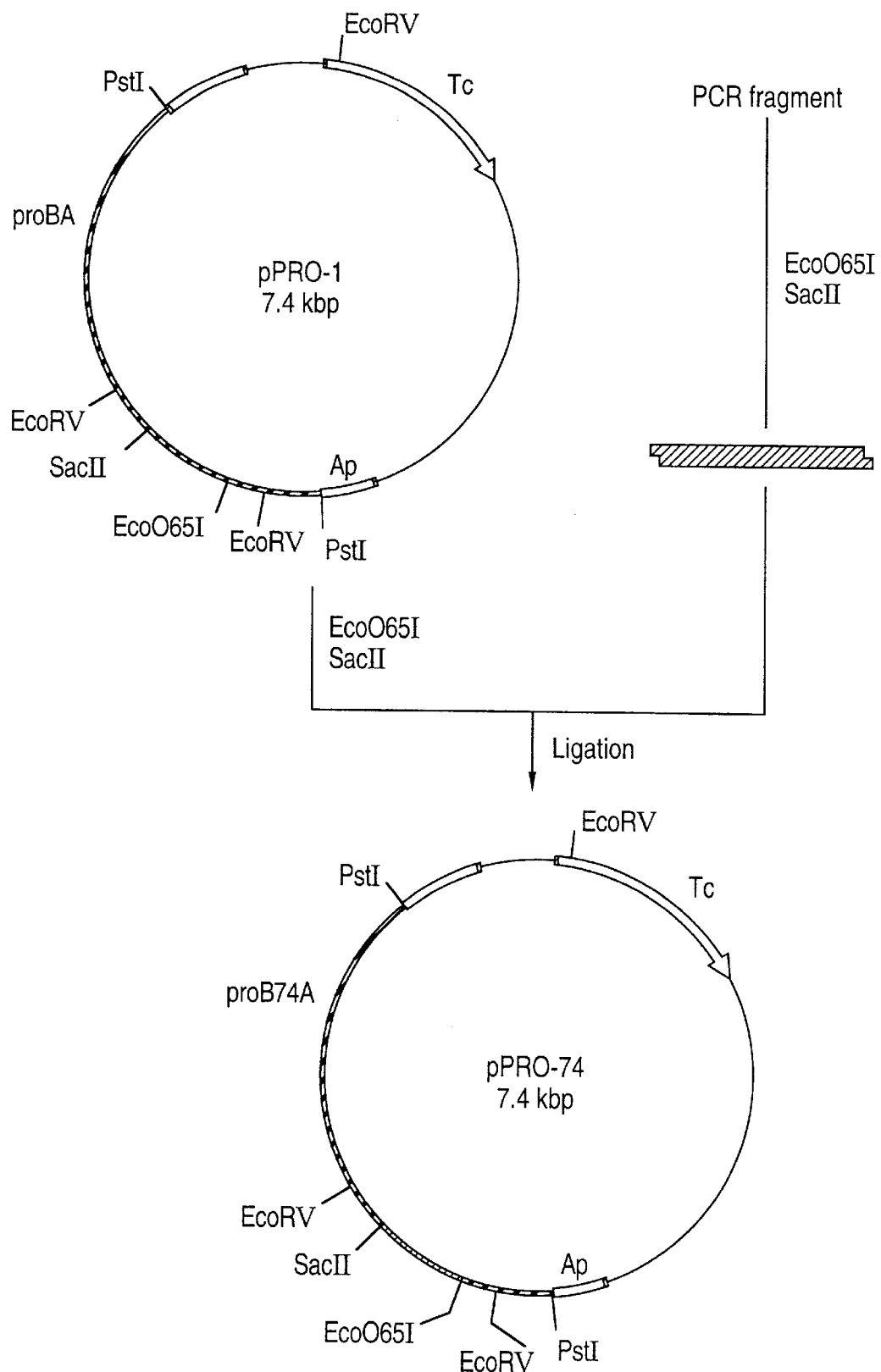

FIG. 10 shows the steps of constructing plasmid pPRO74.

In the figure, the thick, shadowed lines each indicate proline biosynthesis genes proB74 and proA. The thick, solid black lines in the thick, shadowed lines indicate DroB74 gene containing one base pair which is different from proB gene. Tc indicates a pBR322-derived tetracycline-resistant gene. The arrows each indicate the direction in which the gene is transcribed and translated. In the figure, only the restriction enzyme sites having relation to the construction of the plasmid are shown.

Figure 11:
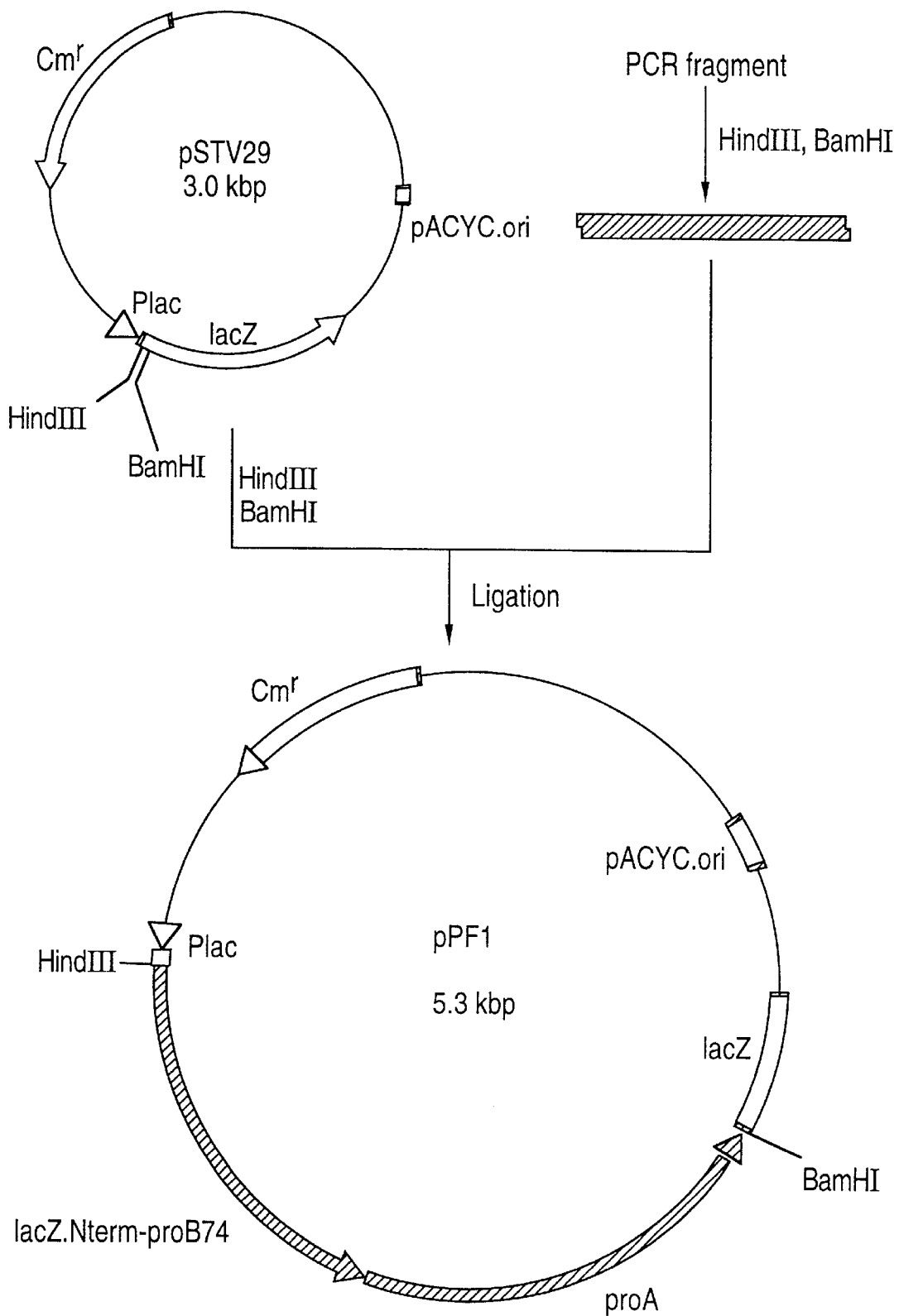

FIG. 11 shows the steps of constructing plasmid pPF1.

In the figure, the thick, shadowed lines each indicate proline biosynthesis genes proB74 and proA. Cm$^r$ indicates Tn9-derived chloramphenicol resistant gene; pACYC.ori indicates pACYC184-derived replication origin; Plac indicates lac promoter; lacZ indicates β-galactosidase a fragment construction gene; and lacZ.Nterm-proB74 indicates the gene coding for a protein which unites N-terminal amino acids of β-galactosidase α fragment with a protein encoded by proB74. The arrows each indicate the direction in which the gene is transcribed and translated. In the figure, only the restriction enzyme sites having relation to the construction of the plasmid are shown.

Figure 12:
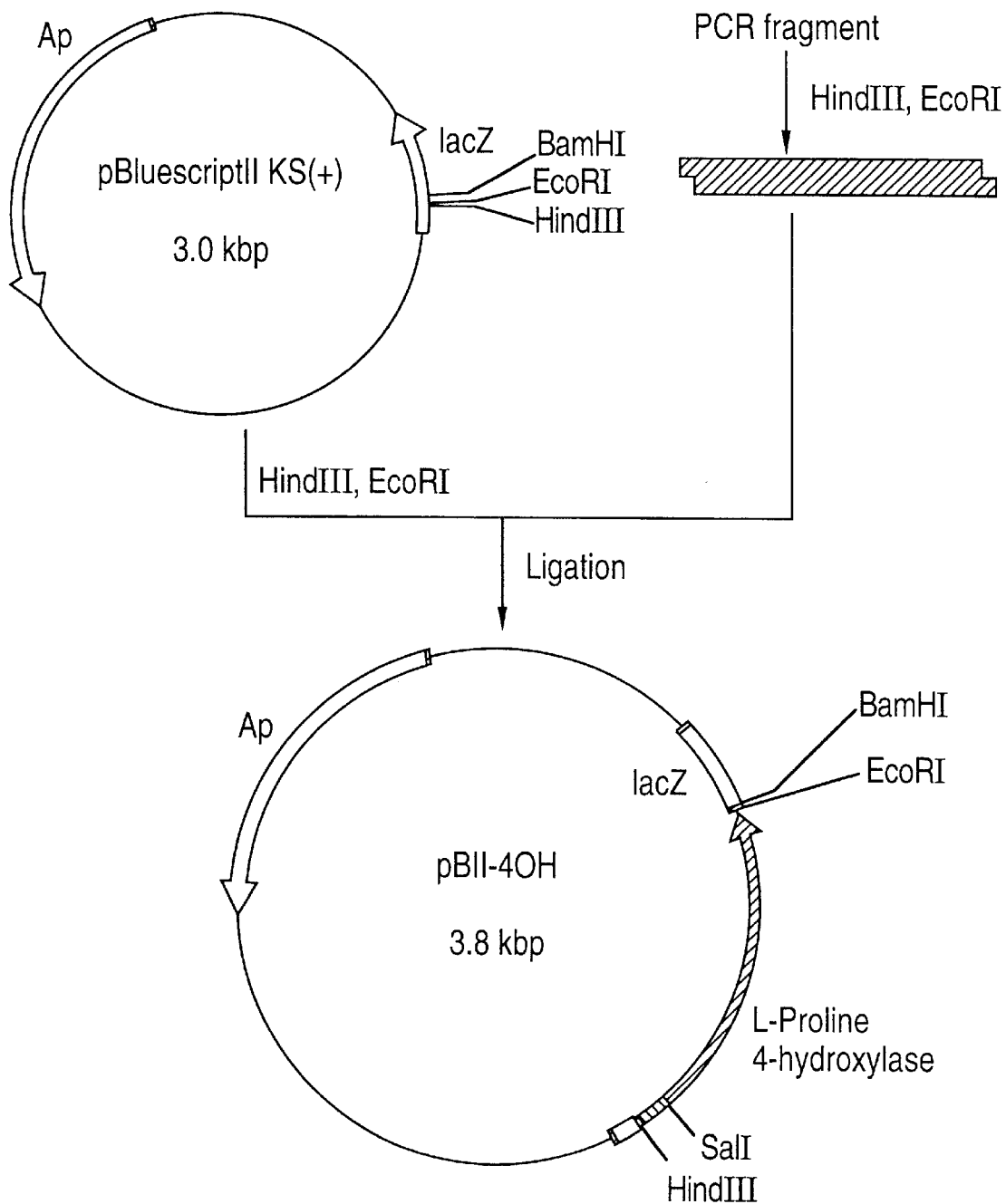

FIG. 12 shows the steps of constructing plasmid pBII-4OH.

In the figure, the thick, solid black lines each indicate a part that contains an L-proline 4-hydroxylase gene. Ap indicates a pBR322-derived ampicillin-resistant gene; and lacZ indicates β-galactosidase α fragment construction gene. The arrows each indicate the direction in which the gene is transcribed and translated. In the figure, only the restriction enzyme sites having relation to the construction of the plasmid are shown.

Figure 13:
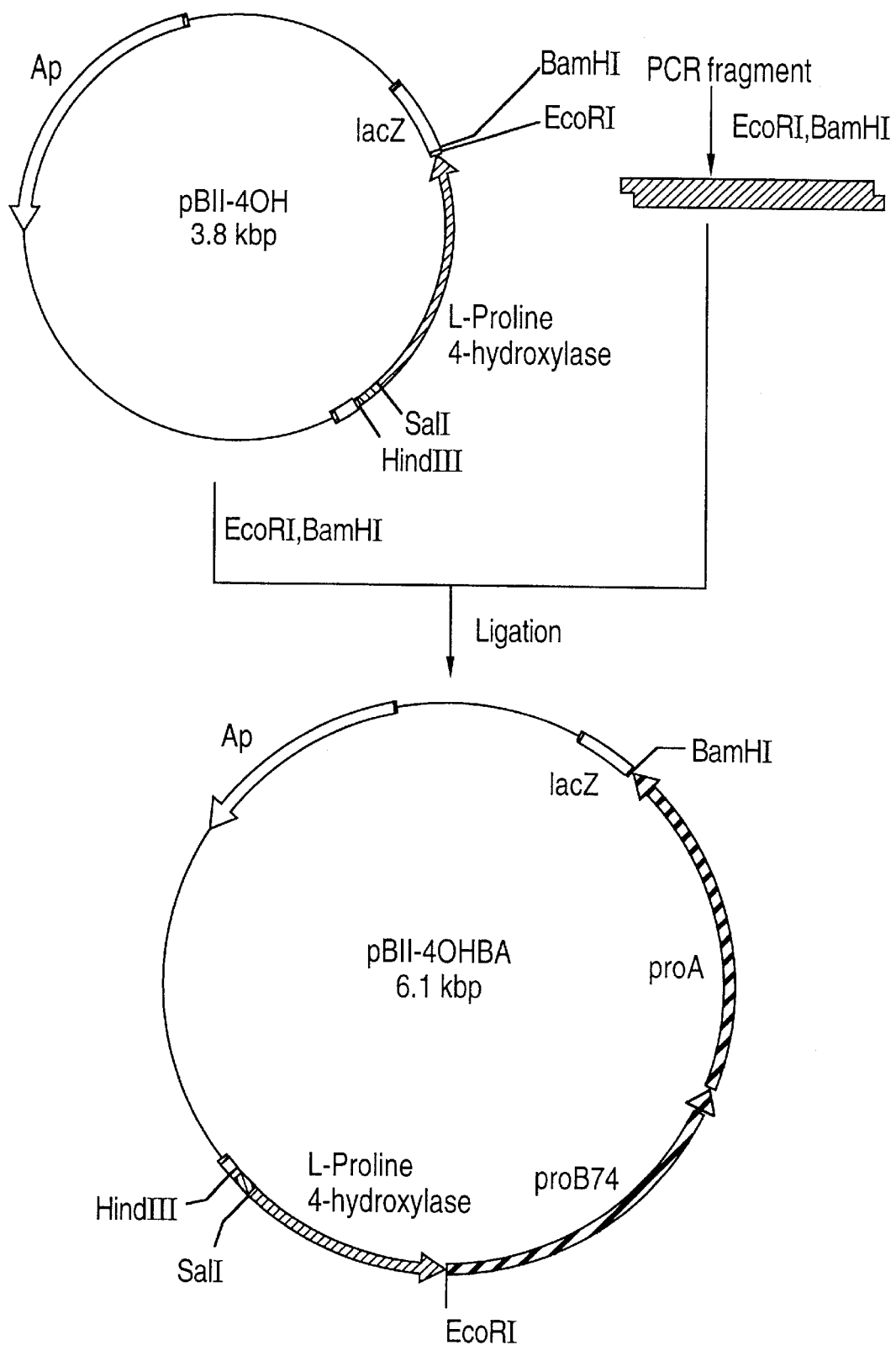

FIG. 13 shows the steps of constructing plasmid pBII-4OHBA.

In the figure, the thick, solid black lines each indicate a part that contains an L-proline 4-hydroxylase gene. Ap indicates a pBR322-derived ampicillin-resistant gene; and lacZ indicates β-galactosidase a fragment construction gene. The arrows each indicate the direction in which the gene is transcribed and translated. In the figure, only the restriction enzyme sites having relation to the construction of the plasmid are shown.

Figure 14:
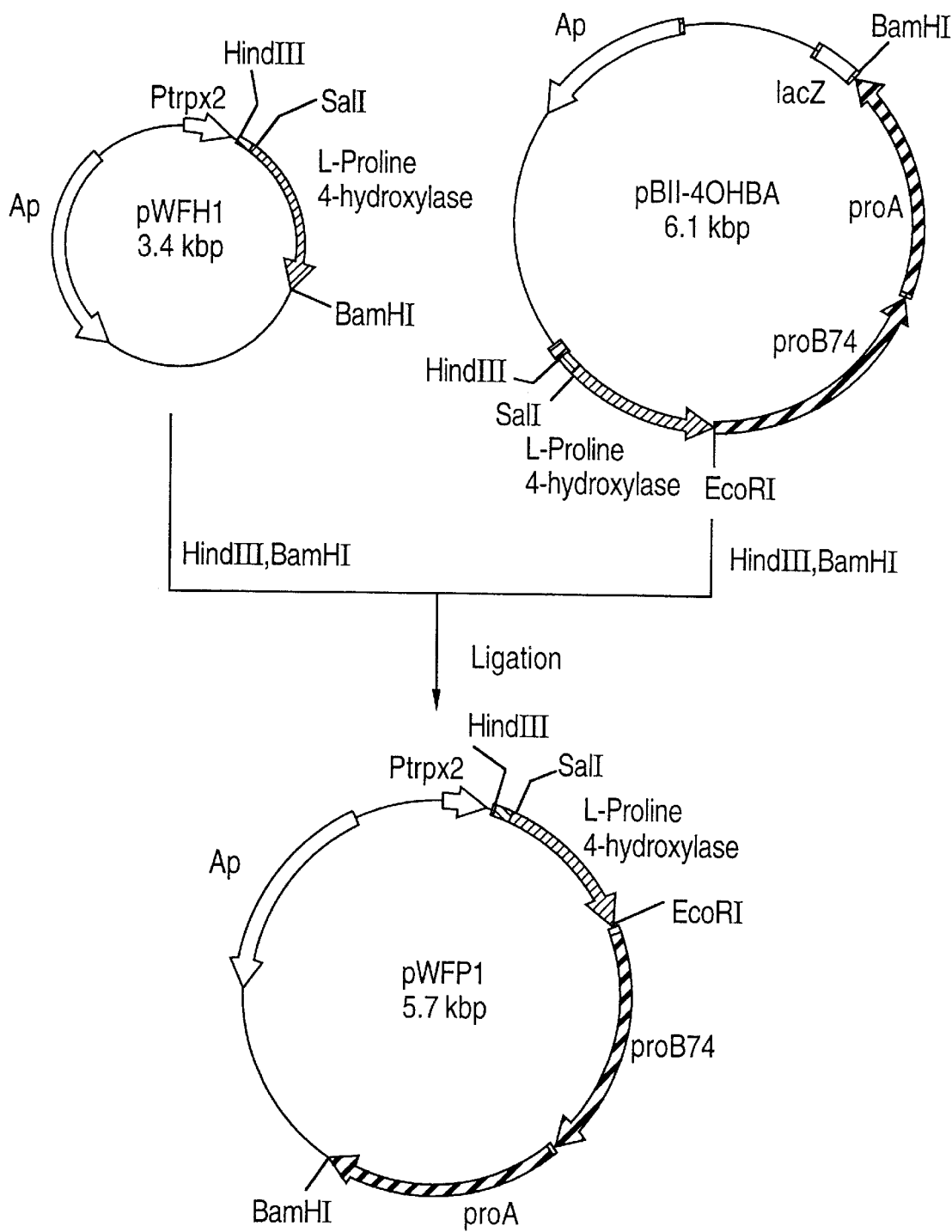

FIG. 14 shows the steps of constructing plasmid pWFP1.

In the figure, the thick, solid black lines each indicate a part that contains an L-proline 4-hydroxylase gene. The thick, shadowed lines each indicate proline biosynthesis genes proB74 and proA. Ap indicates a pBR322-derived ampicillin-resistant gene; and lacZ indicates β-galactosidase α fragment construction gene. Ptrpx2 indicates a promoter composed of two promoters of *Escherichia coli*-derived tryptophan operon as connected in series (tandem tryptophan promoter). The arrows each indicate the direction in which the gene is transcribed and translated. In the figure, only the restriction enzyme sites having relation to the construction of the plasmid are shown.

DETAILED DESCRIPTION OF THE INVENTION

As the enzyme source to be used in the process for producing trans-4-hydroxy-L-proline of the present invention, any microorganism can be used so long as it has an enzymatic activity of catalyzing the hydroxylation of L-proline at the 4-position of L-proline in the presence of 2-ketoglutaric acid and a divalent iron ion. As the microorganism having such activity, mention may be made of microorganisms belonging to the genus Dactylosporangium or Amycolatopsis. The preferred strain of such microorganism includes Dactylosporangium sp. RH1 and Amycolatopsis sp. RH2. Specifically, a culture, cells or processed cells of these strains can be used. Further, a crude enzyme preparation from cells of the microorganism as mentioned above, a purified product of such enzyme preparation, an immobilized enzyme preparation, etc. can be used.

The strains RH1 and RH2 were newly isolated by the present investors from a tree in Tokyo, Japan and from the soil in Saitama, Japan, respectively. The bacteriological properties of the strains RH1 and RH2 are described below.

1. Morphological Properties

The morphological properties when the strains were cultivated on various media at 28° C. for 14 days are shown in Table 1 below.

TABLE 1

Morphological Properties

| | Strain RH1 | Strain RH2 |
|---|---|---|
| 1) Hyphae | | |
| Branching mode of hyphae | Simple branching | Simple branching |
| Formation of aerial hyphae | Not observed | Yes |
| Fragmentation of aerial hyphae | | Yes |
| Fragmentation of substrate hyphae | Not observed | Yes |
| 2) Spores | | |
| Sporulation | Observed (as sporangiospores) | Not observed |
| Positions to which spores adhere | Adhered to substrate hyphae | |
| Morphology of sporangia | Rods, existing singly or as bundles composed of several rod sporangia. | Not observed |
| Number of sporangiospores per one sporangium | 2 to 4 | |
| Characteristics of sporangiospores | | |
| Surface | Smooth | |
| Shape | Oval sphere | |
| Size | 0.6 to 0.8 μm × 1.0 to 2.0 μm | |
| Motility | Yes | |
| 3) Others | | |
| Globose bodies | Observed | Not observed |
| Pseudosporangia | Not observed | Not observed |
| Chlamydospores | Not observed | Not observed |
| Synnema | Not observed | Not observed |

2. Cultural Characteristics in Various Media

The strain RH1 grows normally or vigorously on usual synthetic and natural media, while its substrate hyphae are orange. On some media, the strain often produces ocher or pale red soluble pigments.

The strain RH2 grows normally or vigorously on usual synthetic and natural media, while its substrate hyphae are pale yellow or brown and its aerial hyphae are white or gray. On some media, the strain often produces brown soluble pigments.

The cultural characteristics in the growth conditions and the colors of the strain RH1 and the strain RH2, when the strains were cultivated on various media at 28° C. for 14 days, are shown in Table 2. The designation of the colors has been made, according to the classification of colors indicated in Color Harmony Manual published by Container Corporation of America.

TABLE 2

Cultural Characteristics in Various Media

| | Strain RH1 | Strain RH2 |
|---|---|---|
| 1) Sucrose-nitrate agar | | |
| Growth | Moderate | Poor |
| Color of substrate hyphae | Apricot (4ga) | Pearly pink (3ca) |
| Formation of aerial hyphae | None | Poor |
| Color of aerial hyphae | | White (a) |
| Soluble pigments | None | None |
| 2) Glucose-asparagine agar | | |
| Growth | Moderate | Moderate |
| Color of substrate hyphae | Light gray to luggage tan (c to 4ne) | Light tan (3gc) |
| Formation of aerial hyphae | None | Poor |
| Color of aerial hyphae | | White to light amber (a to 3ic) |
| Soluble pigments | None | Produced only a little (ocher) |
| 3) Glycerol asparagine agar | | |
| Growth | Poor | Moderate |
| Color of substrate hyphae | Light melon yellow (3ea) | Light white to cinnamon (2ea to 31e) |
| Formation of aerial hyphae | None | Moderate |
| Color of aerial hyphae | | White (a) |
| Soluble pigments | None | Produced only a little (ocher) |
| 4) Inorganic salt starch agar | | |
| Growth | Moderate | Moderate |
| Color of substrate hyphae | Camel (3ie) | Light mustard tan to cinnamon (2ic to 31e) |
| Formation of aerial hyphae | None | Moderate |
| Color of aerial hyphae | | White to light gray (a to d) |
| Soluble pigments | None | Produced only a little (ocher) |
| 5) Tyrosine agar | | |
| Growth | Moderate | Moderate |
| Color of substrate hyphae | Apricot (4ia) | Mustard gold to golden brown (2pg to 3pg) |
| Formation of aerial hyphae | None | None |
| Color of aerial hyphae | | White (a) |
| Soluble pigments | Produced only a little (pale red) | Produced (brown) |
| 6) Nutrient agar | | |
| Growth | Poor | Poor |
| Color of substrate hyphae | Bright melon yellow (3ia) | Yellow maple (3ng) |
| Formation of aerial hyphae | None | Moderate |
| Color of aerial hyphae | | Light gray (b) |
| Soluble pigment | Produced only a little (ocher) | Produced (brown) |
| 7) Yeast extract-malt extract agar | | |
| Growth | Abundant | Good |
| Color of substrate hyphae | Orange (41a) | Mustard gold to golden brown (2pg) to (3pg) |
| Formation of aerial hyphae | Not formed | Moderate |
| Color of aerial hyphae | | Pearl (2ba) |
| Soluble pigments | Produced only a little (ocher) | Produced (brown) |
| 8) Oatmeal agar | | |
| Growth | Poor or moderate | Poor |
| Color of substrate hyphae | Apricot (4ia) | Mustard gold (2pg) |
| Formation of aerial hyphae | None | Poor |
| Color of aerial hyphae | | Natural (3dc) |
| Soluble pigments | Produced only a little (ocher) | Produced only a little (ocher) |

3. Physiological Properties

The physiological properties of the strains RH1 and RH2 are shown in Table 3, in which the "temperature range for growth" indicates the results of each strain after 7 day-cultivation with shaking. The remaining items indicate the results after 2 to 3 week-cultivation at 28° C.

TABLE 3

Physiological Properties

| | | Strain RH1 | Strain RH2 |
|---|---|---|---|
| 1) | Temperature Range for Growth | 20 to 37° C. | 13 to 35° C. |
| 2) | Liquefaction of Gelatin | − | + |
| 3) | Hydrolysis of Starch | + | + |
| 4) | Coagulation of Skim Milk Powder | − | + |
| 5) | Peptonization of Skim Milk Powder | − | + |
| 6) | Formation of Melancid Pigment | | |
| | (1) Peptone-yeast extract iron agar | − | + |
| | (2) Tyrosine agar | + | + |
| 7) | Utilization of Carbon Sources(*) | | |
| | L-Arabinose | + | − |
| | D-Glucose | + | + |
| | D-Xylose | + | + |
| | Sucrose | + | (+) |
| | Raffinose | (+) | + |
| | D-Fructose | + | + |
| | Rhamnose | + | + |
| | Inositol | (+) | + |
| | D-Mannitol | + | + |

(*) As the basic medium, used was Pridham Gottlieb-agar medium.
+ indicates that the strain utilized the carbon source;
− indicates that the strain did not utilize the carbon source; and
(+) indicates that it is not clear as to whether or not the strain utilized the carbon source.

4. Chemotaxonomic Properties

The chemotaxonomic properties of the strains RH1 and RH2 are shown in Table 4.

TABLE 4

Chemotaxonomic Properties

| | | Strain RH1 | Strain RH2 |
|---|---|---|---|
| 1) | Configuration of diaminopimelic acid in cell wall | 3-OH (meso) form | Meso form |
| 2) | Reducing sugars in | | Galactose and minor |

TABLE 4-continued

Chemotaxonomic Properties

|  | Strain RH1 | Strain RH2 |
|---|---|---|
| hydrolysate of cell wall | | amount of arabinose |
| 3) Reducing sugars in hydrolysate of whole cell | Arabinose and xylose | Arabinose and galactose |
| 4) Mycolic acid | | Not contained |
| 5) Phospholipid | | The cells contain phosphatidyl-ethanolamine but do not contain phosphatidyl-choline and unknown glucosamine-containing phospholipids. |
| 6) Menaquinone | | The cells contain MK-9 ($H_4$) as the major component. |

Accordingly, the strain RH1 is classified to the genus Dactylosporangium of actinomycetes in view of its properties (1) that it does not form aerial hyphae, (2) that it forms rod-like sporangia on its substrate hyphae, (3) that its sporangia contain from 2 to 4 motile spores each, (4) that the diaminopimelic acid contained in its cell wall is 3-hydroxydiaminopimelic acid and (5) that the hydrolysate of its whole cell contains reducing sugars of arabinose and xylose.

The strain RH2 is identified as the genus Amycolatopsis of actinomycetes in view of its properties (1) that it forms aerial hyphae, (2) that its aerial hyphae and substrate hyphae fragmented into coccoid or rod-shaped elements, (3) that its cell wall contains meso-diaminopimelic acid and reducing sugars of galactose and a slight amount of arabinose, (4) that the hydrolysate of its whole cell contains reducing sugars of arabinose and galactose, (5) that it does not contain mycolic acid as its cell-constitutive component (6) that it contains a phospholipid of phosphatidylethanolamine but does not contain phosphatidylcholine and unknown glucosamine-containing phospholipids and (7) that the major component of its major menaquinone is MK-9 ($H_4$).

The strain RH1 was named Dactylosporangium sp. RH1 and the strain RH2 was named Amycolatopsis sp. RH2. These strains have been deposited with National Institute of Bioscience and Human-Technology, Agency of Industrial Science and Technology in Japan as of Sep. 1, 1993 under FERM BP-4400 for the strain RH1 and as of Feb. 22, 1994 under FERM BP-4581 for the strain RH2, both in terms of the Budapest Treaty.

The medium for cultivating these microorganisms may be any of natural media and synthetic media, so long as it contains carbon sources, nitrogen sources, inorganic salts, etc. that may be assimilated by microorganisms having an activity of catalyzing hydroxylation of L-proline to produce trans-4-hydroxy-L-proline.

As the carbon sources, carbohydrates such as glucose, fructose, sucrose, molasses containing these components, starch and starch hydrolysates; organic acids such as acetic acid, propionic acid; alcohols such as ethanol and propanol may be used.

As the nitrogen sources, ammonia; ammonium salts of various inorganic acids and organic acids such as ammonium chloride, ammonium sulfate, ammonium acetate and ammonium phosphate; other nitrogen-containing compounds; peptone, meat extracts, yeast extracts, corn steep liquor, casein hydrolysates, soy bean cakes, soy bean cake hydrolysates, various cultured cells of microorganisms, their digested products, etc. may be used.

The inorganic material includes, for example, potassium dihydrogen phosphate, dipatassium hydrogen phosphate, magnesium phosphate, magnesium sulfate, sodium chloride, ferrous sulfate, manganese sulfate, copper sulfate, calcium carbonate, etc.

The cultivation of these microorganisms is carried out under aerobic conditions, for example, with shaking culture or submerged-aerial stirring culture. The temperature for the cultivation is preferably from 15° to 37° C., and the period for the cultivation is generally from 16 to 96 hours. During the cultivation, the pH of the medium is kept at 5.0 to 9.0 with inorganic or organic acids, alkaline solutions, urea, calcium carbonate, ammonia, etc.

The thus-cultivated microorganisms can be used as the enzyme source to be used in the process for producing trans-4-hydroxy-L-proline.

The amount of the enzyme source to be used in the process for producing trans-4-hydroxy-L-proline depends on the amount of the substrate to be used in the process. Usually, it may be from 1.0 to 10,000,000 U/liter, preferably from 1,000 to 3,000,000 U/liter of the aqueous medium.

The enzyme activity for producing one nmol of trans-4-hydroxy-L-proline for one minute under the conditions mentioned below is defined as one unit (U).

The enzyme preparation to be determined is added to 80 mM MES buffer (pH 6.5) containing 4 mM L-proline, 8 mM 2-ketoglutaric acid, 2 mM ferrous sulfate and 4 mM L-ascorbic acid to make 250 μl in total, and the mixture was allowed to stand at 30° C. for 20 minutes. The reaction mixture is heated at 100° C. for 2 minutes so as to stop the reaction, and the amount of the trans-4-hydroxy-L-proline produced in the reaction mixture is determined by high performance liquid chromatography (hereinafter referred to as HPLC).

For the determination, any method capable of determining the amountoftrans-4-hydroxy-L-prolinemaybe employed. For instance, generally usable are a post-column derivatization method where HPLC is utilized, and a pre-column derivatization method where the compound to be determined in the reaction mixture is previously reacted with 7-chloro-4-nitrobenz-2-oxa-1,3-diazole (hereinafter referred to as NBD) to form its NBD-derivative, the derivative is separated by reversed-phase chromatography using HPLC and the thus-separated derivative is quantitatively determined by spectrofluorometry (excitation wavelength: 503 nm, emission wavelength: 541 nm). The pre-column derivatization method may be conducted, according to the method of William J. Lindblad & Robert F. Diegelmann, et al. [see Analytical Biochemistry, 138, 390 (1984)].

The concentration of L-proline to be used in the process for producing trans-4-hydroxy-L-proline may be from 1 mM to 2M.

The process for producing trans-4-hydroxy-L-proline needs a divalent iron ion. The concentration of the divalent iron ion may be generally from 1 to 100 mM. Any divalent iron ion may be used so long as it does not inhibit the enzymatic reaction. For instance, sulfides such as ferrous sulfate, chlorides such as ferrous chloride and ferrous carbonate, the salts of organic acids such as citrates, lactates and fumarates may be used.

The process also needs 2-ketoglutaric acid. The concentration of 2-ketoglutaric acid is generally from 1 mM to 2M.

2-Ketoglutaric acid itself may be added to the aqueous medium, or alternatively, the compound that may be converted into 2-ketoglutaric acid by the metabolic activity of the microorganism used in the enzymatic reaction may be added thereto. The compound includes, for example, saccharides such as glucose, glutamic acid and succinic acid. These compounds may be used singly or in combination.

The aqueous medium to be used in the process for producing trans-4-hydroxy-L-proline of the present invention includes, for example, water, buffers such as phosphates, carbonates, acetates, borates, citrates and tris-buffers, alcohols such as methanol and ethanol, esters such as ethyl acetate, ketones such as acetone, and amides such as acetamide.

The enzymatic reaction may be carried out in the aqueous medium where the above-mentioned microorganisms having an activity of catalyzing hydroxylation of L-proline to produce trans-4-hydroxy-L-proline are being cultivated or have been cultivated, or alternatively, the enzymatic reaction may also be carried out in an aqueous medium containing the cells of the above mentioned microorganisms separated from the culture, a processed cells, or a purified or crude enzyme derived from the cells.

Processed cells of the microorganisms include, for example, dried cells, lyophilized cells, surfactant-treated cells, enzymatically-treated cells, ultrasonically-treated cells, mechanically-ground cells, mechanically-compressed cells, solvent-treated cells, fractionated cell proteins, immobilized cells, immobilized materials obtained by processing their cells, etc.

The enzymatic reaction is generally carried out at a temperature of 15° to 50° C. and at pH6.0 to 9.0, for a period of 1 to 96 hours. If desired, surfactants and/or organic solvents may be added during the processing of the cells or during the enzymatic reaction.

As the surfactants, mention may be made of cationic surfactants such as polyoxyethylene-stearylamine (e.g., Nymeen S-215, produced by Nippon Oils and Fats Co.), cetyltrimethylammonium bromide, Cation FB and Cation F2-40E, etc.; anionic surfactants such as sodium oleylamidosulfate, Newrex TAB and Rapizole 80; ampholytic surfactants such as polyoxyethylene-sorbitan monostearate (e.g., Nonion ST221); other tertiary amines PB, hexadecyldimethylamine, etc. Any surfactant that may promote the reaction may be employed. The concentration of the surfactant to be employed in the reaction may be generally from 0.1 to 50 mg/ml, preferably from 1 to 20 mg/ml.

As the organic solvent, mention may be made of toluene, xylene, aliphatic alcohols, benzene, ethyl acetates etc. Generally, the concentration of the solvent in the process may be from 0.1 to 50 $\mu$l/ml, preferably from 1 to 20 $\mu$l/ml.

To recover trans-4-hydroxy-L-proline from the aqueous medium, ordinary separation methods such as column chromatography using an ion-exchange resin, crystallization, etc. may be employed.

The structure of the recovered trans-4-hydroxy-L-proline can be identified by ordinary analytical method such as $^{13}$C-NMR spectrum, $^1$H-NMR spectrum, mass spectrum, specific rotation or the like.

Next, the novel enzyme, the L-proline-4-hydroxylase of the present invention is described below.

The L-proline-4-hydroxylase may be obtained by cultivating microorganisms having an ability to produce L-proline-4-hydroxylase in a medium so as to produce and accumulate the L-proline-4-hydroxylase in the culture medium, and recovering the L-proline-4-hydroxylase from the cells.

Any microorganisms having an ability to produce L-proline-4-hydroxylase may be employed. For example, microorganisms belonging to the genus Dactylosporangium or Amycolatopsis and having such activity can be used. Specific examples are the above-mentioned Dactylosporangium sp. RH1, Amycolatopsis sp. RH2, a subcultivated strain thereof, its mutant thereof, its derivative thereof, etc.

The medium for cultivating these microorganisms may be any of natural media and synthetic media, so long as it contains carbon sources, nitrogen sources, inorganic salts, etc. that may be assimilated by microorganisms having an ability to produce L-proline-4-hydroxylase.

The carbon source includes, for example, carbohydrates such as glucose, fructose, sucrose, molasses containing these components, starch and starch hydrolysates; organic acids such as acetic acid and propionic acid; alcohols such as ethanol and propanol which may be assimilated by the microorganisms.

As the nitrogen source, ammonia; ammonium salts of various inorganic acids and organic acids such as ammonium chloride, ammonium sulfate, ammonium acetate and ammonium phosphate; other nitrogen-containing compounds; peptone, meat extracts, yeast extracts, corn steep liquor, casein hydrolysates, soy bean cakes, soy bean cake hydrolysates, various microorganisms for fermentation, their digested products, etc. may be used.

As the inorganic material, dipotassium hydrogen phosphate, potassium dihydrogen phosphate, magnesium phosphate, magnesium sulfate, sodium chloride, ferrous sulfate, manganese sulfate, copper sulfate, calcium carbonate, etc. can be used.

The cultivation of these microorganisms is carried out under aerobic conditions, for example, with shaking culture or submerged-aerial stirring culture. The temperature for the cultivation is preferably from 15° to 37° C., and the period for the cultivation is generally from 16 to 96 hours.

During the cultivation, the pH of the medium is kept at 5.0 to 9.0 with inorganic or organic acids, alkaline solutions, urea, calcium carbonate, ammonia, etc. During the cultivation, L-proline may be added, if desired.

To isolate and purify the enzyme from the culture containing the enzyme, any ordinary method for isolating and purifying an enzyme may be employed. For instance, the culture is subjected to centrifugation to collect the cultivated cells therefrom, and the cells are fully washed and then disrupted by an ultrasonic cell disrupter, a French press, a Manton-Gauline homogenizer, a Dyno mill, etc. to obtain a cell-free extract. The cell-free extract is again subjected to centrifugation, and the enzyme in the resulting supernatant is then purified, for example, by salting-out with ammonium sulfate or the like, by anion-exchange chromatography with diethylaminoethyl (DEAE)-Sepharose or the like, by hydrophobic chromatography with butyl-Sepharose, phenyl-Sepharose or the like, by dye affinity chromatography with red-Agarose or the like, by gel filtration with molecular sieves or by electrophoresis such as isoelectric point electrophoresis or the like. In this way, a pure product of the enzyme is obtained. The activity of the L-proline-4-hydroxylase thus isolated may be determined by the same method as mentioned above.

The L-proline-4-hydroxylase, thus obtained according to the manner mentioned above, has the following physico-chemical properties (1) to (10);

(1) Action and Substrate Specificity

The hydroxylase catalyzes hydroxylation of L-proline at the 4-position of L-proline in the presence of 2-ketoglutaric acid and a divalent iron ion to form trans-4-hydroxy-L-proline.

(2) Optimum pH Range

In the above-mentioned method of determining the activity of the hydroxylase, the reaction was carried out while the buffer component in the reaction mixture was changed to sodium acetate buffer at pH of 3.5 to 5.5, it was changed to MES buffer at pH of 5.5 to 6.5, it was changed to TES buffer [N-tris(hydroxymethyl)methyl-2-aminoethanesulfonic acid] at pH of 7.0 to 7.5, it was changed to TAPS buffer [N-tris(hydroxymethyl)methyl-3-aminopropanesulfonic acid] at pH of, 8.0 to 9.0, and it was changed to CAPSO buffer (3-N-cyclohexylamino-2-hydroxypropanesulfonic acid) at pH of 9.5 to 11.0. As a result, it was found that the optimum pH range for the enzyme was in the range of pH 6.0 to pH 7.0.

(3) Stable pH Range

The enzyme was allowed to stand in the presence of 50 mM of a buffer (sodium acetate buffer at pH of 3.5 to 5.5, MES buffer at pH of 5.5 to 6.5, TES buffer at pH of 7.0 to 7.5, TAPS buffer at pH of 8.0 to 9.0, CAPSO buffer at pH of 9.5 to 11.0), 2 mM dithiothreitol (DTT) and20% (v/v) ofglycerol, at4° C. for 24 hours, and then its activity was determined. The enzyme kept at pH ranging from 6.5 to 10.0 had an activity of 90% or more of the original activity of the enzyme. Accordingly, it was found that the enzyme was stable at pH ranging from 6.5 to 10.0.

(4) Optimum Temperature Range

In the above-mentioned method of determining the activity of the hydroxylase acting on the 4-position of L-proline, the activity of the enzyme was determined, varying the temperature. As a result, it was found that the enzyme had an optimum temperature ranging from 30° to 40° C. in the reaction at pH of 6.5 for 15 minutes.

(5) Stable Temperature Range

When the enzyme was allowed to stand at 50° C. and at pH of 9.0 for 30 minutes, it was inactivated.

(6) Inhibitors

The activity of the enzyme is inhibited by metal ions of $Zn^{++}$ and $Cu^{++}$ and by EDTA. According to the above mentioned method of determining the activity of the hydroxylase acting on the 4-position of L-proline, when the activity of the enzyme was determined in the presence of $Cu^{++}$ and $Zn^{++}$ ions of 1 mM each, it was lowered, to 13% and 6%, respectively, of the original activity of the enzyme. Likewise, when the activity of the enzyme was determined in the presence of 5 mM EDTA, no activity of the enzyme was detected.

(7) Activation

No activation of the enzyme was observed, when various metal ions and cofactors were added thereto. Accordingly, the activation of the enzyme does not need any cofactor.

Ascorbic acid promotes the activity of the enzyme.

(8) Km Value

The Km values of the enzyme were 0.27 mM for L-proline and 0.55 mM for 2-ketoglutaric acid, when determined in the reaction system containing 80 mM MES buffer (pH 6.5), 4 mM L-ascorbic acid, 2 mM ferrous sulfate and a pre-determined amount of the enzyme.

(9) Molecular Weight

The molecular weight of the enzyme was calculated to be 32,000±5,000 daltons, by sodium dodecylsulfate polyacrylamide gel electrophoresis [using polyacrylamide gel, PAGEL NPU-12.5L (produced by Atto Co.) and Molecular Weight Standard Broad Range SDS-PAGE (produced by Biorad Co.)]. It was calculated to be 43,800±5,000 daltons, by gel filtration with HPLC (using a column of G-3000SW having a size of 21.5 mm×60 cm, and a molecular weight marker for HPLC produced by Oriental Yeast Co. as the standard).

(10) N-terminal Amino Acid Sequence

The enzyme has an N-terminal amino acid sequence illustrate by Sequence No. 1.

Sequence No. 1:

| (N-terminal) | 1 | MetLeuThrProThrGluLeuLysGlnTyr |
|---|---|---|
| | 11 | ArgGluAlaGlyTyrLeuLeuIleGluAsp |
| | 21 | GlyLeuGlyProArgGluVal |

The L-proline-4-hydroxylases of the present invention are enzymes by which free L-proline is hydroxylated in the presence of 2-ketoglutaric acid and a divalent ion to form trans-4-hydroxy-L-proline.

The present invention encompasses any and every protein having the enzymatic activity of hydroxylating the 4-position of L-proline, which includes, for example, a protein having the amino acid sequence indicated by Sequence No. 2, a fused protein having an amino acid sequence that results from the protein or a protein having a partial amino acid sequence of the protein as bonded to a peptide having a partial amino acid sequence of an *Escherichia coli*-derived β-galactosidase protein, a fused protein having an amino acid sequence that results from the protein having the amino acid sequence indicated by Sequence No. 2 or a protein having a partial amino acid sequence of the protein as bonded to a peptide having a partial amino acid sequence of an *E. coli*-derived maltose-binded protein, etc. Examples of the fused proteins include a proteins having the amino acid sequence as indicated by Sequence No. 19 or 20, etc.

The protein having the amino acid sequence indicated by Sequence No. 2, 19 or 20 includes proteins having an amino acid sequence with one or more amino acids substituted, deleted or added and having the enzymatic activity of hydroxylating the 4-position of L-proline. The substitution, the deletion and the addition of amino acids can be conducted in accordance with the methods described in Nucleic Acids Research, 10, 6487 (1982); Proc. Natl. Acad. Sci. USA., 79, 6409 (1982); Proc. Natl. Acad. Sci. USA., 81, 5662 (1984); Science, 224, 1431 (1984); PCT W085/00817 (1985); Nature, 316, 601(1985); Gene, 34, 315 (1985); Nucleic Acids Research, 13, 4431 (1985); Current Protocols in Molecular Biology, Chap. 8, Mutagenesis of Cloned DNA, John Wiley & Sons, Inc. (1989), etc.

The present invention encompasses any and every L-proline-4-hydroxylase gene of a DNA fragment containing a gene that codes for a protein having the enzymatic activity of hydroxylating the 4-position of L-proline, and this may include, for example, genes coding for the protein having the amino acid sequence as indicated by Sequence No. 2, 19 or 20, and also genes which code for a protein that has an amino acid sequence corresponding to the amino acid sequence as indicated by Sequence No. 2, 19 or 20 and derived therefrom by substitution, deletion or addition of at least one amino acid and which have the enzymatic activity of hydroxylating the 4-position of L-proline. Concretely mentioned are DNAs indicated by Sequence Nos. 3, 9 and 16, etc.

The L-proline-4-hydroxylase genes of the present invention include the DNAs as defined hereinabove and also DNAs as derived therefrom by mutation, such as substituting mutation, deleting mutation, inserting mutation or the like, to be conducted to the extent that the mutated DNAs do not lose the L-proline-4-hydroxylase activity, for example, DNAs with homology to Sequence No. 3, 9 or 16. Such homologous DNAs are those to be obtained by colony hybridization or plaque hybridization using, as a probe, the DNA having the nucleotide sequence as indicated by Sequence No. 3, 9 or 16. These treatments can be conducted in accordance with known in vitro recombination techniques [see Molecular Cloning: A Laboratory Manual, 2nd Ed., edited by Sambrook, Fritsch, Maniatis, published by Cold Spring Harbor Laboratory Press, 1989].

The DNA fragment containing the L-proline-4-hydroxylase gene can be obtained from microorganisms having the ability of hydroxylating L-proline to produce trans-4-hydroxy-L-proline. As the microorganism, any microorganism having the ability of hydroxylating L-proline to produce trans-4-hydroxy-L-proline can be employed in the present invention. As preferable examples of such a microorganism, microorganisms belonging to the genus Dactylosporangium, Amycolatpsis or Streptomyces and having the activity of L-proline-4-hydroxylase can be mentioned. More preferable examples thereof include Dactylosporangium sp. RH1 (FERMBP-4400), *Amycolatpsis sp.* RH2 (FERMBP-4581), *Streptomyces griseovirides* JCM4250, *Streptomyces daghestanicus* JCM4365, and mutants or derivatives of these strains.

Dactylosporangium sp. RH1 and Amycolatpsis sp. RH2 are microorganisms isolated by the present inventors isolated as those having the ability of producing L-proline-4-hydroxylase, and *Streptomyces griseovirides* JCM4250 and *Streptomyces daghestanicus* JCM44365 are microorganisms whose ability of producing L-proline-4-hydroxylases was found by the present inventors for the first time.

Methods for obtaining L-proline-4-hydroxylase gene of the microorganism having the ability of producing L-proline-4-hydroxylase is described below.

Chromosomal DNA is prepared from a microorganism having the ability of producing L-proline-4-hydroxylase through a usual DNA isolation method, for example, aphenol method (Biochem. Biophys. Acta, 72, 619). The thus-obtained chromosomal DNA is cleaved with a suitable restriction endonuclease, then the restriction endonuclease cleaved fragments are inserted into vector DNAs to construct chromosomal DNA libraries for the chromosomes of the microorganisms. Using this chromosomal DNA library, a host microorganism can be transformed. The transformants containing the L-proline-4-hydroxylase gene are selected from the obtained transformants by a hybridization method. DNAs containing the intended gene can be obtained from the thus-selected transformants.

The process comprising a series of such steps can be conducted in accordance with known in vitro recombination method (molecular Cloning, A Laboratory Manual, 2nd edition, edited by Sambrook, Fritsch and Maniatis, Cold Spring Harbor Laboratory Press, 1989).

As the vector DNAs that are used to construct the chromosomal DNA library of the microorganism having the ability of producing L-proline-4-hydroxylase, phage vectors and plasmid vectors can be used if these can be replicated autonomously in *Escherichia coli* K12 strain. Preferable examples of the vector DNA include λZAPII, pUC18 and pBluescript (commercially available from STRATAGENE Co.).

As the host microorganisms that are used to constructe the chromosomal DNA library of the microorganism having the ability of producing L-proline-4-hydroxylase, any of the microorganisms belonging to the genus Escherichia can be used. Preferable examples of the host microorganisms include *E. coli* XL1-Blue, *E. coli* XL2-Blue, *E. coli* DH1, *E. coli* MC1000, etc.

Based on the information about the amino acid sequence of L-proline-4-hydroxylase, DNA primers are synthesized. Using the DNA primers, DNA fragments are prepared through polymerase chain reaction (hereinafter referred to as PCR). Using the thus-obtained DNA fragments, transformants containing an L-proline-4-hydroxylase gene can be selected by the hybridization method.

The information on the amino acid sequences of L-proline-4-hydroxylases can be obtained through analysis of pure L-proline-4-hydroxylases using ordinary amino acid sequencers, such as Protein Sequencer Model PPSQ-10 (produced by Shimadzu Seisakusho K.K.). As the information on the amino acid sequences thus obtained, concretely mentioned are partial amino acid sequences in the amino acid sequence as indicated by Sequence No. 2, for example, a partial amino acid sequence having the amino acid sequence from the N-terminal to the 27th amino acid sequence indicated by Sequence No. 1, etc.

The DNA primer can be synthesized by means of an ordinary DNA synthesizer, for example, 380A•DNA Synthesizer manufactured by Applied Biosystems.

As the probes for the hybridization, usable are partial fragments of L-proline-4-hydroxylase genes, which can be obtained through PCR. For example, a DNA as indicated by Sequence No. 4 (this corresponds to a sense chain DNA coding for the first to the sixth amino acids in the amino acid sequence of Sequence No. 2) and a DNA as indicated by Sequence No. 5 (this corresponds to an anti-sense chain DNA coding for the 19th to 24th amino acids in the amino acid sequence of Sequence No. 2) are chemically synthesized. Through PCR using these as DNA primers, obtained is a DNA fragment of 71 bp as indicated by Sequence No. 6. The thus-obtained DNA fragment can be used as the probe for the hybridization.

The DNA which contains the L-proline-4-hydroxylase gene and which is obtained from the transformant selected by the hybridization, is cleaved by a suitable restriction endonucleases, for example, Xho I, and then cloned into a plasmid such as pBluescript KS(+) (commercially available from STRATAGENE Co.). The nucleotide sequence of the above-mentioned gene can be determined by ordinary nucleotide-sequence determination methods, for example, the dideoxy chain termination method of Sanger et al. [Proc. Natl. Acad. Sci., U.S.A., 74, 5463, (1977)]. The determination of the nucleotide sequence can be conducted by an automatic DNA sequencer, for example, 373A•DNA Sequencer of Applied Biosystems. As the thus-determined nucleotide sequences of the L-proline-4-hydroxylase genes, for example, the nucleotide sequence indicated by Sequence No. 3 can be mentioned.

The DNA that codes for an L-proline-4-hydroxylase of the present invention can be introduce into vectors in a usual manner.

As the plasmids containing the DNA encoding the L-proline-4-hydroxylase of the present invention, for example, pRH71, etc. can be mentioned. *Escherichia coli* SOLR/pRH71 which is *Escherichia coli* containing pRH71 was deposited at the National Institute of Bioscience and Human-Technology of the Agency of Industrial Science and Technology as of Mar. 2, 1995 under FERM EP-5025 in terms of the Budapest Treaty.

To express the thus-obtained L-proline-4-hydroxylase gene in the host, the DNA fragment containing the L-proline-4-hydroxylase gene is first cleaved by a restriction endonuclease or other deoxyribonuclease to form a DNA fragment of a suitable length containing the L-proline-4-hydroxylase gene. The thus-formed DNA fragment is inserted into an expression vector at the downstream position of the promoter therein, and thereafter the expression vector having the thus-inserted DNA therein is introduced into a host cell suitable for the expression vector.

Any host cell that can express the intended gene can be used. As examples of the host cell, microbial cells of a microorganism belonging to the genus Escherichia, Serratia, Corynebacterium, Brevibacterium, Pseudomonas, and Bacillus, etc., as well as yeast strains, animal cell hosts, etc. can be mentioned.

An expression vector, which can be autonomously replicable in the above-mentioned host cell or capable of being inserted into a chromosome and which contains a promoter at the position where the L-proline-4-hydroxylase gene can be transcribed, can be used.

When the microorganisms such as *Escherichia coli* or the like are used as the host cell, it is advisable that the expression vector is replicated autonomously in the microorganisms and is composed of a promoter, a ribosome binding sequence such as a Shine-Dargarnosequence, an L-proline-4-hydroxylase gene and a transcription termination sequence. A regulatory gene may be contained therein.

As examples of the expression vector, mentioned are pBTrp2, pBTac1, pBTac2 (all commercially available from Behringer Manheim Co.); pKYP10 (see Japanese Published Unexamined Patent Application No. 110600/83); pKYP200 [see Agric. Biol. Chem., 48, 669 (1984)]; pLSA1 [see Agric. Biol. Chem., 53, 277 (1989)]; pGEL1 [see Proc. Natl. Acad. Sci. USA., 82, 4306 (1985)]; pBluescript (produced by STRATAGENE Co.); pTrs30 [prepared from *Escherichia coli* JM109/pTrS30 (FERM BP-5407); pTrs32 [prepared from *Escherichia coli* JM109/pTrs32 (FERM BP-5408)], etc.

As the promoter, usable is any one capable of being expressed in hosts such as *Escherichia coli*. For example, mentioned are promoters derived from *Escherichia coli*, phage, etc., such as trp promoter (Ptrp), lac promoter (Plac), $P_L$ promoter and $P_R$ promoter. Also usable are artificially designed and modified promoters, such as Ptrpx2 to be prepared by connecting two Ptrps in series, as well as tac promoter (ptac).

As the ribosome-binding sequence, any one capable of being expressed in hosts such as *Escherichia coli* can be used. However, it is desirable to use plasmids having a ribosome-binding sequence and an initiation codon as spaced at suitable intervals therebetween (for example, by 6 to 18 bases).

The L-proline-4-hydroxylase gene includes any and every gene that codes for an L-proline-4-hydroxylase. However, it is desirable that the bases constituting the DNA sequence of the gene are suitably substituted in order that the substituted DNA sequence can be constituted of codon most suitable for expression in the host microorganisms to be used. As examples of L-proline-4-hydroxylase genes where the constitutive bases have been substituted to modify them into codons most suitable for their expression, mentioned are the nucleotide sequence of Sequence No. 16, etc.

Transcription terminator sequences are not always necessary for the expression of the genes of the present invention.

However, it is desirable that a transcription terminator sequence is arranged just after the structural gene.

Examples of the host cells usable in the present invention include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Bacillus subtilis, Bacillus amyloliquefacines, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium acetoacidophilum* ATCC13870, *Microbacterium ammoniaphilum* ATCC15354, etc.

When the yeast strain is used as the host cell, for example, YEp13 (ATCC37115), YEp24 (ATCC37051), YCp50 (ATCC37419), etc. can be used as the expression vector.

As the promoter, any one that can be expressed in the host cell of the yeast strain can be used. As examples of the promoters, promoters of glycolytic genes such as hexose kinase, gal 1 promoter, gal 10 promoter, heat shock protein promoter, MFα1 promoter, and CUP 1 promoter can be used.

As examples of the host cells, *Saccharomyces cerevisae, Schizosaccharomyces pombe, Kluyveromyces lactis, Trichosporon pullulans,* and *Schwanniomyces alluvius,* etc. can be mentioned.

When the animal cells are used as the host cell, for example, pcDNA I/Amp, pcDNA I and pcDM8 (all commercially available from Funakosi Co.), etc. can be used as the expression vector.

As the promoter, any one that can be expressed in the host cell of animal cells can be used. For example, a promoter of an IE (immediate early) gene of human CMV, etc. can be used. An enhancer of the IE gene of human CMV may be used together along with the promoter.

As examples of the host cells, Namalwa, HBT5637 (Japanese Published Unexamined Patent Application No. 299/88), COS-cell, CHO-cell, etc. can be used.

To introduce DNA into animal cells, any and every method capable of introducing DNA into animal cells can be employed herein. For example, employable are electroporation methods [see Miyaji et al., Cytotechnology, 3, 133 (1990)], calcium phosphate methods (see Japanese Published Unexamined Patent Application No. 227075/90), lipofection methods [see Philip L. Felgner, et al., Proc. Natl. Acad. Sci., USA, 84, 7413 (1987)], etc. The resulting transformants can be collected and cultivated in accordance with the methods described in Japanese Published Unexamined Patent Application Nos. 227075/90 and 257891/90.

Of the hosts mentioned above, preferred are those having a reinforced proline biosynthesis activity.

To reinforce the proline biosynthesis activity of the hosts, employable are a means of increasing the number of copies of the gene that codes for an enzyme participating in the biosynthesis of L-proline (hereinafter referred to as "proline biosynthesis gene") in the hosts, a means of mutating a proline biosynthesis gene that shall be subjected to feedback inhibition with proline to produce a mutant gene that codes for an enzyme which takes part in proline biosynthesis, to which the feedback inhibition with proline is greatly reduced (hereinafter referred to as "proline biosynthetase"), followed by introducing the resulting mutant gene into the hosts, a means of removing the proline decomposition activity from the hosts, and also a combination of any of these means.

The proline biosynthesis gene, or the mutant gene that codes for a proline biosynthetase can exist on the chromosomes of the hosts or can also exist on the vectors, such as plasmids, in the hosts.

Any gene can be used so long as the gene codes for a proline biosynthetase. For example, it includes a gene proB74 such as that mentioned hereinabove, a gene DHP$^r$proB, etc.

In the case of having any of the proline biosynthesis gene and the mutant gene which codes for a proline biosynthetase coexist with a L-proline-4-hydroxylase gene on vectors such as plasmids in the same host, the both genes can exist either on a single plasmid or on plural, co-existable plasmids.

For the plasmids of *E. coli*, for example, the combination of such co-existable plasmids include a colicin E1 family plasmid (e.g., pBR322) and a pACYC family plasmid; a colicin E1 family plasmid and an F-factor family plasmid; and a colicin family E1 plasmid and an R-factor family plasmid.

To make the host express the proline biosynthesis gene, employable is the same process as that mentioned hereinabove for the expression of L-proline-4-hydroxylase gene.

The host which loses proline decomposition activity can be obtained by selecting the strain which forms white colony on the Pro-TTC plate [Appl. Environ. Microbiol., 33, 434 (1977)] after processing the host with the mutagen.

It is known that *E. coli* shall lose its ability of assimilating proline if a transposon is inserted into a suitable site of its put gene. For *E. coli*, therefore, a transposon is introduced thereinto, and a mutant *E. coli* that has lost its proline decomposition activity also can be selected through a chemical resistance test and a cell-growing test on a Pro-TTC plate.

The mutant that has lost its proline decomposition activity due to the introduction of a transposon thereinto can be subjected to P1 transduction to thereby transfer its characteristic not having a proline decomposition activity into a different strain.

The thus obtained transformant is cultivated by an ordinary cultivation method.

The medium for cultivating these microbial transformants such as *Escherichia coli,* yeast strains or the like may be any of natural media and synthetic media that contain carbon sources, nitrogen sources, inorganic salts, etc. that may be assimilated by the microorganisms.

Any carbon sources that can be assimilated by the microorganisms may be used. Examples of the carbon source include carbohydrates such as glucose, fructose, sucrose, molasses containing these components, starch and starch hydrolyzates; organic acids such as acetic acid and propionic acid; and alcohols such as ethanol and propanol.

As the nitrogen sources, ammonia, ammonium salts of inorganic and organic acids such as ammonium chloride, ammonium sulfate, ammonium acetate and ammonium phosphate, other nitrogen-containing compounds, peptone, meat extracts, yeast extracts, corn steep liquor, casein hydrolyzates, soybean cakes, soybean cake hydrolyzates, cultured fermented cells, their digested products, etc. may be used.

As inorganic salts, potassium dihydrogen phosphate, dipotassium hydrogen phosphate, magnesium phosphate, magnesium sulfate, sodium chloride, ferrous sulfate, manganese sulfate, copper sulfate, calcium carbonate, etc. may be used.

The cultivation is conducted under aerobic conditions, for example, with shaking culture or submerged-aerial stirring culture. The temperature for the cultivation is 15° to 40° C. The period for the cultivation is usually 16 to 96 hours. During the cultivation, the pH of the medium is kept at 3.0 to 9.0. The pH is adjusted using inorganic or organic acids, alkaline solutions, urea, calcium carbonate, ammonia or the like.

L-Proline is suitably added to the media in such a manner that its concentration may be from 5 to 1000 mM, preferably from 20 to 200 mM, whereby the intended L-proline-4-hydroxylases can be produced more efficiently.

Antibiotics such as ampicillin, tetracycline or the like may be added to the medium during the cultivation, if required.

For the cultivation of the microorganisms which are transformedwith the expression vector using the inducible promoter, inducers may be added to the medium, if required. For example, in cultivation of microorganisms transformed with the expression vector using lac promoter, isopropyl-β-D-thiogalactopyranoside (IPTG) may be added to the medium. In cultivation of microorganisms transformed with the expression vector using trp promoter, indoleacrylic acid (IAA) may be added to the medium.

As the medium for cultivating the transformants which are obtains by using the animal cells as a host cell, RPMI1640 medium and Eagle's MEM medium which are generally used or these culture media containing a fetal bovine serum can be used.

The cultivation of the cells is conducted in the presence of 5% $CO_2$. The temperature for the cultivation is preferably 35° to 37° C., and the period for the cultivation is usually 3 to 7 days.

L-proline is suitably added to the media in such a manner that its concentration may be from 5 to 1000 mM, preferably from 20 to 200 mM, whereby the intended L-proline-4-hydroxylases can be produced more efficiently.

Antibiotics such as kanamycin, penicillin or the like may be added to the medium during the cultivation, if required.

A considerable amount of L-proline-4-hydroxylase is produced and accumulated in the thus-cultivated transformants in comparison to the microorganism strain used as the gene source, such as Dactylosporangium sp. RH1 or the like. Thus, the isolation and purification of the enzyme or the production of trans-4-hydroxy-L-proline from L-proline using the enzyme can be performed far more efficiently in comparison to the production of trans-4-hydroxy-L-proline from L-proline using the non genetically-engineered microorganism as the gene source, such as Dactylosporangium sp. RH1 or the like.

The production of L-proline-4-hydroxylase in the transformants can be carried out by adding the culture, the cells or the treated cells to an aqueous medium suitable for the enzymatic reaction together with L-proline, a divalent iron ion and 2-ketoglutaric acid, and adding a surfactant or an organic solvent, if required, to determine trans-4-hydroxy-L-proline produced. With respect to the activity of the L-proline-4-hydroxylase of which the formation is confirmed in the cell, the activity of the enzyme for producing 1 nmol of trans-4-hydroxy-L-proline for 1 minute under the following conditions is defined as 1 unit (U). The microorganism cells and the animal cells are here called cells.

Measurement of L-proline-4-hvdroxvlase activity

The cells, the treated cells or the enzyme preparation are added to 240 mM MES [2-(N-morphorino) ethanesulfonic acid] buffer containing 12 mM L-proline, 24 mM 2-ketoglutaric acid, 4 mM ferrous sulfate and 8 mM L-ascorbic acid to make 250 μl in total. The mixture is kept at 35° C. for 10 minutes. The reaction mixture is heated at 100° C. for 2 minutes to stop the reaction, and the amount of trans-4-hydroxy-L-proline produced in the reaction mixture is determined by HPLC.

For the determination, any method capable of determining the amount of trans-4-hydroxy-L-proline maybe employed. For instance, generally usable are (1) a post-column derivatization method and (2) a pre-column derivatization method as mentioned above.

The enzyme may be isolated and purified in a usual manner from the culture of the transformant in which the formation of L-proline-4-hydroxylase is confirmed in the cultivated cell as mentioned above. For instance, the culture broth of the transformant is centrifuged to collect the cultivated cells therefrom, and the cells are washed and then disrupted by an ultrasonic cell disrupter, a French press, a Manton-Gauline homogenizer, a Dyno mill or the like to obtain a cell-free extract. The purified enzyme prepatarion can be obtained by ammonium sulfate precipitation, anion exchange chromatography such as diethylaminoethyl (DEAE) Sepharose or the like, hydrophobic chromatography such as butyl-Sepharose, phenyl-Sepharose or the like, gel filtration, electrophoresis such as isoelectric point electrophoresis, and so on from the supernatant of the cell-free extract obtained by centrifugation.

The cultivated transformant cells that have been identified to contain the L-proline-4-hydroxylase as formed therein can be cultivated under the same conditions as above, under which the transformant cells were cultivated, to thereby make the cells produce and accumulate trans-4-hydroxy-L-proline in the cells, and the thus-produced trans-4-hydroxy-L-proline can be collected from the culture to obtain it.

If the transformant cell derived from host cell which has the ability of producing L-proline from saccharide sources and accumulating it in the cultures and where such cells are used, it is possible to produce trans-4-hydroxy-L-proline even if L-proline is not added to the media during the cultivation of the cells therein. However, it is desirable to suitably add to the media L-proline at a concentration of from 5 to 1000 mM, preferably from 20 to 200 mM, whereby the intended trans-4-hydroxy-L-proline can be produced more efficiently.

The transformant cells as derived from a transformant host having a reinforced proline biosynthesis activity can efficiently produce trans-4-hydroxy-L-proline without adding L-proline thereto.

If the transformant cells have the ability of producing 2-ketoglutaric acid from saccharide sources and accumulating it in the cultures and where such cells are used, it is possible to produce trans-4-hydroxy-L-proline even if 2-ketoglutaric acid is not added to the media during the cultivation of the cells therein. Where such transformant cells are used, saccharide sources such as glucose may be suitably added to the media to make the cells produce and accumulate 2-ketoglutaric acid in the cultures, whereby the intended trans-4-hydroxy-L-proline can be produced more efficiently. Where, on the other hand, transformant cells not having the ability of producing 2-ketoglutaric acid from saccharide sources are used, 2-ketoglutaric acid may be added to the media during the incubation of the cells, if desired.

If desired, 2-ketoglutaric acid and divalent iron ions may be added to the media during the cultivation of the transformant cells.

To produce trans-4-hydroxy-L-proline, also employable is another method to be mentioned below using, as the enzyme source, the cultures of the transformant cells where the formation of L-proline-4-hydroxylases has been identified, the cells isolated from the cultures, or the products as obtained by processing the cells.

The method to produce trans-4-hydroxy-L-proline is as follows. The cultures of the transformant cells, the cells isolated from the culture, or the products as obtained by processing the cells are added to aqueous media suitable for enzymatic reaction, along with L-proline, divalent iron ions and 2-ketoglutaric acid and optionally with surfactants and organic solvents, thereby converting L-proline into trans-4-hydroxy-L-proline, and thereafter the resulting trans-4-hydroxy-L-proline is collected from the reaction mixtures to obtain it.

As examples of the processed cells, dried cells, lyophilized cells, surfactant-treated cells, enzymatically-treated cells, ultrasonically-treated cells, mechanically-ground cells, mechanically-compressed cells, solvent-treated cells, fractionated cell proteins, immobilized cells, immobilized materials obtained by processing their cells, etc. can be used. The enzyme preparation obtained by extraction from the cells having L-proline-4-hydroxylase activity, purified products of these enzymes, and immobilized products thereof can also be used.

As examples of the aqueous medium, water, buffers such as phosphates, carbonates, acetates, borates, citrates and tris-buffers, alcohols such as methanol and ethanol, esters such as ethyl acetate, ketones such as acetone, and amides such as acetamide can be mentioned.

As examples of the surfactant, cationic surfactants such as polyoxyethylene-stearylamine (for example, Nymeen S215 produced by Nippon Oils & Fats Co.), cetyltrimethylammonium bromide, Cation FB, Cation F2-40E, etc.; anionic surfactants such as sodium oleylamidosulfate, Newrex TAB, and Rapizole 80.; ampholytic surfactants such as polyoxyethylene-sorbitan monostearate (for example, Nonion ST221) or the like.; and also other tertiary amines PB, hexadecyldimethylamine, etc. can be mentioned. Any and every surfactant that promotes the reaction may be employed. The concentration of the surfactant is usually from 0.1 to 50 mg/liter, preferably from 1 to 20 mg/liter.

As examples of the organic solvent, toluene, xylene, aliphatic alcohols, benzene and ethyl acetate can be mentioned. The concentration of the organic solvent is usually from 0.1 to 50 $\mu$l/ml, preferably from 1 to 20 $\mu$l/ml.

The reaction may be conducted during the cultivation of the transformant having the activity of L-proline-4-hydroxylase, or may also be conducted after the completion of the cultivation, in the aqueous medium using the cells, the treated cells, the purified enzyme or the crude enzyme prepared from the culture.

The amount of the enzyme added to the reaction mixture is determined depending on the amount of the substrate used. Usually, it may be from 1.0 to 10,000,000 U/liter, preferably from 1,000 to 3,000,000 U/liter of the aqueous medium. In case of using the cells or the treated cells of the microorganism, the concentration of wet cells is usually from 1 to 300 g/liter.

The reaction is usually conducted at a temperature from 15° to 50° C. at a pH from 6.0 to 9.0 for 1 to 96 hours.

The concentration of L-proline used in the reaction may be from 1 mM to 2M. L-Proline can be supplied by adding L-proline itself to the reaction mixture, or adding the culture of the microorganism which can produce and accumulate L-proline from sugar source. Further, if a microorganism having the ability of producing L-proline from a sugar source is used as the host microorganism of the transformant, L-proline produced from a sugar source by the host microorganism can be used in the reaction. That is, L-proline produced by the transformant derived from the host microorganism having the ability of producing L-proline is converted into trans-4-hydroxy-L-proline in the culture broth using L-proline-4-hydroxylase produced by the transformant, whereby trans-4-hydroxy-L-proline can be produced in the culture without the addition of L-proline.

The divalent iron ion is required for the reaction. This divalent iron ion is ordinarily used in a concentration of from 1 to 100 mM. Any divalent iron ion can be used so long as does not inhibit the reaction. As examples of the divalent iron ion, sulfates such as ferrous sulfate; chlorides such as ferrous chloride; ferrous carbide; and organic acid salts such as citrates, lactates and fumarates can be mentioned. When the divalent iron ion is contained in the cells, the treated cells or the reaction mixture, the divalent iron need not be added.

2-Ketoglutaric acid itself may be added to the reaction mixture or may be supplied from a compound which can be converted into 2-ketaglutaric acid by the metabolic activity of the cells or the treated cells used. As examples of such a compound, saccharides such as glucose; amino acids such as glutamic acid; and organic acids such as succinic acid can be mentioned. These compounds may be used singly or in combination.

Trans-4-hydroxy-L-proline is recovered from the culture or the aqueous medium by any ordinary separation method, for example, column chromatography using an ion-exchange resin, etc. by crystallization, etc.

The structure of the thus-recovered trans-4-hydroxy-L-proline can be identified by ordinary analytical method such as $^{13}$C-NMR spectrum, $^{1}$H-NMR spectrum, mass spectrum, specific rotation or the like.

The trans-4-hydroxy-L-proline produced by the present invention can be determined quantitatively by the above-mentioned post-column derivatization method or pre-column derivatization method.

The present invention is illustrated more specifically by referring to the following Examples.

EXAMPLE 1

(1) Production of Trans-4-hydroxy-L-proline by Dactylosporangium sp. RH1

SR3 medium comprising 1.0% glucose, 1.0% soluble starch, 0.5% yeast extract, 0.5% tryptone, 0.3% meat extract and 0.05% magnesium 25 phosphate was adjusted to pH 7.2 with 6N NaOH, was put in test tubes (diameter 25 mm×length 200 mm) in an amount of 10 ml each and sterilized at 120° C. for 20 minutes. One loopful of cells of Dactylosporangium sp. RH1, that had grown in HT-agar plate medium comprising 1% soluble starch, 0.2% NZ amine, 0.1% yeast extract, 0.1% meat extract and 1.5% agar, adjusted to 7.2 with 6N NaOH, and sterilized at 120° C. for 20 minutes, was inoculated into the above-mentioned SR3 medium in each test tube, cultivated at 28° C. for 2 days with shaking. The resulting culture was used as a seed culture in the following steps.

Separately, Df1 medium comprising 5% soluble starch, 1.5% soybean meal, 0.05% monopotassium phosphate, 0.05% magnesium sulfate 7 hydrate and 0.5% calcium carbonate, and adjusted to pH 7.0 with 6N NaOH, was put in test tubes (diameter 25 mm×length 200 mm) in an amount of 10 ml each and sterilized at 120° C. for 20 minutes. One ml of the above-mentioned seed culture was inoculated in the medium in each test tube under germ-free condition and cultivated at 28° C. for 2 days with shaking. The thus-obtained culture was centrifuged at 7000 x g for 10 minutes at 4° C. The cells thus separated were washed with 80 mM TES [N-tris(hydroxymethyl)methyl-2-aminoethanesulfonic acid] buffer (pH 7.5) and then recentrifuged. 150 mg of the thus-obtained wet cells was suspended in 1.5 ml of a reaction mixture which had been prepared by adding 1.4% (v/v) of Nymeen solution [prepared by adding 4 g of Nymeen S-215 (produced by Nippon Oils & Fats Co.) to 10 ml of xylene] to 80 mM TES buffer (pH 7.5) containing 4 mM L-proline, 8 mM 2-ketoglutaric acid, 4 mM L-ascorbic acid and 2 mM ferrous sulfate] and the mixture was allowed to stand at 30° C. for 2 hours to carry out the enzymatic reaction.

After the reaction, the cells were removed from the reaction mixture by centrifugation, and the amount of trans-4-hydroxy-L-proline produced in the supernatant was determined.

The determination was carried out by a post-column derivatization method by HPLC under the conditions mentioned below. To identify the intended product, the resulting product was eluted from the column and reacted with NBD in the column line to form its NBD-derivative and the derivative was determined by fluorophotometry.

Conditions for determination by HPLC

[1] Apparatus used:
High Performance Liquid Chromatography Device
(produced by Shimadzu Seisakusho K.K.)

| | |
|---|---|
| Chromatopac | CR6A |
| System controller | SCL-6B |
| Autoinjector | SIL-6B |
| Liquid Chromatograph Pump | LC-6A |
| Column Oven | CTO-6A |
| Chemical Reaction Box | CRB-6A |
| Spectrofluorometric Detector | RF-550A |

[2] Column Used:
SUMCHIRAL OA5000 (diameter 4.5 mm x length 250 mm, produced by Sumika Chemical Analysis Service Limited)

[3] Conditions for Analysis:

| | | |
|---|---|---|
| 1) | Mobile Phase: aqueous solution of copper sulfate | 1 mM |
| 2) | Flow Rate of Mobile Phase: | 1.0 ml/min |
| 3) | Column Temperature: | 38° C. |
| 4) | Buffer: 0.3M boric acid buffer (pH 9.6) 25 mM ethylenediaminetetraacetic acid | |
| 5) | Flow Rate of Buffer: | 0.2 ml/min |
| 6) | NBD Solution: methanol solution of | 0.5 g/liter |
| 7) | Flow Rate of NBD Solution: | 0.5 ml/min |
| 8) | Reaction Temperature: | 60° C. |
| 9) | Reaction Time: | about 3 min |
| 10) | Wavelength for Detection: excitation wavelength emission wavelength | 503 nm 541 nm |
| 11) | Sample: | 10 μl |

As a result of the determination, it was verified that 249 μM (32.6 mg/liter) of trans-4-hydroxy-L-proline was produced in the reaction mixture.

(2) Productionof Trans-4-hydroxy-L-proline by Dactylosporangium sp. RH1

SR3 medium was put into a test tube in amount of 10 ml and sterilized at 120° C. for 20 minutes. One loopful of cells of Dactylosporangium sp. RH1 that had grown in an HT-agar plate medium were inoculated in the medium and cultivated at 28° C. for 2 days with shaking. The culture thus prepared was used as a seed culture.

Df3 medium was put into another test tube in amount of 10 ml and sterilized at 120° C. for 20 minutes. One ml of the seed culture prepared above was inoculated in the Df3 medium under germ-free conditions and cultivated at 28° C. for 2 days with shaking. The resulting culture was centrifuged at 8000 rpm and at 4° C. for 10 minutes. The cells thus separated were washed with 80 mM TES buffer (pH 7.5) and then centrifuged. 150 mg of the wet cells thus obtained were suspended in 1.5 ml of a reaction mixture [which is 80 mm TES buffer (pH7.5) comprising 4 mM L-proline, 8 mM α-ketoglutaric acid, 4 mM L-ascorbic acid and 2 mM ferrous sulfate, to which was added 1.4% (v/v) of Nymeen solution (which is prepared by dissolving 4 g of Nymeen S-215 (produced by Nippon Oils & Fats Co.) in 10 ml of xylene)] and reacted at 30° C. for 30 minutes. After the reaction, the cells were separated from the reaction mixture through centrifugation, and the amount of hydroxyproline formed in the supernatant was quantitatively determined, from which the L-proline-4-hydroxylase activity of the cells of Dactylosporangium sp. was determined.

As a result of the determination, it was verified that 84 $\mu$M (11.0 mg/liter) of trans-4-hydroxy-L-proline was produced in the reaction mixture. The L-proline-4-hydroxylase activity of the cell was 0.028 U/mg wet cells/min.

EXAMPLE 2

Purification of Trans-4-hydroxy-L-proline

The seed cultivation was carried out in the same manner as in (1) of Example 1, using 2 liter Erlenmeyer flasks each containing 200 ml of SR3 medium. Df1 medium was put in 5 liter jar fermenters in an amount of 2 liters each and sterilized at 120° C. for 20 minutes. The seed culture was inoculated in the Df1 medium in each jar fermenter under germ-free condition and cultivated under the condition of 700 rpm and 1 vvm, at 28° C. for 2 days. During the cultivation, the pH of the medium was not adjusted. The thus-obtained culture medium was centrifuged at 7,000 x g for 10 minutes at 4° C. to obtain wet cells in an amount of 75 g per liter of the culture. A part of the wet cells was washed with a physiological saline at 4° C. and recentrifuged. If desired, the thus-obtained wet cells were frozen and stored at −80° C., and the frozen cells were thawed before use.

Separately, 400 g of the wet cells was suspended in 2 liters of the reaction mixture described in Example 1, put in a 3 liter beaker, and the enzymatic reaction was carried out at 30° C. for 4 hours with stirring.

After the reaction, the cells were removed from the reaction mixture by centrifugation, and trans-4-hydroxy-L-proline produced in the supernatant was determined. It was verified that 480 $\mu$M (63.0 mg/liter) of trans-4-hydroxy-L-proline was produced in the reaction mixture.

The reaction mixture was adjusted to pH 4.5, and the supernatant separated from the reaction mixture was passed through a column packed with 200 ml of an ion-exchange resins Diaion SKIB ($NH_4^+$ type, produced by Mitsubishi Kasei Corp.). The fraction containing trans-4-hydroxy-L-proline was concentrated under reduced pressure and then passed through a column packed with 20 ml of an ion-exchange resin, Diaion PA412 (OH-type, produced by Mitsubishi Kasei Corp.). The fraction containing trans-4-hydroxy-L-proline was concentrated under reduced pressure, and adjusted to pH 9.6. 10 volume % of o-phthal aldehyde (hereinafter referred to as OPA) solution (0.075 g of OPA/ml ethanol solution) and 2 volume % of β-mercaptoethanol solution (10% v/v aqueous solution) were added thereto. The mixture was then allowed to stand at 60° C. for 5 minutes, whereby impurities of primary amino acids contained therein were reacted with OPA. The resulting mixture was passed through a column packed with 10 ml of Sepabeads SP207 (produced by Mitsubishi Kasei Corp.), to separate trans-4-hydroxy-L-proline from the impurities of OPA-derivatized primary amino acids. The fraction containing trans-4-hydroxy-L-proline was concentrated under reduced pressure and again passed through a column packed with 20 ml of an ion-exchange resin, Diaion PA412 (OH-type, produced by Mitsubishi Kasei Corp.) to separate a fraction containing trans-4-hydroxy-L-proline. The final fraction was concentrated and dried to obtain 78 mg of white crystals of trans-4-hydroxy-L-proline. The yield of the product was 62%. The white crystals were analyzed, and the data of its $^{13}$C-NMR spectrum, $^1$H-NMR spectrum, mass spectrum and specific rotation were found to coincide with a standard sample of trans-4-hydroxy-L-proline (produced by Nacalai Tesque Co.).

EXAMPLE 3

(1)Production of Trans-4-hydroxy-L-proline by Amycolatopsis sp. RH2

SR3 medium was put in test tubes (diameter 25 mm×length 200 mm) in an amount of 10 ml each and sterilized at 120° C. for 20 minutes. One loopful of cells of Amycolatopsis sp. RH2 that had grown in HT-agar plate medium was inoculated in the above-mentioned medium in each test tube, cultivated at 28° C. for 2 days with shaking, and used as a seed culture in the following steps.

Separately, Df1 medium was put in test tubes (diameter 25 mm×length 200 mm) in an amount of 10 ml each and sterilized at 120° C. for 20 minutes. One ml of the seed culture was inoculated in the medium in each test tube under germ-free condition and cultivated at 28° C. for 2 days with shaking. The thus-obtained culture was centrifuged at 7000 x g for 10 minutes at 4° C. The cells thus separated were washed with 100 mM TES buffer (pH 7.5) and then recentrifuged. In 1.5 ml of a reaction mixture which had been prepared by adding 1.4% (v/v) of Nymeen solution [prepared by adding 4 g of Nymeen S-215 (produced by Nippon Oils & Fats Co.) to 10 ml of xylene] to 100 mM TES buffer (pH 7.5) containing 5 mm L-proline, 5 mM 2-ketoglutaric acid, 5 mM L-ascorbic acid and 1 mM ferrous sulfate, 100 mg of the thus-obtained wet cells was suspended and the mixture was allowed to stand at 30° C. for 3 hours.

After the reaction, the cells were removed from the reaction mixture by centrifugation, and hydroxyprolines produced in the supernatant were determined.

The determination of trans-4-hydroxy-L-proline was conducted in the same manner as in Example 1.

It was verified that 25 $\mu$M (3.3 mg/liter) of trans-4-hydroxy-L-proline was produced in the reaction mixture.

(2)Production of Trans-4-hydroxy-L-proline by Streptomyces

The amount of trans-4-hydroxy-L-proline and the L-proline-4-hydroxylase activity of *Streptomyces griseoviridis* JCM4250 and *Streptomyces daghestanicus* JCM4365 was determined in the same manner as in (2) of Example 1. In this example, however, a Df4 medium [comprising 2.5% of glycerol, 2.5% of glucose, 1.5% of soybean meal, 0.005% of monopotassium phosphate, 0.05% of magnesium sulfate 7-hydrate and 0.5% of calcium carbonate and adjusted to pH 7.0 with 6N NaOH] was used in place of the Df1 medium.

As a result of the determination, it was verified that 60 $\mu$M of trans-4-hydroxy-L-proline was produced in the reaction mixture when the cells of *Streptomyces griseoviridis* JCM4250 was used. The L-proline-4-hydroxylase activity of the cell was 0.020 U/mg wet cells/min. The amount of trans-4-hydroxy-L-proline and the L-proline-4-hydroxylase activity of *Streptomyces daghestanicus* JCM4365 were 27μM and 0.009U/mg wet cells/min, respectively.

EXAMPLE 4

Purification of Trans-4-hydroxy-L-proline

The seed cultivation was carried out in the same manner as in (1) of Example 3, using 2 liter Erlenmeyer flasks each containing 200 ml of SR3 medium. Df1 medium was put in 5 liter jar fermenters in an amount of 2 liters each and sterilized at 120° C. for 20 minutes. The seed culture was inoculated in the Df1 medium in each jar fermenter under germ-free condition and cultivated under the condition of 700 rpm and 1 vvm, at 28° C. for 2 days. During the cultivation, the pH of the medium was not adjusted. The thus-obtained culture medium was centrifuged at 7,000 x g for 10 minutes at 4° C. to obtain wet cells in an amount of 75 g per liter of the culture. In 2 liters of the reaction mixture described in Example 3, 400 g of the wet cells were suspended, and put in a 3 liter beaker, and the reaction mixture was allowed to stand at 30° C. for 4 hours with stirring.

The supernatant was adjusted to pH 4.5, and passed through a column packed with 200 ml of an ion-exchange resin, Diaion SK18 ($NH_4^+$ type, produced by Mitsubishi Kasei Corp.). The fraction containing trans-4-hydroxy-L-proline was concentrated under reduced pressure and then passed through a column packed with 20 ml of an ion-exchange resin, Diaion PA412 (OH-type, produced by Mitsubishi Kasei Corp.). The fraction containing trans-4-hydroxy-L-proline was concentrated under reduced pressure, adjusted to pH 9.6, and 10 volume % of OPA solution (0.075 g/ml ethanol solution) and 2 volume % of β-mercaptoethanol solution (10% v/v aqueous solution) were added thereto. The mixture was then allowed to stand at 60° C. for 5 minutes, whereby impurities of primary amino acids contained therein were reacted with OPA. The resulting mixture was passed through a column packed with 10 ml of Sepabeads SP207 (produced by Mitsubishi Kasei Corp.), to separate trans-4-hydroxy-L-proline from the impurities of the OPA-derivatized primary amino acids. The fraction containing trans-4-hydroxy-L-proline was concentrated under reduced pressure and again passed through a column packed with 20 ml of an ion-exchange resin, Diaion PA412 (OH-type, produced by Mitsubishi Kasei Corp.) to separate a fraction containing trans-4-hydroxy-L-proline. The final fraction was concentrated and dried to obtain 4.8 mg of white crystals of trans-4-hydroxy-L-proline. The yield of the product was 62%.

The white crystals were analyzed, and the data of its $^{13}$C-NMR spectrum, $^1$H-NMR spectrum, mass spectrum and specific rotation were found to coincide with those of a standard sample of trans-4-hydroxy-L-proline (produced by Nacalai Tesque Co.).

EXAMPLE 5

Isolation and Purification of L-proline-4-hydroxylase (1) Preparation of Cell-free Extract Six hundred grams of the wet cells obtained in Example 2 was suspended in 3 liters of Buffer A [50 mM TAPS buffer (pH 9.0) containing 2 mM DTT, 0.2 mM EDTA and 20% (v/v) of glycerol] while cooling with ice. The resulting suspension was milled by a Dyno-mill (produced by Willy A Bachofen Maschinenfabrik, Basel, Switzerland) to disrupt the cells. The thus-disruped cell suspension was subjected to centrifugation at 6,500 x g at 4° C. for 30 minutes to separate the supernatant.

The subsequent operations were conducted under cooling with ice at a temperature of 4° C. or lower. (2) Isolation and purification by various types of Column Chromatography (2)-1 STREAMLINE The supernatant obtained in the previous step was passed through a STREAMLINE® (produced by Pharamacia Co.) filled with 300 ml of DEAE adsorbent that had been equilibrated with Buffer A, whereupon a fraction containing the L-proline-4-hydroxylase was eluted with Buffer A containing 0.3M NaCl.

(2)-2 DEAE Sepharose Column Chromatography

The active fraction obtained in the previous step was diluted three times with Buffer A and passed through a DEAE Sepharose column (5 cm×15 cm) that had been equilibrated with Buffer A. The column was washed with Buffer A, and the fraction containing the enzyme was eluted with Buffer A having a linear concentration gradient of NaCl of 0 to 0.3M.

(2)-3 Butyl Sepharose Column Chromatography

NaCl was added to the active fraction obtained in the previous step until an NaCl concentration was 3M. The mixture was passed through a butyl Sepharose column (Butyl Sepharose 4 Fast Flow, 2.6 cm×13 cm) that had been equilibrated with Buffer A containing 3M NaCl. The enzyme was stepwise eluted with four kinds of buffers each having a different NaCl concentration, Buffer A containing 3M NaCl, Buffer A containing 1.98M NaCl, Buffer A containing 0.99M NaCl and Buffer A containing no NaCl, in this order or from the eluent buffer having a higher NaCl concentration to that having a lower NaCl concentration.

(2)-4 Phenyl Sepharose Column Chromatography

NaCl was added to the active fraction obtained in the previous step until the concentration of NaCl was 3M. The mixture was passed through a phenyl Sepharose column (Phenyl Sepharose HP Hiload 16/10, 1.6 cm×10cm) that had been equilibrated with Buffer A containing 3M NaCl. The column was washed with Buffer A containing 3M NaCl, and the fraction containing the enzyme was eluted with Buffer A.

(2)-5 Dye Affinity Column Chromatography

The active fraction obtained in the previous step was de-salted, using a PD-10 column (produced by Pharmacia Co.), and the resulting fraction was passed through a Reactive Red 120 column (1 cm×12.7 cm; produced by Sigma Co.) that had been equilibrated with Buffer A. The column was washed with Buffer A, and the fraction containing the enzyme was eluted with Buffer A having a linear concentration gradient of NaCl of 0 to 1.5M.

(2)-6 Resource Q Column Chromatography

The active fraction obtained in the previous step was de-salted, using a PD-10 column (produced by Pharmacia Co.) that had been equilibrated with Buffer B [50 mM TAPS buffer (pH 8.0) containing 2 mM DTT, 0.1% (v/v) of Tween 20 and 20% (v/v) of glycerol], and the resulting fraction was passed through a RESOURCE™ Q column (1 ml; produced by Pharmacia Co.) that had been equilibrated with Buffer B. The fraction containing the enzyme was eluted with Buffer B having a liner concentration gradient of NaCl of 0 to 0.2M.

Summaries of the isolation and purification of the L-proline-4-hydroxylase are shown in Table 5.

TABLE 5

Summaries of Isolation and Purification of
L-proline-4-hydroxylase

| Fraction | Total Protein (mg) | Total Activity (U) | Relative Activity (U/mg of protein) | Yield (%) |
|---|---|---|---|---|
| Cell-free Extract | 13,330 | 11,000 | 0.83 | 100 |
| STREAMLINE | 4,875 | 4,880 | 1.00 | 44.4 |
| DEAE Sepharose | 353 | 3,820 | 10.8 | 34.7 |
| Butyl Sepharose | 35.1 | 1,310 | 37.3 | 11.9 |
| Phenyl Sepharose | 1.44 | 814 | 565.3 | 7.4 |
| Color Affinity | 0.212 | 366 | 1,726 | 3.3 |
| Resource Q | 0.100 | 384 | 3,840 | 3.5 |

EXAMPLE 6

Properties of L-proline-4-hydroxylase (1) Analysis by Electrophoresis

The purified enzyme preparation obtained in Example 5 was analyzed by sodium dodecylsulfate-polyacrylamide gel electrophoresis (using polyacrylamide gel PAGEL NPU-12.5L produced by Atto Co. and SDS-PAGE Molecular Weight Standard, Broad Range produced by Biorad Co.). As a result, it was verified that the enzyme was composed of almost homogeneous sub-units having a molecular weight of about 32,000±5,000 daltons.

(2) Properties Relating to Enzyme Reaction

The enzyme was subjected to substrate omission and addition tests using the reaction mixtures mentioned below, to investigate the compounds indispensable to the enzyme reaction of the enzyme for hydroxylating the 4-position of L-proline, the promoters for the reaction and the inhibitors against the reaction.

The reaction mixture was composed of 80 mM TES buffer (pH 7.5), 4 mML-proline, 8 mM 2-ketoglutaric acid, 2 mM ferrous sulfate, 4 mM L-ascorbic acid, 2 mg/ml catalase and a pre-determined amount of the pure enzyme, the total volume being 500 μl. The reaction was initiated by addition of the enzyme and continued for 15 minutes at 30° C. The reaction was stopped by heating the reaction mixture at 100° C. for 2 minutes. The amount of trans-4-hydroxy-L-proline formed in the reaction mixture was determined by the pre-column derivatization method. One hundred microliter of 0.3M boric acid buffer (pH 10.7), 4 μl of aqueous solution of 10% (v/v) mercaptoethanol and 16 μl of ethanol solution of 5% (w/v) OPA were added to 100 μl of the reaction mixture, and the mixture was allowed to stand at 60° C. for 30 seconds. In addition, 50 μl of ethanol solution of 2% (W/V) NBD was added thereto and the mixture was allowed to stand at 60° C. for 40 minutes. The reaction was stopped by adding 30 μl of 1N HCl to the reaction mixture, and the precipitates formed were removed therefrom by centrifugation and filtration. The trans-4-hydroxy-L-proline formed-bythe reaction was quantitatively determined by HPLC analysis.

The HPLC for the determination was carried out under the following conditions:

Mobile Phase: 10 mM Citric Acid (pH 4.0)/Methanol=3/1 (v/v)

Flow Rate: 1 ml/min

Column: YMC Pack ODS AQ-312 (produced by YMC Co., 6×150 mm)

Column Temperature: 50° C.

Detection: Fluorophotometry (excitation wavelength: 503 nm, emission wavelength: 541 nm)

The test results verified that L-proline, 2-ketoglutaric acid and $Fe^{++}$ ion are indispensable for the enzyme reaction for hydroxylating L-proline at the 4-position of L-proline, that L-ascorbic acid promotes the reaction and that $Zn^{++}$ ion, $Cu^{++}$ ion and EDTA inhibit the reaction.

The test results are shown in Table 6.

TABLE 6

Investigation of Components Influencing
Enzyme Reaction of L-Proline-4-Hydroxylase

| Components in Reaction Mixture | Added (+)[2] Not Added (−) | Relative Activity[3] |
|---|---|---|
| Basic Reaction Mixture[1] |  | 100 |
|  | − Pure Enzyme | 0 |
|  | − L-Proline | 0 |
|  | − 2-Ketoglutaric Acid | 0 |
|  | − $Fe^{++}$ | 0 |
|  | − L-Ascorbic Acid | 51 |
|  | − Catalase | 93 |
|  | + 5 mM EDTA | 0 |
|  | + 1 mM $Zn^{++}$ | 6 |
|  | + 1 mM $Cu^{++}$ | 13 |

[1] The standard reaction mixture was 80 mM TES buffer (pH 7.5) containing 4 mM L-proline, 8 mM 2-ketoglutaric acid, 2 mM ferrous sulfate, 4 mM L-ascorbic acid, 2 mg/ml catalase and a pre-determined amount of the pure enzymer the total volume being 500 μl. The reaction was carried out at 30° C. for 15 minutes.
[2] "(+)" means that the reaction mixture contained the component shown in the table. "(−)" means that the reaction mixture did not contain the component shown in the table. The concentration shown in the table means the concentration of the component in the reaction mixture.
[3] The activity is indicated as relative activity to the activity in the standard reaction mixture of being defined as 100.

(3) Optimum pH Range

In the above-mentioned method of determining the enzyme activity of the L-proline-4-hydroxylase, the reaction was conducted while the buffer component in the reaction mixture was changed to sodium acetate buffer at pH of 3.5 to 5.5, it was changed to MES buffer at pH of 5.5 to 6.50, it was changed to TES buffer at pH of 7.0 to 7.5, it was changed to TAPS buffer at pH of 8.0 to 9.0, and it was changed to CAPSO buffer at pH of 9.5 to 11.0. As a result, the enzyme had an activity of more than 90% of the maximum activity thereof at pH ranging from pH 6.0 to pH 7.0. The detailed test results are shown in Table 7.

TABLE 7

Optimum pH Range for the Enzyme Reaction

| pH | Relative Activity[1] |
|---|---|
| 3.5 | 2.9 |
| 4.0 | 4.4 |
| 4.5 | 5.9 |
| 5.0 | 10.3 |
| 5.5 | 41.2 |
| 6.0 | 97.0 |
| 6.5 | 100.0 |
| 7.0 | 91.2 |
| 7.5 | 75.0 |
| 8.0 | 47.1 |
| 8.5 | 44.0 |
| 9.0 | 29.4 |
| 9.5 | 7.4 |

TABLE 7-continued

Optimum pH Range for the Enzyme Reaction

| pH | Relative Activity[1] |
|---|---|
| 10.0 | 4.4 |
| 10.5 | 0 |
| 11.0 | 0 |

[1]The activity is indicated as relative activity to the activity in pH 6.5 of being 100.

(4) Stable pH Range

The enzyme was kept in the presence of 50 mM of a buffer (sodium acetate buffer at pH of 3.5 to 5.5, MES buffer at pH of 5.5 to 6.5, TES buffer at pH of 7.0 to 7.5, TAPS buffer at pH of 8.0 to 9.0, CAPSO buffer at pH of 9.5 to 11.0), 2 mM DTT and 20% (v/v) of glycerol, at 4° C. for 24 hours, and then its activity was determined. The enzyme kept at pH ranging from 6.5 to 10.0 had an activity of 90% or more of the original activity of the enzyme before the test. Accordingly, the enzyme was kept stable at pH ranging from 6.5 to 10.0.

(5) Optimum Temperature Range

In the above-mentioned method of determining the enzyme activity of the L-proline-4-hydroxylase, the reaction was carried out at temperatures ranging from 15° to 50° C. for 15 minutes. As a result, the enzyme had an activity of 90% or more of the maximum activity thereof at temperatures ranging from 30° to 40° C. The detailed test results are shown in Table 8.

TABLE 8

Optimum Temperature Range for the Enzyme Reaction

| Reaction Temperature (°C.) | Relative Activity[1] |
|---|---|
| 15 | 28 |
| 20 | 41 |
| 25 | 60 |
| 30 | 91 |
| 35 | 100 |
| 40 | 96 |
| 45 | 68 |
| 50 | 32 |

[1]The Activity is indicated as a relative activity to the maximum activity of being defined as 100.

(6) Stable Temperature Range

The enzyme was kept in 50 mM TAPS buffer (pH 9.0) containing 2 mM DTT, 0.1% (v/v) of Tween 20 and 20% (v/v) of glycerol at a temperature ranging from 0° to 60° C. for 30 minutes and thereafter the activity of the enzyme was determined. As a result, the enzyme was inactivated at 50° C. or higher for 30 minutes.

(7) N-terminal Amino Acid Sequence

The enzyme was analyzed, using Protein Sequencer Model PPSQ-10 (produced by Shimadzu Seisakusho K.K.), to determine the N-terminal amino acid sequence of the enzyme. The result was as follows:

Sequence No. 1:

| (N-terminal) | 1 | MetLeuThrProThrGluLeuLysGlnTyr |
|---|---|---|
| | 11 | ArgGluAlaGlyTyrLeuLeuIleGluAsp |
| | 21 | GlyLeuGlyProArgGluVal |

EXAMPLE 7

Production of Trans-4-hydroxy-L-proline

The enzyme reaction with purified L-proline-4-hydroxylase obtained in Example 5 was carried out. The reaction mixture was composed of 200 mM MES buffer (pH 6.5), 20 mM L-proline, 20 mM 2-ketoglutarate, 5 mM L-ascorbic acid, 2 mM ferrous sulfates and 90 U of purified enzyme preparation in total volume of 50 μl. The reaction was carried out at 35° C. for 30 min. As a result of the reaction, 12.9 mM (1.7 g/l) of trans-4-hydroxyL-proline was produced in the reaction mixture.

EXAMPLE 8

Preparation of partial DNA fragment of the gene encoding L-proline-4-hydroxylase protein derived from Dactylosporangium sp. RH1

(1) Isolation of Chromosomal DNA of Dactylosporangium sp. RH1:

Chromosomal DNA of Dactylosporanaium sp. RH1 was isolated in the usual manner as follows. SK#2 medium (comprising 0.25% glucose, 1.0% soluble starch, 0.25% yeast extract, 0.25% peptone, 0.15% meat extract, 0.01% potassium dihydrogen phosphate and 0.03% magnesium sulfate, and adjusted to pH 7.6 with 6N NaOH) containing 5% mannitol and 0.05% glycine, was put into test tubes in an amount of 10 ml each, and sterilized at 120° C. for 20 minutes. One loopfui of cells of Dactylosporangium sp. RH1 which had grown in TH-agar plate medium (comprising 1% soluble starch, 0.2% NZ amine, 0.1% yeast extract, 0.1% meat extract and 1.5% agar, adjusted to pH7.2 with 6N NaOH and sterilized at 120° C. for 20 minutes), was inoculated in the above-mentioned medium, and cultivated at 28° C. for 3 days with shaking.

The culture was centrifuged, and the obtained cells were washed with 10 ml of a 10.3% sucrose solution, and suspended in 6 ml of TS comprising 10.3% sucrose, 50 mM tris•HCl (pH 8.0) and 25 mM EDTA. One milliliter of a lysozyme solution (50 mg/ml•TS) was added thereto, and the mixture was incubated at 37° C. for 60 minutes. Subsequently, 0.6 ml of a Proteinase K (produced by Sigma Co.) solution (2 mg/ml•TS) was added to the lysozyme-treated solution, and gently stirred. Further, 3.6 ml of a 3.3% (w/v) SDS solution was added thereto while gently mixing, and the mixture was incubated at 37° C. for 60 minutes. The mixture was heated at 50° C. for 30 minutes, and then cooled with water. An equal amount of TE [containing 10 mM tris•HCl (pH 8.0) and 1 mM EDTA] saturated phenol-chloroform (1/1, v/v) was added thereto, and the mixed solution was moderately shaken for 30 minutes. After the centrifugation, the upper layer was taken, and again subjected to extraction with the mixture of TE saturated phenol-chloroform. The extract was centrifuged, and an equal amount of chloroform was then added to the upper layer, and mixed. The mixture was recentrifuged. The upper layer was taken, and 20 μl of an RNase A aqueous solution (10 mg/ml) heat-treated at 100° C. for 10 minutes was added to the upper layer. The mixture was incubated at 37° C. for 45 minutes. To the RNase A-treated solution were added ⅒ volume of a 5M NaCl aqueous solution and ¼ volume of 50% PEG6000, and gently mixed. The mixture was allowed to stand overnight while being cooled with ice. After the mixed solution was centrifuged at 12,000 rpm for 10 minutes, the supernatant was discarded completely, and the precipitate was dissolved in 5 ml of TE. After ⅒ volume of a 3M sodium acetate solution and ⅓₀ volume of a 66 mM magnesium chloride solution were added thereto and mixed, 2.2 volumes of cold ethanol was added, and gently mixed. After the mixed solution was centrifuged at 10,000 rpm for 10 minutes, the supernatant was discarded, and the precipitate was washed twice with 70% cold ethanol. The precipitate containing 250 μg of chromosomal DNA was dissolved in TE and used in the subsequent experiment as chromosomal DNA.

(2) Preparation of partial DNA fragment of L-roline-4-hydroxylase gene

The sense strand mixed DNA primer indicated in Sequence o. 4 corresponding to amino acids Nos. 1 to 6 of an amino acid sequence indicated in Sequence No. 1 and an anti-sense strand mixed DNA primer indicated in Sequence No. 5 corresponding to amino acids Nos. 19 to 24 indicated in Sequence No. 1 were synthesized using 380A•DNA Synthesizer manufactured by Applied Biosystems.

Using the above-synthesized DNA primers and Dactylosporangium sp. RH1 chromosomal DNA as a template, the PCR was conducted by a Program Temp Control System PC-700 manufactured by K.K. Astec. The reaction was conducted using 20 μl of a reaction mixture having the following formulation.

Formulation of the reaction mixture:

| | |
|---|---|
| Dactylosporangium sp. RH1 chromosomal DNA | 22 ng/μl |
| sense strand mixed DNA primer | 10 μM |
| anti-sense strand mixed DNA primer | 10 μM |
| Pfu DNA polymerase produced by Stratagene | 0.125 U/μl |
| DMSO | 10% |
| tris.HCl (pH 8.2) | 20 mM |
| KCl | 10 mM |
| ammonium sulfate | 6 mM |
| magnesium chloride | 2 mM |
| Triton X-100 | 0.1% |
| bovine serum albumin | 10 ng/μl |

After the completion of an incubation at 96° C. for 5 minutes, a three step incubation, namely at 96° C. for 2 minutes, at 37° C. for 1 minute and at 72° C. for 1 minute was repeated for a total of five times. Further, a three step incubation, namely at 96° C. for 2 minutes, at 50° C. for 1 minute and at 72° C. for 1 minute was repeated for a total of 35 times. The reaction mixture was subjected to electrophoresis with 15% polyacrylamide (PAGEL NPU-15L produced by Atto Co.), and a band of 71 bp was recovered using da Vinci Kun (Pen Touch Recovery NB-7000 Model) manufactured by Nippon Eido K.K. The recovered DNA fragment (71 bp) was inserted into a Sma I site of pUC18 using a Sure Clone Ligation Kit produced by Pharmacia Co., and the nucleotide sequence was determined by a nucleotide sequencing kit (Taq DyeDeoxy™ Terminator Cycle Sequencing Kit produced by Applied Biosystems) . The determined nucleotide sequence of the DNA fragment of 71 bp is shown in Sequence No. 6. The amino acid sequence presumed from the nucleotide sequence of the DNA fragment of 71 bp completely agreed with the N-terminal amino acid sequence of the purified enzyme indicated in Sequence No. 1.

EXAMPLE 9

Cloning of a DNA fragment containing L-proline-4-hydroxylase gene:

(1) Preparation of a DIG probe

A digoxigenin (DIG) labeled DNA fragment of 71 bp was prepared using a PCR DIG Labelling Kit produced by Boehringer Mannheim.

The PCR was conducted using 2.5 U of Pfu DNA Polymerase (produced by Stratagene), 5 μl of x10 Buffer for Pfu DNA polymerase (produced by Stratagene), 5 μl of DMSO, 5 μl of x10 PCR DIG Mix (produced by Boehringer Mannheim), 1 μl of a dilute solution obtained by diluting to ten times the DNA solution containing the fragment of 71 bp formed in the PCR and recovered after the electrophoresis with polyacrylamide gel in (2) of Example 8, and 50 μl of a reaction mixture containing 10 μM of the sense strand synthetic DNA indicated in Sequence No.4 and 10μM of the anti-sense strand synthetic DNA indicated in Sequence No. 5. After the completion of an incubation at 96° C. for 5 minutes, a three step incubation, namely at 96° C. for 2 minutes, at 50° C. for 1 minute and at 72° C. for 1 minute was repeated to a total of 35 times. The reaction mixture was subjected to electrophoresis with 12.5% polyacrylamide gel to identify the formation of an amplification fragment of 71 bp. The fragment was recovered from the gel in the same manner as in (2) of Example 8, and used as a probe.

(2) Southern hybridization

Restriction endonuclease Xho I (produced by Takara Shuzo, 36 U) was added to 10 μg of chromosomal DNA of Dactylosporangium sp. RH1, and the mixture was incubated at 37° C. for 2 hours. DNA was cleaved, and subjected to electrophoresis with agarose gel using the probe obtained in (1) of Example 9 and DIG Luminescent Detection Kit produced by Boehringer Mannheim, and Southern hybridization was conducted according to the method described in a manual attached to the Kit.

That is, after the completion of the agarose gel electrophoresis, the agarose gel was shaked gently in 0.25N hydrochloric acid for 20 minutes, and then dipped in a mixture of 0.5M sodium hydroxide and 1.5M sodium chloride for 50 minutes and further in a mixture of 2M sodium chloride and 1M tris•HCl (pH 5.0) for 25 minutes. While sucking the gel at 7.5 mmHg by means of a Genopirator Pump AE-6680P produced by Atto Co. and a Genopirator AE-6680C also produced by Atto Co., Hybond-N$^+$ Film (produced by Amersham) was blotted with the gel in SSC at a concentration of 20 times (formulation of SSC at a concentration of 1 time - 150 mM sodium chloride and 15 mM sodium citrate). After thecompletion of the blotting, the film was dried at 80° C. for 10 minutes, and then crosslinked using FUNA-UV-LINKER FS-800 (produced by Funakoshi). The thus-obtained film was dipped in 10 ml of a hybridization buffer (solution obtained by dissolving 50% v/v formamide, 2% blocking reagent, 0.1% w/v N-laurylsarcosine and 0.02% w/v SDS in SSC at a concentration of 5 times) of a DIG Luminescent Detection Kit at 42° C. for 1 hour, and then dipped in a probe solution [obtained by adding 3 μl of the probe obtained in (1) of Example 9 to 200 μl of a hybridization buffer, treating the mixture at 95° C. for 2 minutes, and then adding the hybridization buffer to adjust the total amount to 1.5 ml] overnight at 42° C. The thus-obtained film was further washed twice with 25 ml of 0.1% SDS containing SSC at a concentration of 2 times at room temperature for 5 minutes each, and then washed twice with 25 ml of 0.1% SDS containing SSC at a concentration of 0.1 time at 68° C. for 15 minutes each.

The thus-washed film was treated with a washing buffer [Buffer 1 (0.1M maleic acid, 0.15M sodium chloride, pH 7.5) containing 0.3% w/v Tween-20] at room temperature for 1 to 5 minutes, with 50 ml of Buffer 2 (Buffer 1 containing 1% blocking reagent) at room temperature for 30 minutes, with Buffer 2 containing 10 ml of 1 μm anti-digoxigenin-AP Fab at room temperature for 30 minutes, twice with 50 ml of Buffer 2 at room temperature for 30 minutes each, with 10 ml of Buffer 3 (a buffer containing 0.1M tris•HCl, 0.1M sodium chloride and 50 mM magnesium chloride, pH 9.5) at room temperature for from 2 to 5 minutes, and with 5 ml of Buffer 3 containing 50 μl of Lumigen PPD at room temperature for 5 minutes in this order. Subsequently, water was removed from the film quickly over a filter paper, wrapped with Saran Wrap, and then allowed to stand at 37° C. for 15 minutes. The resulting film was exposed at room temperature for 30 minutes using a Hyperfilm-ECL (produced by Amersham).

It was found that the DNA fragment which had hybridized strongly with the probe was present at a position of approximately 5.5 kb.

(3) Fractionation of chromosomal DNA

Restriction endonuclease Xho I (produced by Takara Shuzo Co., Ltd., 360 U) was added to 100 μg of chromosomal DNA of Dactylosporangium sp. RH1, and the mixture was incubated at 37° C. for 2 hours. After DNA was cleaved, an equal amount of a mixture of TE saturated phenol-chloroform was added thereto, and mixed. After the mixture was centrifuged, the upper layer was taken, and mixed gently with 2.2 volumes of cold ethanol. The mixture was centrifuged at 10,000 rpm for 10 minutes. After the supernatant was discarded, the precipitate was washed twice with 70% cold ethanol to obtain an ethanol precipitate (hereinafter the procedure for obtaining the ethanol precipitate using the mixture of TE saturated phenol-chloroform mixture and the cold ethanol referred to as "ethanol precipitation"). The precipitate was dissolved in 120 μl of TE, and the mixture was subjected to agarose gel electrophoresis. After the completion of the electrophoresis, a DNA fraction of approximately 5.5 kb was extracted from the agarose gel and purified using Prep-A-gene (produced by Biorad Co.) to obtain approximately 7 μg of the Xho I cleaved chromosomal DNA fraction.

(4) Construction of phage library

Using an undigested λZAPII Cloning Kit produced by Stratagene, a phage library was formed as follows.

Restriction endonuclease Xho I (produced by Takara Shuzo Co., Ltd., 36 U) was added to 5 μg of λZAPII DNA, and the mixture was incubated at 37° C. for 3 hours. After DNA was cleaved, the ethanol precipitate was obtained by ethanol precipitation. After the ethanol precipitate was dissolved in 35 μl of TE, the solution was dephosphorylated using Alkaline Phosphatase (Calf Intestine) produced by Takara Shuzo Co., Ltd. according to the method described in a manual attached thereto. After the completion of the dephosphorylation, the ethanol precipitate was obtained by the ethanol precipitation. The thus-obtained Xho I-cleaved λZAPII DNA (0.36 μg) was reacted with 0.35 μg of Xho I-cleaved chromosomal DNA obtained in (3) of Example 9 at 26° C. for 2.5 hours using a ligation kit (TAKARA Ligation Kit produced by Takara Shuzo Co., Ltd.) to ligate the two. Ethanol was added to the reaction mixture, and the resulting DNA precipitate was dissolved in 4 μl of TE. The DNA was further packaged in λphage particles using a Gigapack II Gold Packaging Extract produced by Stratagene.

Meanwhile, *E. coli* XL1-Blue MRF' strain (produced by Stratagene) was inoculated in 3 ml of LB medium (solution obtained by dissolving 10 g of bactotryptone, 5 g of bacto-yeast extract and 5 g of NaCl in 1 liter of distilled water and sterilized at 120° C. for 20 minutes) containing 0.2% (w/v) maltose and 10 mM magnesium sulfate, and cultivated at 30° C. for 16 hours. After the completion of the cultivation, the cells were collected by centrifugation, and suspended in 10 mM of a sterilized magnesium sulfate solution such that the absorbance at 600 nm was approximately 0.5.

Two-hundred microliters of the above-obtained cell solution was mixed with 10 μl of a packaging solution, and the mixed solution was then incubated at 37° C. for 15 minutes. To the mixed solution were added 50 μl of a solution (250 mg X-Gal/ml•dimethylformamide) containing 3 ml of LB soft agar medium (obtained by adding an agar to LB medium such that the amount of the agar was 0.6%), 15 μl of a 0.5M IPTG aqueous solution and 50 μl of a solution (250 mg X-Gal/ml•dimethylformamide) containing X-Gal (5-bromo-4-chloro-3-indolyl-β-D-galactoside). The mixture was put on LB agar medium (obtained by adding an agar to LB medium such that the amount of the agar was 1.8%), and cultivated overnight at 37° C.

Approximately 5,000 colorless plagues were obtained and used as a phage library.

(5) Selection of an intended clone

The plaque having the intended clone was selected from the above-mentioned phage library as follows.

The plaques appearing on the LB agar medium were shifted onto a nylon film (Nytran produced by Schleicher & Schuell) washed with SSC at a concentration of 5 times. Subsequently, the film was allowed to stand on a filter paper immersed with 0.5M sodium hydroxide and 1.5M sodium chloride. Further, the film was allowed to stand on a filter paper immersed with 1.5M sodium chloride and 0.5M tris•HCl (pH 8.0) twice for 2 minutes each and on a filter paper immersed with SSC at a concentration of 2 times for 2 minutes each. Subsequently, the resulting film was dried at 80° C. for 30 minutes. The dried film was washed with 0.1% SDS containing SSC at a concentration of 2 times and then with SSC at a concentration of 2 times, and air-dried.

The detection was conducted using the DIG probe obtained in (1) of Example 9 and a DIG Luminescent Detection Kit produced by Boehringer Mannheim according to the method described in (1) of Example 9. Consequently, one positive plaque having the intended clone was detected.

(6) Identification of a clone

A portion of approximately 1 cm² around the positive plaque was cut out. One milliliter of SM (a medium containing 5.8 g/l sodium chloride, 2 g/l magnesium chloride, 0.01% gelatin, and 50 mM tris•HCl, pH 7.5) and 20 μl of chloroform were added thereto. The mixture was stirred thoroughly, and then centrifuged. The thus-obtained supernatant was used as a phage extract.

A sense strand DNA primer indicated in Sequence No. 7 corresponding to Nucleotides Nos. 13 to 32 of the nucleotide sequence described in Sequence No. 6 and an anti-sense strand DNA primer indicated in Sequence No. 8 corresponding to Nucleotides Nos. 53 to 71 of the nucleotide sequence indicated in Sequence No. 6 (provided that the nucleotide corresponding to Nucleotide No. 66 indicated in Sequence No. 6 was G) were synthesized by means of 380A•DNA Synthesizer manufactured by Applied Biosystems.

Using 5 μl of the phage extract, the sense strand DNA primer indicated in Sequence No. 7 and the anti-sense strand DNA primer indicated in Sequence No. 8, the PCR was conducted according to the method described in (3) of Example 8 to obtain a DNA fragment of 59 bp. The DNA fragment was analyzed by electrophoresis with 12.5% polyacrylamide, and identified as the intended clone.

The procedures described in (4) to (6) of Example 9 were repeated except that the above-obtained phage extract was used instead of the packaging liquid shown in (4) of Example 9 to purify the intended clone.

(7) Formation of a plasmid by in vivo excision of the phage DNA

Formation of a plasmid by in vivo excision of the phage DNA in the extract obtained in (6) of Example 9 was conducted using an undigested λZAPII Cloning Kit produced by Stratagene according to a method described in a manual attached thereto is described below.

E. coli XL1-Blue MRF' strain was inoculated in 3 ml of LB medium containing 0.2% (w/v) maltose and 10 mM magnesium sulfate according to a method described in (4) of Example 9 and was cultivated at 30° C. for 16 hours. After the completion of the cultivation, the culture was centrifuged, and the obtained cells were suspended in 10 mM magnesium sulfate solution such that the absorbance at 600 nm was approximately 1.0. To 200 µl of the cell solution were added 100 µl of the phage extract obtained in (6) of Example 9 and 1 µl of an ExAssist Helper Phage (produced by Stratagene), and the mixture was incubated at 37° C. for 15 hours. To this reaction mixture was added 3 ml of 2xYT (obtained by dissolving 10 g sodium chloride, 10 g yeast extract and 16 g of bactotryptone in 1 liter of distilledwater, and sterilized at 120° C. for 20 minutes), and the mixture was shaken at 37° C. for 2 hours. The resulting solution was heated at 70° C. for 20 minutes, and centrifuged to obtain a supernatant. One microliter of the supernatant was added to 200 µl of E. coli SOLR strain cultivated in the same manner as E. coli XL1-Blue MRF' strain. The mixture was incubated at 37° C. for 15 minutes, then spread on LB agar medium containing 50 µg/ml of ampicillin, and cultivated overnight at 37° C. A positive colony was selected from the colonies grown on the agar medium according to the method described in (6) of Example 9 except that the colonies were used instead of the phage extract.

A plasmid was extracted from the thus-obtained positive colony in a usual manner, and the structure thereof was identified by digestion with restriction endonucleases. The thus-obtained plasmid pRH71 had a structure in which the Xho I-cleaved DNA fragment having a size of approximately 5.5 kb was inserted in the Xho I site of pBluescript SK(–) as shown in FIG. 1.

(8) Determination of nucleotide sequence

Figure 1:
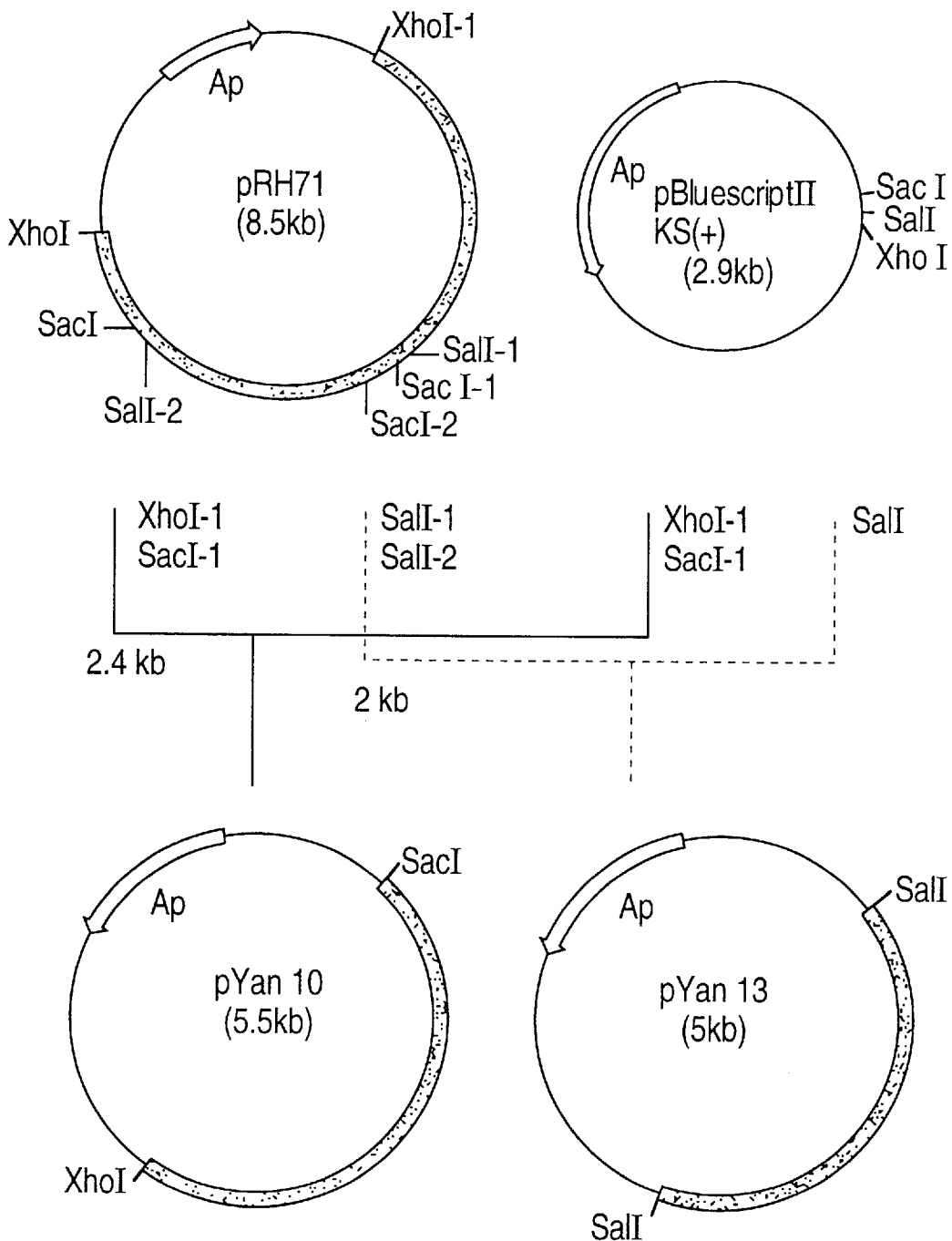
FIG. 1 shows a restriction enzyme map of plasmid pRH71 and the steps of constructing plasmids pYan10 and pYan13.

From the Xho I fragment having a size of approximately 5.5 kb inserted in the above-obtained pRH71, aSac I-Xho I fragment having a size of approximately 2.4 kb (fragment to be cleaved with Xho I-1 and Sac I-1 in FIG. 1) and a Sac I fragment having a size of approximately 2 kb (fragment to be cleaved with Sac I-1 and Sac I-2) were cleaved with the respective restriction endonucleases and thereby obtained, and subcloned at the Sac I-Xho I cleavage site and the Sac I cleavage site of pBluescript KS(+) to obtain plasmids pYan10 and pYan13 as shown in FIG. 1.

Using a deletion kit for kilosequences produced by Takara Shuzo Co., Ltd., deletion mutant plasmids were constructed from pYan10 according to a method described in a manual attached thereto.

A nucleotide sequence of the Sac I-Xho I fragment having the size of approximately 2.4 kb in the deletion plasmid was determined using a sequence determination kit (Taq DyeDeoXy™ Terminator Cycle Sequencing Kit produced by Applied Biosystems).

With respect to pYan13, deletion mutant plasmids were constructed, and the nucleotide sequence determination was conducted in the same manner as mentioned above to determine the nucleotide sequence of the Sac I-Sac I fragment (fragment to be cleaved with Sac I-1 and Sac I-2 in FIG. 1) in the Sac I fragment having the size of approximately 2 kb.

The nucleotide sequence of the Sac I-Xho I fragment (fragment to be cleaved with Xho I-1 and Sac I-2 in FIG. 1) 2707b is indicated in Sequence No. 9.

In the thus-determined nucleotide sequence, the nucleotide sequence (corresponding to Nucleotide Nos. 264 to 1079 in Sequence No. 9) represented by Sequence No. 3, which encodes a protein composed of 272 amino acids indicated in Sequence No.2 was present. This amino acid sequence included the N-terminal amino acid sequence indicated in Sequence No. 1 which was determined using purified L-proline-4-hydroxylase. Thus, it was identified that the intended L-proline-4-hydroxylase gene was present in the obtained Xho I fragment having a size of approximately 5.5 kb.

EXAMPLE 10

Construction of an L-proline-4-hydroxylase expression plasmid (1) Construction of an expression plasmid using trp promoter(Ptrp)

A sense strand DNA primer indicated in Sequence No. 10 and an anti-sense strand DNA primer indicated in Sequence No. 11 were synthesized by 380A•DNA Synthesizer manufactured by Applied Biosystems. The PCR was conducted using the synthetic DNA's as the primers and pRH71 as a template. The reaction was conducted in the same manner as in Example 8 using 20 µl of a reaction mixture containing 0.1 µg of pRH71, 2 µM sense strand DNA primer and 2 µM anti-sense strand DNA primer. That is, after incubation at 96° C. for 5 minutes, a three step incubation, namely at 96° C. for 2 minutes, at 58° C. for 1 minute and at 75° C. for 1 minute was repeated for a total of 30 times. The reaction mixture was subjected to agarose gel electrophoresis. After it was identified that an amplified fragment of 844 bp encoding the structural gene of L-proline-4-hydroxylase was formed, the amplified fragmentwas extracted from the agarose gel in a usual manner, and recovered using Prep-A-gene produced by Biorad Co. Both terminals of the DNA fragment of 844 bp recovered were cleaved with Hind III and Bam HI, and an ethanol precipitate was then obtained by the ethanol precipitation. The ethanol precipitate was dissolved in 5 µl of TE.

Plasmid pTrS30DNA containing Ptrp was cleaved by Hind III and Bam HI. The L-proline-4-hydroxylase structural gene fragment treated with Hind III and Bam HI was inserted into the cleavage site via the ligation kit produced by Takara Shuzo Co., Ltd. Using the thus-obtained plasmid, E. coli XL1-Blue MRF' strain was transformed in a usual manner. The transformant was spread on LB agar medium containing 50 µg/ml of ampicillin, and then cultivated overnight at 37° C. The plasmid was extracted from the colony of the grown transformant in a usual manner, and the structure of the plasmid was identified by digestion with a restriction endonuclease.

As a result, plasmid pTr14 in which the DNA fragment containing the structural gene of L-proline-4-hydroxylase was inserted in the same direction as the transcription direction of Ptrp was obtained as shown in FIG. 2.

(2) Construction of an expression plasmid using tac promotor(Ptac)

An expression plasmid using Ptac was constructed in the same manner as in (1) of Example 10.

A sense strand DNA primer as indicated in Sequence No. 12 and an anti-sense strand DNA primer as indicated in Sequence No. 13 were synthesized. Using the synthetic DNAs as the primers and pRH71 as a template, the PCR was conducted to obtain an amplification fragment of 846 bp containing the structural gene of L-proline-4-hydroxylase. This fragment was cleaved by Eco RI and Hind III, then inserted into the Eco RI-Hind III cleavage site of plasmid pBTacl containing Ptac (produced by Boehringer Mannheim), and transformed into *E. coli* XL1-Blue MRF' stain.

Plasmid pTc4OH in which the DNA fragment containing the structural gene of L-proline-4-hydroxylase was inserted in the same direction as the transcription direction of Ptac was obtained from the resulting transformant as shown in FIG. 3.

(3) Construction of an Expression Plasmid Using Ptrpx2

In the same manner as in (1) of Example 10, an amplified fragment containing the structural gene of L-proline-4-hydroxylase was recovered, processed with restriction enzymes and an ethanol precipitate was then obtained by ethanol precipitation. The ethanol precipitate was dissolved in 5 µl of TE.

An ATG vector, pTrS32 formed by combining a synthetic linker and plasmid pKYP200, which is composed of a basic plasmid pBR322 together with two promoters Ptrps connected in series (Ptrpx2), was cleaved with Hind III and Bam HI. Hind III-Bam HI fragment containing the structural gene of L-proline-4-hydroxylase in the above was inserted into the Hind III-Bam HI cleavage site of the vector, using a ligation kit (produced by Takara Shuzo Co.).

Using the thus-obtained plasmid, *E. coli* XL1-Blue MRF' strain were transformed in a usual manner. The transformant was spread on LB-agar medium containing 50 µg/ml of ampicillin and then cultivated thereon overnight at 37° C. The plasmid was extracted from the grown colonies of the trans formant cells in a usual manner, and the structure of the plasmid was identified by digestion with restriction enzyme. The part of the structural gene of L-proline-4-hydroxylase was sequenced to determine its nucleotide sequence, using a base sequencing kit (Taq DyeDeoxy™ Terminator Cycle Sequencing Kit, produced by Applied Biosystems Co.), which revealed that the nucleotide sequence of the structural gene is indicated by Sequence No. 3.

As a results, plasmid pTr2-4OH in which the DNA fragment encoding the structural gene of L-proline-4-hydroxylase was inserted in the same direction as the transcription direction of Ptrpx2 was obtained shown in FIG. 4.

A DNA as indicated in Sequence No. 14 and a DNA as indicated in Sequence No. 15 were synthesized, using 380A•DNA Synthesizer (produced by Applied Biosystems Co.). These DNAs were so designed that their 3' terminals of 25 bp are complementary to each other. These DNAs each have a nucleotide sequence coding for the N-terminal site of Dactylosporangium sp. RH1-derived L-proline-4-hydroxylase protein, in which the nucleotide sequence has been site-specifically substituted to make it a codon that is the most suitable in its expression in *Escherichia coli*.

Using these synthetic DNA's as primers and templates, PCR was conducted. The reaction was conducted, using 20 µl of a reaction mixture comprising 0.5 U of Pfu DNA polymerase (produced by STRATAGENE Co.), 2 µl of x10 buffer for Pfu DNA polymerase, 2 µl of DMSO, 1 µl of 2.5 mM DNTP, 2 µM of the synthetic DNA of Sequence No. 14 and 2M of the synthetic DNA of Sequence No. 15. The reaction mixture was incubated at 96° C. for 5 minutes. Subsequently, a three step incubation, namely at 96° C. for 2 minutes, at 50° C. for 1 minute and at 75° C. for 1 minute was repeated for a total of 35 times. After the resulting reaction mixture was subjected to 15% polyacrylamide gel electrophoresis, the formation of an amplified fragment of 107 bp was identified. The amplified fragment was recovered from the gel in the same manner as in (2) of Example 8. The both terminals of the thus-recovered DNA fragment of 107 bp were cleaved with Hind III and Sal I, and the thus-processed fragment was recovered using MERmaid Kit (produced by Bio. Inc.). The amount of the liquid thus recovered was 16 µl.

Plasmid pTr2-4OH DNA was cleaved with Bam HI and Pvu II. The reaction mixture was subjected to agarose gel electrophoresis, through which the formation of two fragments was identified. Of these, the longer fragment having the structural gene of L-proline-4-hydroxylase was isolated, using Prep-A-Gene (produced by Biorad Co.), and its terminals were blunted using a blunting 35 kit (produced by Takara Shuzo Co.) and then cyclized using a ligation kit (produced by Takara Shuzo Co.). With the thus-obtained plasmid, *E. coli* JM109 strain was transformed in a usual manner, and the resulting transformant cells were spread on LB-agar medium containing 50 µg/ml of ampicillin and then cultivated thereon overnight at 37° C. Aplasmidwas extracted from the grown colonies of the transformant cells in a usual manner, and its structure was identified through digestion with restriction enzyme. As a result of the above, obtained was plasmid pTr2-4OHΔ, which is lacking for a part of the sequence of pTr2-4OH (see FIG. 5).

Plasmid pTr2-4OHΔ DNA was cleaved with Hind III and Sal I. The PCR-amplified fragment that had been processed with Hind III and Sal I in the above was inserted into the Hind III-Sal I cleavage site of the plasmid, using a ligation kit (produced by Takara Shuzo Co.) . With the thus-obtained plasmid, cells of *E. coli* XLl-Blue MRF' strain were transformed in a usual manner, and the resulting transformant cells were spread on LB-agar medium containing 50 µg/ml of ampicillin and then cultivated thereon overnight at 37° C. A plasmid was extracted from the grown colonies of the transformant cells in a usual manner, and its structure was identified through digestion with restriction enzyme. The part of the plasmid into which the PCR-amplified fragment had been inserted was sequenced, using a base sequencing kit (Taq DyeDeoxy™ Terminator Cycle Sequencing Kit, produced by Applied Biosystems Co.), to determine its nucleotide sequence, which revealed that the nucleotide sequence is indicated by Sequence No. 16.

As a result of the above, obtained was plasmid pWFH1 containing the structural gene DNA fragment coding for the amino acid sequence which is entirely the same as the Dactylosporangium sp. RH1-derived L-proline-4-hydroxylase except that from the 5'-terminal to the Sal I site of the structural gene is partly different from the Dactylosporangium sp. RHl-derived nucleotide sequence, in the same direction as transcription direction of Ptrpx2 (see FIG. 6).

EXAMPLE 11

Production of L-proline-4-hydroxylase by Transformant

*E. coli* ATCC12435 was transformed with plasmids, pTr14, pTc4OH and pWFH1 as obtained in Example 10 to obtain transformants, *E. coli* ATCC12435/pTr14, *E. coli* ATCC12435/pTc4OH and *E. coli* ATCC12435/pWFH1, respectively. *E. coli* ATCC12435/pTr14 and *E. coli* ATCC12435/pTc4OH were separately inoculated each in 3 ml of an LB medium containing 50 µg/ml of ampicillin and cultivated therein overnight at 30° C. with shaking.

*E. coli* ATCC12435/pWFH1 was inoculated in 50 ml of a Med4 medium [1% of polypeptone (produced by Nippon Pharmaceuticals Co.), 0.5% of yeast extract (produced by Difco Co.) and 1% of NaCl] containing 100 μg/ml of ampicillin and cultivated therein for 16 hours at 30° C. The resulting culture was used as a seed culture, which was inoculated in a 5 liter jar fermenter filled with 2 liters of a Med6 medium (2% of glucose, 1% of ammonium sulfate, 0.1% of $K_2HPO_4$, 0.2% of NaCl, 0.05% of $MgSO_4$, 0.0278% of $FeSO_4$, 0.0015% of $CaCl_2$, 0.4% of polypeptone), to which was added 200 nM of L-proline. The mixture was subjected to the cultivation in the jar fermenter under the condition of 400 rpm and 1 vvm, at 30° C. for 48 to 72 hours. During the incubation, glucose and L-proline were suitably added to the medium in such a manner that glucose was always present in the medium and L-proline could be at about 50 mM therein, and the lowermost limit of the pH of the medium was controlled at 6.5 by adding $NH_4OH$ to the medium.

The thus-obtained cultures were centrifuged respectively to separate the cells.

The L-proline-4-hydroxylase activity of the cells was measured under the conditions mentioned below. If desired, the cells can be frozen and stored at −20° C., and the frozen cells can be thawed and used in the measurement of the enzymatic activity.

The cells separated as above were added to 250 μl of a reaction mixture [comprising 12 mM L-proline, 24 mM 2-ketoglutaric acid, 4 mM ferrous sulfate and 8 mM L-ascorbic acid in 240 mM MES buffer (pH 6.5)] in an amount of 4% (w/v) in terms of the wet cells and reacted at 35° C. for 10 minutes. The reaction mixture was heated at 100° C. for 2 minutes to stop the reaction.

After the reaction was stopped, the resulting reaction mixture was centrifuged, and 100 μl of 0.3M borate buffer (pH 10.7), 4 μl of 10% (v/v) mercaptoethanol and 16 μl of 5% (w/v) o-phthalaldehyde in ethanol were added to 100 μl of the resulting supernatant and the reaction mixture was kept at 60° C. for 30 seconds. Then, 50 μl of 2% (w/v) NBD in ethanol was added to the reaction mixture and kept at 60° C. for 40 minutes. Thirty microliters of 1N HCl was added to the reaction mixture to stop the reaction. The resulting reaction mixture was centrifuged and filtrated through a filter to remove the precipitate therefrom, and the resulting filtrate was analyzed through HPLC by which the product trans-4-hydroxy-L-proline produced was quantitatively determined.

The HPLC was conducted under the conditions mentioned below.

| | |
|---|---|
| Mobile Phase: | 10 mM citric acid (pH 4.0)/methanol = 3/1 (v/v). |
| Flow Rate: | 1 ml/min. |
| Column: | YMC Pack ODS AQ-312 (produced by YMC Co., 6 × 150 mm). |
| Column Temperature: | 50° C. |
| Wavelength for Detection: | excited wavelength of 503 nm emission wavelength of 541 nm. |

As is shown in Table 9 below, the transformants produced L-proline-4-hydroxylase by from 210 to 1420 times/cell as much as the Dactylosporangium sp. RH1 strain which had been used as the gene source.

TABLE 9

L-proline-4-hydroxylase Activity Produced by Transformants

| Strain | Cell Activity[1] | Relative Activity[2] |
|---|---|---|
| E. coli ATCC12435/pWFH1 | 40.00 | 1428 |
| E. coli ATCC12435/pWFH1[3] | 4.96 | 177 |
| E. coli ATCC12435/pTr14 | 10.68 | 381 |
| E. coli ATCC12435/pTc4OH | 5.98 | 213 |
| E. coli ATCC12435/pTrS30 | Not detected. | — |
| E. coli ATCC12435/pBTTac1 | Not detected. | — |
| Dactylosporangium sp. RH1[4] | 0.028 | 1 |
| Streptomyces griseoviridis JCM4250[5] | 0.020 | 0.7 |
| Streptomyces daghestanicus JCM4365[5] | 0.009 | 0.3 |

[1]Cell activity indicates the enzymatic activity per mg of wet cells (U/mg wet cells). One U indicates the enzymatic activity of producing 1 nmol of trans-4-hydroxy-L-proline per minute (nmol/min).
[2]Relative activity is based on the enzymatic activity produced by Dactylosporangium sp. RH1 strain of being 1 (one).
[3]The strain was cultivated in the same manner as above but in the absence of L-proline in the jar fermenter.
[4]described in (2) of Example 1.
[5]described in (2) of Example 3.

EXAMPLE 12

Construction of an expression plasmid for a fused protein (1) Construction of an expression plasmid for a fused protein with a β-galactosidase protein fragment After 2.4 μg of plasmid pBluescript II KS(+) DNA was cleaved with Restriction endonucleases Eco RV and Xba I, an ethanol precipitate was obtained by the ethanol precipitation. The ethanol precipitate was dissolved in 5 μl of TE.

After 4 μg of plasmid pRH71 DNA was cleaved with Restriction endonuclease Sac I, an ethanol precipitate was obtained in the same manner as mentioned above. After the ethanol precipitate (DNA fragment) was dissolved in 36 μl of TE, both terminals of the DNA fragment were blunted using a Takara DNA Blunting Kit produced by Takara Shuzo Co., Ltd. The treated DNA was subjected to agarose gel electrophoresis. A DNA fragment of approximately 2.4 kb was extracted from the gel in a usual manner, and recovered using a Prep-A-gene produced by Biorad Co. The recovered DNA was cleaved with Xba I, and an ethanol precipitate was obtained in the same manner as mentioned above. The ethanol precipitate (DNA fragment) was dissolved in 10 μl of TE.

The thus-obtained DNA fragment was ligated with Eco RV-Xba I cleaved pBluescript IIKS(+) DNA fragment obtained above.

After E. coli XL2-Blue MRF' strain (produced by Stratagene) was transformed using the thus-ligated DNA, the transformant was spread on LB agar medium containing 50 μg/ml of ampicillin, 0.2 mM IPTG and 40 μg/ml of X-Gal, and cultivated overnight at 37° C.

The plasmid was extracted in a usual manner from the colony grown on the medium, and the structure of the plasmid was identified by digestion with restriction endonuclease.

Further, the PCR was conducted using the plasmid as a template, DNA indicated in Sequence No. 17 as a sense strand primer and DNA indicated in Sequence No. 8 as an anti-sense strand primer. Since a DNA fragment of 50 bp, corresponding to an N-terminal amino acid sequence of L-proline-4-hydroxylase was formed by the above-mentioned reaction, it was identified that the structural gene of the intended L-proline-4-hydroxylase was inserted into the plasmid.

Plasmid pES1-23a in which the structural gene of L-proline-4-hydroxylase was inserted in the same direction as the transcription direction of lac promoter (Plac) in the form fused with 34N-terminal amino acids of β-Gal was obtained by the above-mentioned method as shown in FIG. 7. The amino acid sequence of the fused protein formed is shown in Sequence No. 19.

(2) Construction of an expression plasmid for a fused protein with a maltose binding protein Using DNA indicated in Sequence No.18 as a sense strand primer, DNA indicated in Sequence No. 13 as an antisense strand primer and pRH71 as a template, the PCR was conducted in the same manner as in (2) of Example 8. That is, 20 μl of a reaction mixture containing 0.1 μg of pRH71, 2 μM of the sense strand DNA primer and 2 μM of the anti-sense strand DNAprimer was incubated at 96° C. for 5 minutes. Subsequently, a three step incubation, namely at 96° C. for 2 minutes, at 58° C. for 1 minute and at 75° C. for 1 minute was repeated for a total of 30 times.

After the reaction mixture was subjected to agarose gel electrophoresis, an amplified fragment of 833 bp containing a structural gene of L-proline-4-hydroxylase was extracted in a usual manner, and the DNA fragment was recovered using a Prep-A-gene produced by Biorad Co. The DNA fragment of 833 bp recovered was cleaved with Hind III, and an ethanol precipitate was then obtained by the ethanol precipitation. The ethanol precipitate was dissolved in 5 μl of TE, and used as the structural gene fragment of L-proline-4-hydroxylase.

Plasmid pMAL-c2 having only a structural gene of a maltose binding protein without a signal sequence (Protein Fusion & Purification System produced by New England Biolabs) was cleaved with Xmn I and Hind III while regulating by Ptac.

The structural gene fragment of L-proline-4-hydroxylase was inserted into the Xmn I-Hind III cleavage site of pMAL-c2 using a DNA ligation kit produced by Takara Shuzo Co., Ltd., and transformed *E. coli* XL2-Blue MRF' strain in a usual manner. The transformant was spread on an LB agar medium containing 50 μg/ml of ampicillin, and then cultivated overnight at 37° C. The plasmid was extracted from the thus-obtained colony in a usual manner, and the structure of the plasmid was identified by digestion with restriction endonuclease.

Plasmid pMc4OH in which the DNA fragment encoding the structural gene of L-proline-4-hydroxylase was inserted in the form fused with the structural gene of the maltose binding protein while regulating by Ptac was obtained by the above-mentioned method as shown in FIG. 8. The amino acid sequence of the fused protein formed is shown in Sequence No. 20.

EXAMPLE 13

Production of L-proline-4-hydroxylase by a transformant containing a fused protein expression plasmid

*E. coli* DH1 was transformed using the plasmids pESl-23a and pMc4oH obtained in Example 12. The obtained transformant was cultivated in the same manner as in Example 11 except that a medium containing 0.1 mM IPTG was used, and the productivity of L-proline-4-hydroxylase of the transformant was measured in the same manner as in Example 11.

As shown in Table 10, the transformant produced L-proline-4-hydroxylase in an amount of from 29 to 298 times per cell in comparison to Dactylosporangium sp. RH1 strain used as a gene source.

TABLE 10

Activities of L-proline-4-hydroxylase Produced by Transformants

| Strain | Cell Activity[1] | Relative Activity[3] |
|---|---|---|
| *E. coli* DH1/pES1-23a | 0.80 | 29 |
| *E. coli* DH1/pMc40H | 8.35 | 298 |
| *E. coli* DH1/pBluescript IIKS(+) | Not detected | — |
| *E. coli* DH1/pMAL-c2 | Not detected | — |
| Dactylosporangium sp. RH1[2] | 0.028 | 1 |

[1]The cell activity is shown in terms of enzymatic activity per mg of wet cells (U/mg-wet cells). One U indicates the enzymatic activity of producing 1 nmol of trans-4-hydroxy-L-proline per minute (nmol/min).
[2]described in (2) of Example 1.
[3]The relative activity is shown by defining the enzymatic activity given from Dactylosporangium sp. RH1 strain as 1.

EXAMPLE 14

Construction of Strain Losing Proline Decomposition Activity

A gene putA that participates in the proline decomposition in *E. coli* ATCC12435 was broken according to the method mentioned below to construct a strain losing proline decomposition activity.

Cells of a stock strain *E. coli* ME8395 [F⁻:pvrD34, trD-45, his-68, thyA25, thi deoR33, galK35, xyl-7, mtl-2, malA1, rpsL118, $\lambda^R$ $(\lambda)^-$, appA1, putA::Tn5 (Mu⁺)] available from the National Institute of Genetics were inoculated in LB medium containing 35 μg/ml of kanamycin, and cultivated overnight.

Then 100 μl of a solution of P1 phage was added to and mixed with 100 μl of the resulting culture, and left as it was for 5 minutes.

The resulting mixture was mixed with 3 ml of LB-soft agar medium containing 10 mM of CaCl₂, then layered over an LB-agar medium containing 10 mM of CaCl₂, and cultivated at 37° C. for 7 hours.

After the cultivation, the phage lysate thus formed on the surface of the agar medium was collected in 2 ml of an LB medium containing 10 mM of CaCl₂.

To the liquid thus collected, 0.5 ml of chloroform was added, mixed therewith, using a Vortex mixer, and then centrifuged at 3000 rpm for 15 minutes. The resulting supernatant was used as a P1 phage lysate.

Then 50 μl of the P1 phage lysate liquid was mixed with 100 μl of a culture of *E. coli* ATCC12435 that had been cultivated in an LB medium containing 10 mM of CaCl₂, and then was kept standing at 37° C. for 20 minutes.

The resulting liquid mixture was mixed with 3 ml of F-top-citrate (containing 8.5 g/l of NaCl, 100 mM of disodium citrate, and 0.7% of agar), applied onto an LB-agar medium containing 35 μg/ml of kanamycin, and cultivated at 37° C. for one day.

The kanamycin-resistant cells thus grown through the cultivation were suspended in 0.85% NaCl, then spread onto a Pro-TTC plate (comprising 7 g/liter of K₂HPO₄, 3 g/liter of KH₂PO₄, 0.1 g/liter of MgSO₄, 2 g/liter of proteose peptone, 0.025 g/l of 2,3,5-triphenyltetrazolium chloride, 2 g/l of L-proline and 15 g/l of agar, pH 7.2), and cultivated at 37° C. for 1 to 2 days.

The strain that had produced white colonies on the Pro-TTC plate through the cultivation was selected as a strain losing the activity of decomposing and assimilating proline. Thus was obtained a strain losing proline decomposition activity, E. coli WT1.

The strain WT1 has been deposited with National Institute of Bioscience and Human-Technology, Agency of Industrial Science and Technology in Japan as of Aug. 7, 1996 under FERM BP-5618 in terms of the Budapest Treaty.

EXAMPLE 15

Construction of Plasmid Expressing Proline Biosynthetic Genes proB74 and proA

A plasmid pPF1 was constructed according to the method mentioned below, using the plasmid expressing a mutant gene proB74 (this was mutated from an E. coli-derived gene proB which codes for γ-glutamyl kinase, to be desensitized to the feedback inhibition with proline) and an E. coli-derived gene proA which codes for γ-glutamyl phosphate reductase.

A plasmid pPRO-1 containing E. coli-derived genes proA and DroB [this was obtained from a strain E. coli K83 (FERM BP-2807)] was cleaved with EcoRV and then subjected to agarose gel electrophoresis, from which was obtained a DNA fragment of about 1 kb containing a part of the gene proB, using a Prep-A-gene DNA Purification System (produced by BIO-RAD Co.).

The DNA fragment was ligated with pUC19 (produced by Takara Shuzo Co.) that had been cleaved with SmaI, to obtain a plasmid pBAB51 (see FIG. 9).

The gene proB existing in the plasmid was mutated into a known, mutant gene proB74 as desensitized to the feedback inhibition with proline [see A. M. Dandekar and S. L. Uratsu, J. Bacteriol. 170, 5943 (1988)], according to the method mentioned below.

An oligonucleotide Al as indicated in Sequence No. 21 and an oligonucleotide A2 as indicated in Sequence No. 22 were synthesized, using a DNA synthesizer, 380A•Model (produced by Applied Biosystems Co.).

A partial sequence of the mutant gene ProB74 that had been mutated from proB was amplified through PCR, using apair of primers, oligonucleotide A1 and M13 primer M3 (produced by Takara Shuzo Co. —Catalog No. 3831) and using pBAB51 as a template.

The PCR was conducted, using 20 μl of a reaction mixture comprising 0.1 μg of pBAB51, 2 μM of oligonucleotide A1, 2 μM of M13 primer M3, 1 U of Taq DNA polymerase (produced by Takara Shuzo Co.), 1.6 μl of dNTP mixture (produced by Takara Shuzo Co. —Catalog No. 4030) and 2 μl of an additive buffer. A three step incubation, namely at 94° C. for 30 seconds, at 52° C. for 30 seconds and at 72° C. for 1 minute was repeated for a total of 30 times. Finally, the thus-incubated system was further incubated at 72° C. for 5 minutes.

In the same manner as above, a partial sequence of the mutant gene proB was amplified through PCR, using a pair of primers, oligonucleotide A2 and M13 primer RV (produced by Takara Shuzo Co. —Catalog No. 3830A) and using pBAB51 as a template.

These two DNAs that had been amplified through such PCR were separately subjected to agarose gel electrophoresis and then purified using Prep-A-gene DNA Purification System (produced by BIO-RAD Co.).

In the same manner as above except using a mixture of the two pure DNA fragments as a template along with M13 primer M3 and M13 primer RV as primers, a DNA fragment of about 1 kb containing a nucleotide sequence of proB74 was obtained through PCR and purification.

The DNA fragment was cleaved with EcoO65I and SacII to obtain an EcoO65I-SacII cleaved fragment.

This fragment was ligated with a DNA fragment (of about 6.8 kbp) as obtained from pPRO-1 through digestion with EcoO65I and SacII to construct a plasmid pPRO74, which is different from pPRO-1 in that the proB gene of pPRO-1 has been substituted with the de-sensitized proB74 gene (see FIG. 10).

An oligonucleotide p1 of Sequence No. 23 and an oligonucleotide p2 of Sequence No. 24 were synthesized, using a DNA synthesizer, 380A•Model (produced by Applied Biosystems Co.). proB74 and proA were amplified through PCR, using these p1 and p2 as primers and using pPRO74 as a template.

The PCR was conducted, using 20 μl of a reaction mixture comprising 0.1 μg of pPRO74, 2 μM of p1, 2 μM of p2, 1 U of Takara EX Taq (produced by Takara Shuzo Co.—Code RROO1Q)) and 1.6 μl of dNTP mixture (produced by Takara Shuzo Co.—Catalog No. 4030). A three step incubation, namely at 94° C. for 1 minute, at 42° C. for 2 minute and at 73° C. for 3 minute was repeated for a total of 30 times.

The resulting reaction mixture was subjected to agarose gel electrophoresis, through which was extracted an amplified fragment of 2370 bp containing DroB74 and DroA in a usual manner, and the DNA fragment was collected using GENECLEAN II KIT (produced by BIO 101, Inc.). The thus-collected DNA fragment of 2370 bp was cleaved with HindIII and BamHI, and then an ethanol precipitate was obtained by ethanol precipitation. The ethanol precipitate was dissolved in 5 μl TE and used as a fragment having DroB74 and proA.

The fragment having DroB74 and proA was ligated with a DNA fragment as obtained by digesting a plasmid pSTV29 (produced by Takara Shuzo Co.) with HindIII and BamHI, using a DNA ligation kit (produced by Takara Shuzo Co.) to construct a plasmid having proB74 and proA.

E. coli JM109 strain was transformed with the plasmid obtained above in a usual manner, and the resulting transformant cells were spread on an LB-agar medium comprising 30 μg/ml of chloramphenicol and 0.1 mM of IPTG, 40 μg/ml of X-Gal, and cultivated at 37° C. overnight.

A plasmid was extracted in a usual manner from the strain that had produced white colonies through the cultivation, and the structure of the plasmid was identified by digestion with restriction enzyme.

After the process mentioned above, obtained was a plasmid pPF1 having a de-sensitized gene that codes for a fused protein composed of γ-glutamyl kinase with N-terminal, eight amino acid residues (lacZ.Nterm) of the α-fragment of β-galactosidase as fused to its N-terminal, and having a gene proA under the control of Plac (see FIG. 11).

The nucleotide sequence and the amino acid sequence of the structural gene (lacZ.Nterm-proB74) of the fused protein are indicated by Sequence No. 25.

EXAMPLE 16

Construction of Plasmid Expressing L-proline-4-hydroxylase Gene and Proline Biosynthesis Genes proB74 and proA A plasmid pWFP1 was constructed according to the method mentioned below, the plasmid carrying capable of expressing all of a Dactylosporangium sp. RH1-derived L-proline-4-hydroxylase gene and genes proB74 and proA such as those as produced in Example 15.

The structural gene of L-proline-4-hydroxylase was amplified through PCR, using pWFH1 that had been produced in (3) of Example 10, as a template. For the reaction, used was 20 µl of a reaction mixture comprising 0.1 µg of pWFH1, 0.5 U of Pfu DNA polymerase (produced by STRATAGENE Co.), 2 µl of x10 buffer for Pfu DNA polymerase (produced by STRATAGENE Co.), 2 µl of DMSO, 1 µl of 2.5 mM dNTP, 2 µM of the synthetic DNA as indicated in Sequence No. 26 and 2 µM of the synthetic DNA as indicated in Sequence No. 27. Prior to the subsequent cycle reaction, the reaction mixture was pre-incubated at 96° C. for 5 minutes. A three step incubation, namely at 96° C. for 2 minutes, at 58° C. for 1 minutes and at 75° C. for 3 minute was repeated for a total of 30 times. After thus reacted, the reaction mixture was subjected to agarose gel electrophoresis, through which was extracted an amplified fragment of about 800 pb having an L-proline-4-hydroxylase gene in a usual manner. The DNA fragment was collected, using GENECLEAN II KIT (produced by BIO 101, Inc.). The thus-collected DNA fragment was cleaved with HindIII and EcoRI and then subjected to agarose gel electrophoresis, through which was collected a DNA fragment using GENECLEAN II KIT (produced by BIO 101, Inc.). The thus-collected, L-proline-4-hydroxylase gene fragment was ligated with a DNA fragment as obtained through digestion of a plasmid pBluescriptII KS(+) (produced by STRATAGENE Co.) with HindIII and EcoRI, using a DNA ligation kit (produced by Takara Shuzo Co.), to thereby construct a plasmid pBII-4OH having an L-proline-4-hydroxylase fragment as inserted thereinto (see FIG. 12).

Genes proB74 and DroA were amplified through PCR, using the pPRO74 that had been produced in Example 15, as a template. For the reaction, used was 20 pl of a reaction mixture comprising 0.1 pg of pPRO74, 1 U of Takara Ex Taq (produced by Takara Shuzo Co. —Code RROO1Q), 2 µl of x10 buffer for Takara Ex Taq (produced by Takara Shuzo Co.), 1.6 µl of 2.5 mM DNTP, 2 µM of the synthetic DNA of Sequence No. 28 and 2 µM of the synthetic DNA of Sequence No. 29. A three step incubation, namely at 94° C. for 1 minute, at 42° C. for 2 minutes and at 75° C. for 3 minute was repeated for a total of 30 times. After thus reacted, the reaction mixture was subjected to agarose gel electrophoresis, through which was extracted an amplified fragment of about 2.3 kbp having genes proB74 and proA in a usual manner. The DNA fragment was collected, using GENECLEAN II KIT (produced by BIO 101, Inc.). The thus-collected DNA fragment was cleaved with BamHI and EcoRI, then treated with phenol/chloroform, and precipitated with ethanol, and the DNA fragment was collected. The thus-collected DNA fragment having genes proB74 and proA was ligated with a DNA fragment as obtained through digestion of the plasmid pBII-4OH with HindIII and EcoRI, using a DNA ligation kit (produced by Takara Shuzo Co.), to thereby construct aplasmidpBII-4OHBA having L-proline-4-hydroxylase gene and genes proB74 and proA (see FIG. 13).

The plasmid pBII-40HBA was cleaved with HindIII and BamHI, and then subjected to agarose gel electrophoresis, through which was collected a DNA fragment of about 3.16 kbp having L-proline-4-hydroxylase gene and genes proB74 and proA. On the other hand, pWFH1 that had been produced in (3) of Example 10 was cleaved with HindIII and BamHI, and then subjected to agarose gel electrophoresis, through which was collected a DNA fragment of about 2.6 kbp not having L-proline-4-hydroxylase gene but having a replication-starting point. These two DNA fragments thus obtained were ligated, using a DNA ligation kit (produced by Takara Shuzo Co.), to thereby construct a plasmid pWFP1 capable of expressing L-proline-4-hydroxylase, proB74 protein and proA protein under the control of a tryptophan tandem promoter (see FIG. 14).

EXAMPLE 17

Production of Trans-4-hydroxy-L-proline by Transformant (1) Production of Trans-4-hydroxy-L-proline by Transformant *E. coli* ATCC12435/pTr14

The transformant cells of *E. coli* ATCC12435/pTr14 as obtained in Example 11 were inoculated in 3 ml of an LB medium containing 100 µg/ml of ampicillin and cultivated therein at 30° C. for 16 hours with shaking. The resulting culture was centrifuged, and the amount of trans-4-hydroxy-L-proline in the supernatant thus separated was quantitatively determined.

As a result, 381 µM (50.0 mg/liter) of trans-4-hydroxy-L-proline were formed in the supernatant of the culture of *E. coli* ATCC12435/pTr14.

On the other hand, trans-4-hydroxy-L-proline was not detected in the supernatant of the culture of *E. coli* ATCC12435 which had been used as the host.

(2) Production of Trans-4-hydroxy-L-proline by Transformant *E. coli* ATCC12435/pWFH1

Transformant cells of *E. coli* ATCC12435/pWFH1 were inoculated in 50 ml of a Med4 medium containing 100 µg/ml of ampicillin and 2% of glucose, and cultivated therein at 30° C. for 16 hours with shaking. The culture was used as a seed culture. The seed culture was inoculated in a 5 liter jar fermenter filled with 2 liters of a Med6 medium containing 0.8% of peptone in place of polypeptone and the cells were cultivated in the fermenter under the condition of 400 rpm and 1 vvm, at 33° C.

During the cultivation, glucose was suitably added to the medium so as not to make glucose absent in the medium, and the lowermost limit of the pH of the medium was controlled at 6.5 by adding $NH_4OH$ to the medium.

The culture was centrifuged, and the amount of trans-4-hydroxy-L-proline in the supernatant separated was quantitatively determined. Fifty two hours after the start of the incubation, 10.7 mM (1.4 g/liter) of trans-4-hydroxy-L-proline was produced and accumulated in the supernatant of the culture of *E. coli* ATCC12435/pWFH1.

On the other hand, free trans-4-hydroxy-L-proline was not detected in the supernatant of the culture of *E. coli* ATCC12435 used as the host.

(3) Production of Trans-4-hydroxy-L-proline by Transformant Having Proline Biosynthesis Gene-Expressing Plasmid The strain *E. coli* WT1 as prepared in Example 11 was transformed with the plasmid pPF1 as constructed in Example 15, to obtain a transformant *E. coli* WT1/pPF1.

The strain WT1 as prepared in Example 11 was transformed with the proline 4-hydroxylase-expressing plasmid pWFH1 as constructed in (3) of Example 10, to obtain a transformant *E. coli* WT1/pWFH1.

Competent cells of the transformant *E. coli* WT1/pWFH1 were prepared according to a calcium chloride method, into which was introduced the plasmid pPF1 that had been produced in Example 15. Thus was obtained a transformant *E. coli* WT1/pWFH1/pPF1 having the two plasmids through the selection of the colonies as growing on an LB medium containing 30 µg/ml of chloramphenicol and 50 µg/ml of ampicillin.

Strains of WT1, WT1/pPF1, WT1/pWFH1 and WT1/pWFH1/pPF1 were separately cultivated in LB medium each comprising 37.5 μg/ml of kanamycin, 100 μg/ml of ampicillin, 30 μg/ml of chloramphenicol, or both 100 μg/ml of ampicillin and 30 μg/ml of chloramphenicol, respectively, at 37° C. for 16 hours.

Then 100 μl of each culture was inoculated in a test tube (φ 20×200 mm) filled with 10 ml of a Med7 medium (comprising 2% of glucose, 1% of ammonium sulfate, 0.1% of $K_2HPO_4$, 0.2% of NaCl, 0.05% of $MgSO_4$, 0.0278% of $FeSO_4$, 0.0015% of $CaCl_2$ and 0.8% of peptone) containing 2% (w/v) of calcium carbonate, and cultivated at 30° C. for 24 hours.

The amount of L-proline and that of trans-4-hydroxy-L-proline in the culture supernatant are shown in Table 11.

TABLE 11

| Strain (g/l) | L-proline (g/l) | Trans-4-hydroxy-L-proline |
|---|---|---|
| E. coli WT1 | 0.05 | 0.00 |
| E. coli WT1/pPF1 | 1.20 | 0.00 |
| E. coli WT1/pWFH1 | 0.00 | 0.07 |
| E. coli WT1/pWFH1/pPF1 | 0.20 | 0.67 |

It is known from the above data that the transformants having the proline biosynthesis gene-expressing plasmid pPF1 produced a larger amount of L-proline than the others and that the transformant having both the L-proline 4-hydroxylase-expressing plasmid pWFH1 and the proline biosynthesis gene-expressing plasmid pPF1 produced a larger amount of trans-4-hydroxy-L-proline than the transformant having only the L-proline 4-hydroxylase-expressing plasmid pWFH1.

(4) Production of Trans-4-hydroxy-L-proline by Transformant E. coli WT1/pWFH1/pPF1

The transformant of WT1/pWFH1/pPF1 was inoculated in 50 ml of aMed4G medium [comprising 2% of glucose, 1% of polypeptone (produced by Nippon Seiyaku KK), 0.5% of yeast extract (produced by Difco Co.), 1% of NaCl, 2% of calcium carbonate, pH 7.0] containing 100 μg/ml of ampicillin and 100 μg/ml of chloramphenicol, and cultivated therein at 30° C. for 16 hours with shaking.

The resulting culture was used as a seed culture and inoculated in a 5-liter jar fermenter filled with 2 liters of a Med7 medium, to which was added 100 μg/ml of ampicillin and 30 μg/ml of chloramphenicol. The transformant in the culture was cultivated under the condition of 400 rpm and 1 vvm, at 30° C.

At 8 hours after the start of cultivation, IPTG was added to the medium so as to make the IPTG concentration of 0.2 mM.

At 24 hours after the start of cultivation, ampicillin and chloramphenicol were added to the medium so as to make ampicillin concentration of 100 μg/ml and the chloramphenicol concentration of 30 μg/ml.

During the cultivation, glucose was suitably added to the medium so as to make the glucose concentration of about 1%, and the lowermost limit of the pH of the medium was controlled at 6.5 by adding $NH_4OH$ to the medium. Five hours after the start of the cultivation, the concentration of the dissolved oxygen in the culture was controlled to be 1/15 of that at the start of the cultivation by varying the stirring speed within the range between 250 rpm and 700 rpm.

The culture was centrifuged, and the amount of trans-4-hydroxy-L-proline in the supernatant was quantitatively determined. Ninety nine hours after the start of the cultivation, 156 mM (20.5 g/l) of trans-4-hydroxy-L-proline was produced and accumulated in the supernatant of the culture of E. coli WT1/pWFH1/pPF1.

(5) Production of Trans-4-hydroxy-L-proline by Transformant Having Plasmid Expressing L-proline 4-Hydroxylase Gene and Proline Biosynthesis Gene The strain E. coli WT1 as prepared in Example 15 was transformed with the plasmid pWFP1 as constructed in Example 16, to obtain a transformant E. coli WT1/pWFP1.

The transformant of E. coli WT1/pWFP1 was cultivated in an LB medium containing 100 μg/ml of ampicillin, at 37° C. for 16 hours. Then 100 μl of the culture was inoculated in a test tube (φ20×200 mm) filled with 10 ml of a Med7 medium containing 2% (w/v) of calcium carbonate, and cultivated therein at 30° C. for 24 hours.

The amount of L-proline in the supernatant of the culture was 0.56 g/liter, and that of trans-4-hydroxy-L-proline in the same was 2.4 g/liter.

(6) Production of Trans-4-hydroxy-L-proline by Transformant E. coli WT1/pWFP1

The transformant of WT1/pWFP1 was inoculated in 50 ml of a Med4G medium containing 100 μg/ml of ampicillin, and cultivated therein at 30° C. for 16 hours with shaking.

The resulting culture was used as a seed culture and inoculated in a 5-liter jar fermenter filled with 2 liters of a Med7 medium, to which was added 100 μg/ml of ampicillin. The ransformant in the culture was cultivated under the condition of 400 rpm and 1 vvm, at 30° C.

At 24 hours after the start of cultivation, ampicillin was added to the medium so as to make the ampicillin concentration of 100 μg/ml.

During the cultivation, glucose was suitably added to the medium so as to make constantly the glucose concentration of about 1%, and the lowermost limit of the pH of the medium was controlled at 6.5 by adding $NH_4OH$ to the medium. Five hours after the start of the cultivation, the concentration of the dissolved oxygen in the culture was controlled to be 1/15 of that at the start of the cultivation by varying the stirring speed within the range between 250 rpm and 700 rpm.

The culture was centrifuged, and the amount of trans-4-hydroxy-L-proline in the supernatant was quantitatively determined. Ninety nine hours after the start of the cultivation, 191 mM (25.0 g/l) of trans-4-hydroxy-L-proline was produced and accumulated in the supernatant of the culture of E. coli WT1/pWFP1.

(7) Production of Trans-4-hydroxy-L-proline by Transformant E. coli ATCC12435/pWFH1

Transformant cells of E. coli ATCC12435/pWFH1 were inoculated in 50 ml of a Med4 medium containing 100 μg/ml of ampicillin and cultivated therein at 30° C. for 16 hours with shaking. The culture was used as a seed culture. The seed culture was inoculated in a 5 liter jar fermenter filled with 2 liters of a Med6medium. 200 mM of L-proline was added to the medium. The cells were cultivated in the fermenter under the condition of 400 rpm and 1 vvm, at 30° C.

During the incubation, glucose and L-proline were suitably added to the medium in such a manner that glucose was always present in the medium and that L-proline could be at about 50 mM therein, and the lowermost limit of the pH of the medium was controlled at 6.5 by adding $NH_4OH$ to the medium.

The culture was centrifuged, and the amount of trans-4-hydroxy-L-proline in the supernatant separated was quantitatively determined. Seventy two hours after the start of the incubation, 185 mM (24 g/liter) of trans-4-hydroxy-L-proline was produced and accumulated in the supernatant of the culture of E. coli ATCC12435/pWFH1.

On the other hand, free trans-4-hydroxy-L-proline was not detected in the supernatant of the culture of E. coli ATCC12435 used as the host.

(8) Production of Trans-4-hydroxy-L-proline by Transformant E. coli ATCC12435/pMc4OH Transformant cells of E. coli ATCC12435/pMc4OH were inoculated in 50 ml of a Med4 medium containing 100 µg/ml of ampicillin and cultivated therein at 30° C. for 16 hours with shaking. The culture was used as a seed culture. The seed culture was inoculated in a 5 liter jar fermenter filled with 2 liters of a Med6 medium. 200 mM of L-proline was added to the medium. The cells were cultivated in the fermenter under the condition of 400 rpm and 1 vvm, at 30° C.

During the incubation, glucose and L-proline were suitably added to the medium in such a manner that glucose was always present in the medium and that L-proline could be at about 50 mM therein, and the lowermost limit of the pH of the medium was controlled at 6.5 by adding $NH_4OH$ to the medium.

The culture was centrifuged, and the amount of trans-4-hydroxy-L-proline in the supernatant separated was quantitatively determined. Seventy two hours after the start of the incubation, 85.4 mM (11.2 g/liter) of trans-4-hydroxy-L-proline was produced and accumulated in the supernatant of the culture of E. coli ATCC12435/pMc4OH.

On the other hand, free trans-4-hydroxy-L-proline was not detected in the supernatant of the culture of E. coli ATCC12435 which had been used as the host.

EXAMPLE 18

Conversion of L-proline into Trans-4-hydroxy-L-proline with Transformant cells

Transformant cells of E. coli ATCC12435/pTr14 were inoculated in 10 ml of an LB medium containing 50 µg/ml of ampicillin and cultivated therein overnight at 30° C. with shaking. The culture was centrifuged to collect the cells. If desired, the cells were frozen and stored at −20° C. and thawed before use.

The cells were added to 250 µl of a reaction mixture (comprising 20 mM L-proline, 24 mM 2-ketoglutaric acid, 4 mM ferrous sulfate and 8 mM L-ascorbic acid in 240 mM MES buffer, pH 6.5) at 10% (w/v) in terms of the wet cells, and reacted at 35° C. for 60 minutes. The amount of trans-4-hydroxy-L-proline as formed in the reaction mixture was quantitatively determined. In the mixture, 11.5 mM (1.5 g/liter) of trans-4-hydroxy-L-proline was produced.

What is claimed is:

1. An isolated and purified L-proline-4-hydroxylase having the following physicochemical properties:
   (1) Action and Substrate Specificity:
      It catalyzes hydroxylation of L-proline at the 4-position of L-proline in the presence of 2-ketoglutaric acid and a divalent iron ion to produce trans-4-hydroxy-L-proline
   (2) Optimum pH Range:
      The enzyme has an optimum pH range of 6.0 to 7.0 for its reaction at 30° C. for 20 minutes,
   (3) Stable pH Range:
      The enzyme is stable at pH values of 6.5 to 10.0, when it is allowed to stand 40° for 24 hours,
   (4) Optimum Temperature Range:
      The optimum temperature range is 30° to 40° C. when it is allowed to stand at pH 6.5 for 15 minutes,
   (5) Stable Temperature Range:
      The enzyme is inactivated, when it is allowed to stand at pH 9.0 and at 500 for 30 minutes,
   (6) Inhibitors:
      The enzyme is inhibited by metal ions of $Zn^{++}$ and $Cu^{++}$ and ethylenediaminetetraacetic acid, and not inhibited by 2-ketoglutaric acid,
   (7) Activation:
      The enzyme does not need any cofactor for its activation, L-ascorbic acid accelerates the reaction and catalase does not accelerate the reaction,
   (8) Km Value:
      Km value is 0.27 mM for L-proline when determined in a 80 mM 2-(N-morpholino)ethanesulfonic acid (MES) buffer (pH 6.5) containing 8 mM 2-ketoglutaric acid, 4 mM L-ascorbic acid, 2 mM ferrous sulfate and a predetermined amount of the enzyme at 30° C. for 20 minutes,
      Km value is 0.55 mM for 2-ketoglutaric acid, when determined in a 80 mM 2-(N-morpholino) ethanesulfonic acid (MES) buffer (pH 6.5) containing 4 mM L-proline, 4 mM L-ascorbic acid, 2 mM ferrous sulfate and a predetermined amount of the enzyme at 30° C. for 20 minutes,
   (9) Molecular Weight:
      The enzyme has a molecular weight of 32,000±5,000 daltons by sodium dodecylsulfate-polyacrylamide gel electrophoresis and of 43,800±5,000 daltons by gel filtration,
   (10) N-terminal Amino Acid Sequence:
      The enzyme has an N-terminal amino acid sequence as in Sequence No. 1,

| Sequence No. 1: | | |
| --- | --- | --- |
| (N-terminal) | 1 | MetLeuthrProThrGluLeuLysGlnTyr |
| | 11 | ArgGluAlaGlyTyrLeuLeuIleGluAsp |
| | 21 | GlyLeuGlyProArgGluVal. |

2. The isolated and purified L-proline-4-hydroxylase according to claim 1, wherein said L-proline-4-hydroxylase is isolated from a microorganism selected from the group consisting of *Dactylosporangium sp.* RH1 deposited with the National Institute of Bioscience and Human-Technology Agency of Industrial Science and Technology, Japan, under the designation FERM BP-4400 and Amycolatopsis sp. RH2 deposited as FERM BP-4581.

3. The isolated and purified L-proline-4-hydroxylase according to claim 1, wherein said L-proline-4-hydroxylase is isolated from a microorganism selected from the group consisting of *Streptomyces griseoviridis* deposited as JCM4250 and *Streptomyces daghestanicus* deposited as JCM4365 with the Japan Collection of Microorganisms, RIKEN (The Institute of Physical and Chemical Research).

4. An isolated and purified protein comprising the amino acid sequence of residues 8 to 272 defined in SEQ ID NO: 2.

* * * * *